United States Patent [19]

Semple

[11] Patent Number: 4,948,418
[45] Date of Patent: Aug. 14, 1990

[54] 2,3-DIHYDROBENZO[B]THIOPHENES

[75] Inventor: Joseph E. Semple, Wilmington, Del.

[73] Assignee: E. I. Du Pont de Nemours and Company, Wilmington, Del.

[21] Appl. No.: 402,178

[22] Filed: Aug. 30, 1989

Related U.S. Application Data

[60] Division of Ser. No. 202,086, Jun. 2, 1988, Pat. No. 4,881,967, which is a continuation-in-part of Ser. No. 943,365, Dec. 10, 1986, abandoned.

[51] Int. Cl.$^5$ .................. A01N 43/707; A01N 43/90; A01N 43/12; C07D 409/04
[52] U.S. Cl. .......................................... 71/92; 71/91; 71/93; 71/94; 71/96; 549/58; 549/51; 549/5; 548/465; 548/406; 548/110; 548/369; 548/259; 548/144; 548/251; 548/309; 548/263.2; 548/263.8; 540/578; 546/142; 546/119; 546/121; 546/14; 544/48; 544/229; 544/236; 544/182
[58] Field of Search .................. 71/90, 91, 93, 92, 94, 71/96; 549/58, 51, 5; 548/465, 369, 251, 406, 110, 259, 144, 309, 265; 546/142, 14, 119, 121; 544/48, 182, 229, 236; 540/578

[56] References Cited

U.S. PATENT DOCUMENTS

| | | | |
|---|---|---|---|
| 3,385,862 | 5/1968 | Metivier et al. | 71/92 |
| 4,213,773 | 7/1980 | Wolf | 71/92 |
| 4,406,910 | 9/1983 | Pilgram | 424/272 |
| 4,431,822 | 2/1984 | Nagano et al. | 548/513 |
| 4,437,877 | 3/1984 | Nagano et al. | 71/90 |
| 4,452,981 | 6/1984 | Nagano et al. | 71/92 |
| 4,536,209 | 8/1985 | Jikihara et al. | 71/96 |
| 4,554,283 | 11/1985 | Pilgram et al. | 514/364 |
| 4,599,104 | 7/1986 | Nagano et al. | 71/92 |
| 4,668,278 | 5/1987 | Haga et al. | 71/92 |
| 4,670,043 | 6/1987 | Nagano et al. | 71/92 |
| 4,670,046 | 6/1987 | Nagano et al. | 71/96 |
| 4,740,619 | 4/1988 | Haga et al. | 564/249 |
| 4,766,233 | 8/1988 | Lyga | 544/182 |

FOREIGN PATENT DOCUMENTS

| | | |
|---|---|---|
| 8541462 | 5/1985 | Australia . |
| 170191 | 2/1986 | European Pat. Off. . |
| 59-204181 | 11/1984 | Japan . |
| 60-233075 | 11/1985 | Japan . |
| 61-040261 | 2/1986 | Japan . |
| 85/01939 | 5/1985 | World Int. Prop. O. . |

Primary Examiner—John M. Ford

[57] ABSTRACT

This invention pertains to novel heterocyclic 2,3-dihydrobenzofuran and chromane compounds, including stereoisomers, agriculturally suitable compositions containing them, and their use as broad spectrum herbicides.

29 Claims, No Drawings

2,3-DIHYDROBENZO[B]THIOPHENES

RELATED APPLICATION

This is a continuation division of application Ser. No. 07/202,086, filed June 2, 1988, now U.S. Pat. No. 4,881,967, which is a continuation in part of copending application 06/943,365 filed Dec. 10, 1986.

BACKGROUND OF THE INVENTION

Novel heterocyclic 2,3-dihydrobenzofuran and chromane herbicides show utility as agrichemicals.

EP-A-No. 170191, published Feb. 5, 1986 discloses herbicidal compounds of the following formula.

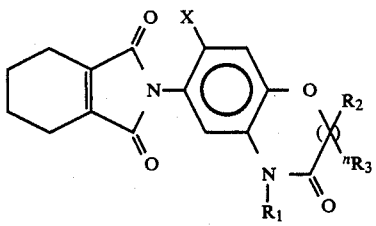

where
X is H, Cl or F;
n is 0 or 1;
$R_1$ is H, alkyl, alkenyl, alkynyl, haloalkyl, haloalkenyl,- haloalkynyl, alkoxyalkyl, or alkoxyalkoxyalkyl; and
$R_2$ and $R_3$ are H, halogen, alkyl or phenyl.

U.S. Pat. No. 4,431,822 (filed Mar. 23, 1982) discloses compounds of the following formula as herbicides.

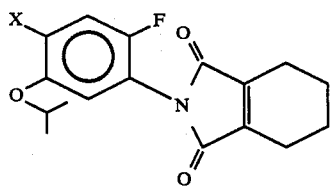

U.S. Pat. No. 4,406,910 filed May 6, 1982 discloses compounds of the following formula as pesticides (insecticides).

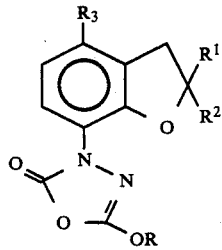

wherein
R is alkyl of 1–2 carbons or propynyl;
$R^1$ is H or alkyl of 1–3 carbons;
$R^2$ is alkyl of 1–3 carbons; and
$R^3$ is H, Cl, Br or Alkyl of 1–3 carbons.

U.S. Pat. No. 4,670,046 discloses compounds of the following formula as herbicides.

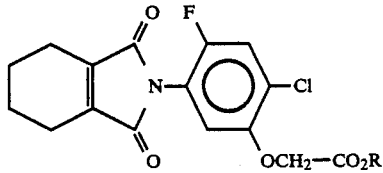

U.S. Pat. No. 4,536,209 disclosed compounds of the following formula as herbicides.

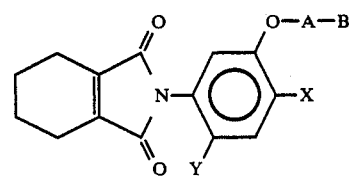

wherein in part
X and Y are H or halogen;
A is

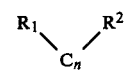

and;
B is $CO_2R^3$

JP No. 60,233,075 discloses compounds of the following formula as herbicides.

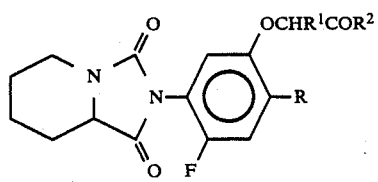

wherein in part
R is Cl or Br;
$R_1$ is H, alkyl or Ph; and
$R_2$ is $OR^3$, $SR^4$ or $NR^5R^6$.

U.S. Pat. No. 4,437,877 discloses compounds of the following formula as herbicides.

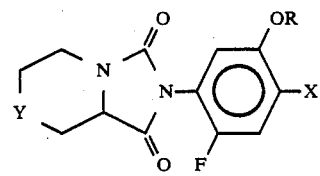

wherein in part
R is alkyl, allyl or propargyl.

U.S. Pat. No. 4,452,981 discloses compounds of the following formula as herbicides.

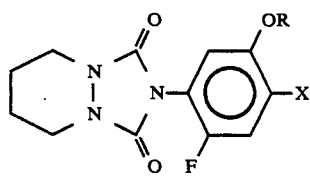

wherein in part
R is alkyl, allyl or propargyl.

JP No. 59,204,181 discloses compounds of the following formula as herbicides.

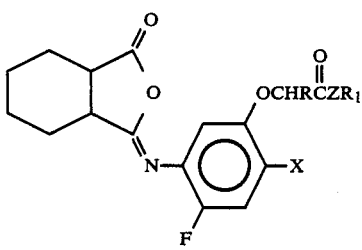

U.S. Pat. No. 4,599,104 discloses compounds of the following formula as herbicides.

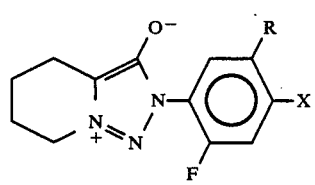

wherein in part
R is H, alkoxy alkynyloxy or alkenyloxy.

U.S. Pat. No. 4,670,043 discloses compounds of the following formula as herbicides.

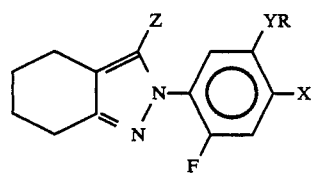

wherein in part
Y is O; and
R is alkyl, alkenyl or alkynyl.

EP-A No. 142,769 discloses compounds of the following formula as herbicides.

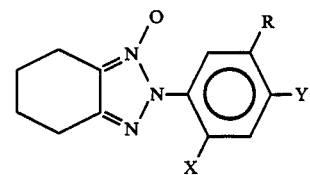

U.S. Pat. No. 3,385,862 discloses a compound of the following formula as a herbicide. This compound is known as Ronstar ™.

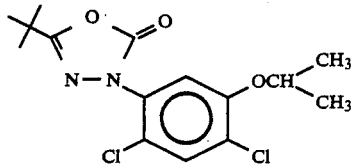

EP-A No. 161,304 discloses compounds of the following formula as herbicides.

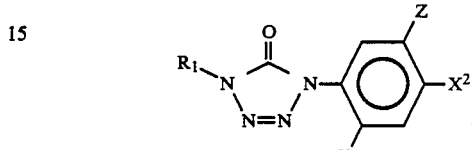

wherein in part
Z is alkoxy.

DE No. 3,514,057 discloses compounds of the following formula as herbicides.

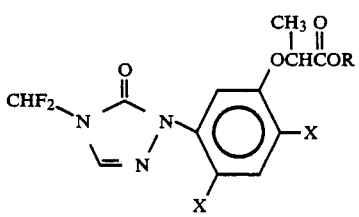

PCT Publication No. WO 86/00072 discloses compounds of the following formula as herbicides.

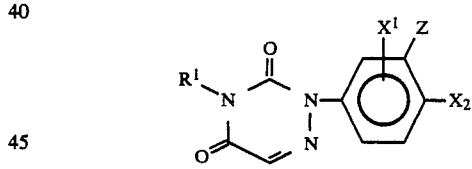

wherein in part
Z is QR;
Q is O or S; and
R is alkyl.

JP No. 61,40,261 discloses compounds of the following formula as herbicides

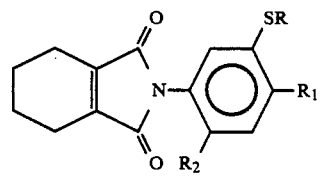

wherein in part
$R_1$ and $R_2$ are halogen; and
R is H and haloalkyl; and

U.S. Pat. No. 4,213,773 discloses compounds of the following formula as herbicides.

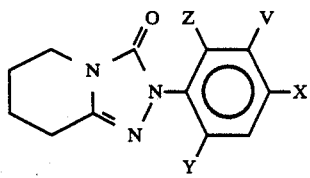

wherein in part
X and Y are halogen;
Z is H or halogen;
V is OR₁; and
R₁ is alkyl, alkenyl or alkynyl.

The presence of undesired vegetation causes substantial damage to useful crops, especially agricultural products that satisfy man's basic food needs, such as soybeans, barley, wheat, and the like. The current population explosion and concomitant world food shortage demand improvements in the efficiency of producing these crops. Prevention or minimizing the loss of a portion of valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention pertains to compounds of formula I including stereoisomers, agriculturally suitable compositions containing them, and their use as broad spectrum herbicides.

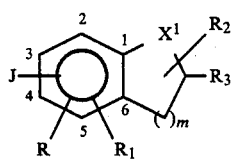

wherein,
R is H, Cl, F, $C_1$-$C_2$ alkyl or $C_1$-$C_3$ alkoxy;
R₁ is H, F, Cl, Br, CH₃, OCH₃, CN, CF₃, OCF₃ or OCF₂H;
X¹ is O or S;
R₂ is H, CH₃ or CH₂CH₃;
R₃ is H, $C_1$-$C_4$ haloalkyl, CR₂R₇CN, CN, CR₂R₄R₇, COCl, COR₄, C(NOR₆)R₂, CO₂R₄, CONR₄R₂, CHR₂OH, CO₂(CH₂)₂Si(CH₃)₃, CONR₂SO₂CH₃, CHR₂CO₂R₄, CONHCH(CH₃)CONHCH(CH₃)CO₂CH₃, CHR₂COR₄, CHR₂OSO₂($C_1$-$C_4$ alkyl), CHR₂OC(O)R₄, CHR₂OC(O)N(R₂)₂, CHR₂OC(O)N(R₂)OCH₃, CHR₂OC(O)N(R₂)Ph, HC=CH₂ or C≡CH;
R₄ is H, $C_1$-$C_4$ alkyl, $C_1$-$C_4$ haloalkyl, $C_2$-$C_6$ alkenyl, $C_3$-$C_6$ alkynyl, $C_2$-$C_4$ haloalkenyl, phenyl, $C_1$-$C_4$ alkylphenyl, $C_3$-$C_6$ alkoxycarbonylalkyl or (CH₂CH₂O)$_b$R₂;
b is 1 to 6;
m and n are independently 1 or 2;
J is

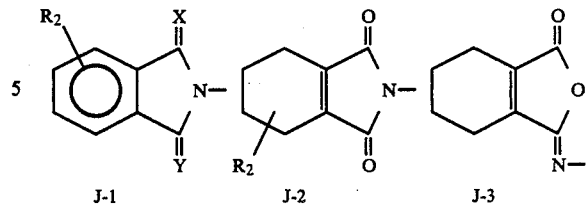

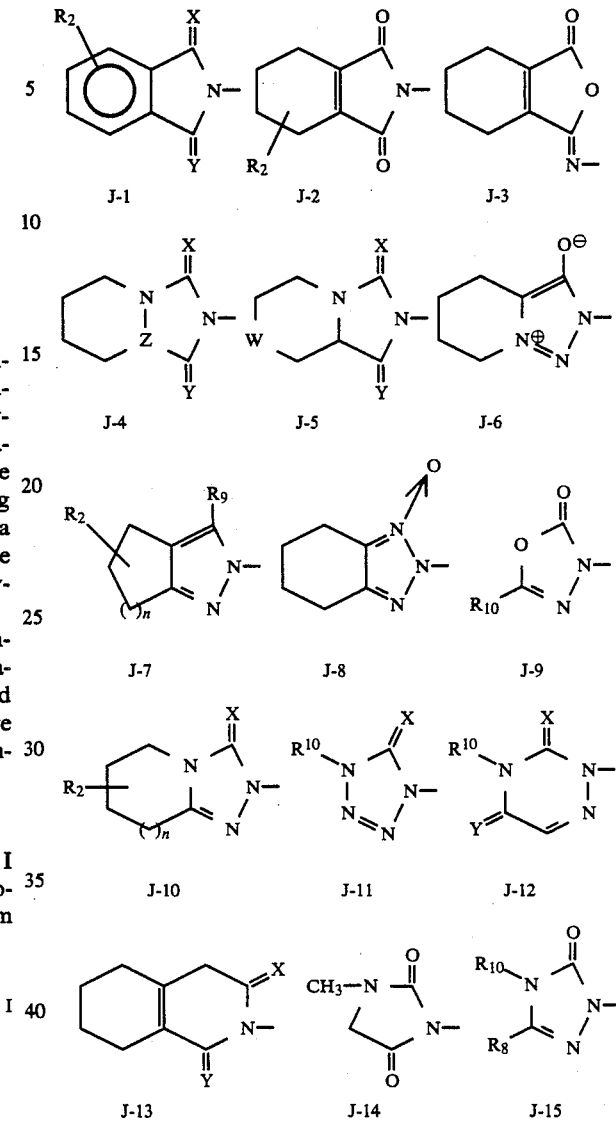

wherein
X and Y each is O or S;
Z is C or N;
W is S or SO₂;
R₆ is H, $C_1$-$C_5$ alkyl, allyl, propargyl, benzyl, CH₂CO₂CH₃ or CH₂CO₂CH₂CH₃;
R₇ is H or CH₃;
R₈ is Cl, $C_1$-$C_4$ alkyl or $C_1$-$C_4$ haloalkyl;
R₉ is Cl, F, Br, CH₃, CN, OCH₃, SCH₃ or SO₂CH₃; and
R₁₀ is $C_1$-$C_4$ alkyl or $C_1$-$C_4$ haloalkyl.

Preferred compounds are:
1. Compounds of formula 1 wherein
    R and R₁ are H or halogen; and
    R₂ is H.
2. Compounds of Preferred 1 wherein
    R₄ is H, $C_1$-$C_3$ alkyl, $C_1$-$C_2$ haloalkyl, allyl, propargyl, $C_3$ haloalkenyl, $C_3$-$C_4$ alkoxycarbonylalkyl or (CH₂CH₂O)$_b$R₂; and
    b is 1 or 2.
3. Compounds of Preferred 2 wherein
    R₃ is H, CN, $C_1$-$C_2$ haloalkyl, CR₂R₇R₄, CR₂R₇CN, CH=CH₂, C≡CH, COCl, COR₄, C(NOR₆)R₂, CO₂R₄, CH₂COR₄, CH₂CO₂R₄, CH₂OC(O)R₄ or CH₂OC(O)N(CH₃)₂; and R₆ is H allyl, C₁–C₃ alkyl or CH₂CO₂CH₂CH₃.

4 Compounds of Preferred 3 wherein
J is J-2, J-3, J-4, J-7, J-9, J-10, J-11, J-12 or J-15; and
X and Y are O.

5. Compounds of Preferred 4 wherein
R₉ is Cl or Br; and
R₈ is CH₃.

6. Compounds of Preferred 5 wherein
J is J₂ or J₁₀; and
X¹ is O.

7. Compounds of Preferred 6 wherein
J is in the 5 position;
R is F or Cl and in the 4 position; and
R₁ is Cl or Br and in the 2 position.

8. Compounds of Preferred 6 wherein
J is in the 4 position;
R is F or Cl and is in the 3 position; and
R₁ is H.

9. Compounds of Preferred 6 wherein
J is in the 3 position;
R is F or Cl and is in the 4 position; and
R₁ is H.

10. Compounds of Preferred 6 wherein
J is in the 2 position;
R is F or Cl and is in the 3 position; and
R₁ is Cl or Br and is in the 5 position.

11. Compounds of Preferred 7 wherein
J is J-2.

12. Compounds of Preferred 7 wherein
J is J-10 and
n is 1.

13. Compounds of Preferred 11 wherein
m is 2.

14. Compounds of Preferred 12 wherein
m is 1.

15. A method-of-use of the compounds of Preferred 14 for the control of nightshade in cereal crops.

Specifically Preferred

Specifically preferred for reasons of ease of synthesis and/or biological activity are 2-BENZOFURANMETHANOL-7-CHLORO-5-FLUORO-4-(2,3,4,5,6,7-HEXAHYDRO-1,3-DIOXO-1H-ISOINDOL-2-yl)-2,3-DIHYDRO-α-METHYL, ACETATE.

((1,2,4))-TRIAZOLO((4,3-A)) PYRIDIN-3(2H)-ONE, 2-(5,7-DICHLORO-2,3-DIHYDRO-2-METHYL-4-BENZO-FURANYL)-5,6,7,8-TETRAHYDRO-.

2-BENZOFURANCARBOXYLIC ACID-7-CHLORO-5-FLUORO-4-(2,3,4,5,6,7-HEXAHYDRO-1,3-DIOXO-1H-ISOINDOL-2-YL)-2,3-DIHYDRO-, METHYL ESTER.

In these compounds, each aliphatic moiety can be either straight chain or branched-chain. "Halogen" is bromine, chlorine and fluorine.

DETAILED DESCRIPTION OF THE INVENTION

Compounds of formula I wherein J is J-1, J-2 or J-10, X and Y are oxygen, m is one, n is one or two, R₂ is hyrdogen, methyl or ethyl and R₃ is CHR₄R₇, can be prepared by cyclizing the appropriate J-1, J-2 and J-10 allyl phenols of formula II as outlined in Scheme I Scheme I

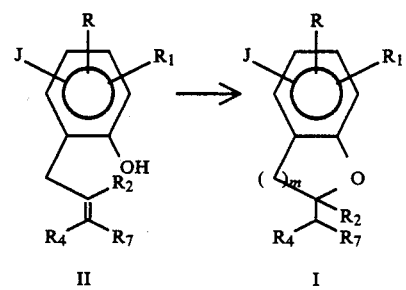

The cyclization can be effected by one or more of three general methods:

(a) thermal: the phenol precursor II, optionally in a solvent such as xylene, is heated at 150°–250° C.;

(b) acid catalyzed: refluxing a solution of the phenol precursor II in an inert solvent, such as xylene, containing a catalytic amount of p-toluenesulfonic acid (PTSA).

(c) free-radical: treating the phenol precursor II with hydrogen bromide in the presence of a peroxide.

Such methods are described by L. I. Smith, Chemical Reviews, page 287, et seq., 1940.

Depending on the nature of substituents R₂, R₄, and R₇ in II, the above cyclization process may produce varying amounts of I in which m is one and/or two.

In addition to the methods described above, compounds of the subclass of formula I wherein J is J-1, J-2 or J-10, X is oxygen, m is one or two, n is one or two, R₂ is hydrogen, methyl or ethyl, and R₃ is hydrogen, CR₂R₇CN, CN, CR₂R₄R₇, COR₄, C(NOR₆)R₂, CO₂R₄, CONR₄R₂, CHR₂CO₂R₄, CHR₂C(O)R₄, CHR₂OC(O)R₄, CHR₂OC(O)N(R₂)₂, CH=CH₂ or C≡CH, may be prepared by dehydration of the precursor III. A preferred method is by refluxing a mixture of III with PTSA in a suitable inert solvent such as xylene. Alternatively, contacting III with a mixture of triphenylphosphine and diethylazodicarboxylate in an inert solvent such as tetrahydrofuran at about 0° C. to 25° C., according to the method of R. G. Salomon et al., *J. Org. Chem.*, 52, 1072 (1987), produces I, where m=2. This is outlined in Scheme II.

Scheme II

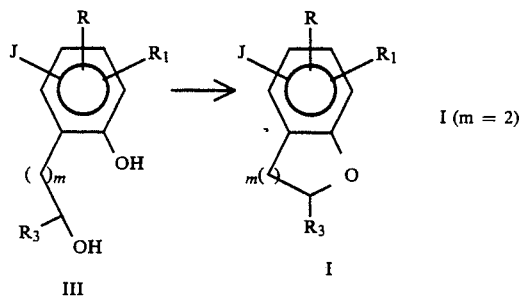

The intermediate diol derivative III, where m is 2, is produced from the allyl phenol precursor IV by treatment of IV, where R₃ is as previously defined, with borane or 9-BBN (9-borabicyclo[3.3.1]nonane) in an inert solvent such as tetrahydrofuran at 0° C. to 70° C. The resultant organoborane is oxidized with a basic hydrogen peroxide solution from 0° C. to 55° C. following the general procedures described by H. C. Brown, *Organic Synthesis via Boranes*, WIley Interscience, N.Y., 1975; H. C. Brown and C. G. Scouten, *J. Org. Chem.*, 38, 4092 (1973). This is outlined in Scheme III.

Scheme III

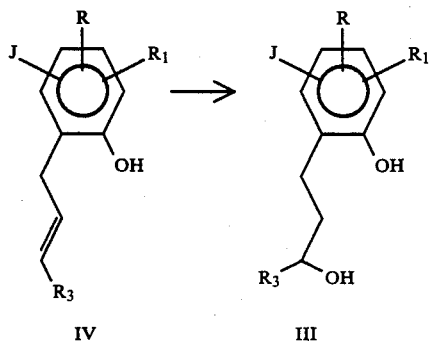

IV    III

Compounds of formula I wherein J is as previously described also can be prepared by treating phenol II with a moderate stoichiometric excess of an epoxidizing agent such as peracetic acid, m-chloroperoxybenzoic acid or a like reagent, in an inert solvent such as 1,2-dichloroethane at a temperature of about 0°–80° C., to form an epoxide of formula V.

Scheme IV

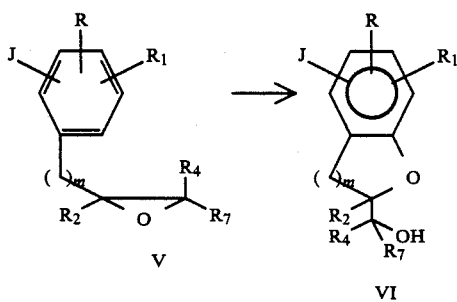

V    VI

The reaction preferably is conducted by refluxing the mixture of phenol, epoxidizing agent and solvent until the reaction is complete, then treating the mixture with an aqueous solution of sodium sulfite until no reaction is obtained on starch/potassium iodide paper.

The epoxide V may spontaneously cyclize at room temperature, or it may be cyclized by (a) an acid catalyst (PTSA) and/or like protic catalyst in an inert solvent such as 1,2-dichloroethane, or (b) a basic catalyst, such as sodium hydride or a tertiary amine, in an inert solvent such as tetrahydrofuran (THF) or N,N-dimethylformamide (DMF) at a temperature of about 0° C. to 100° C. The products are characterized by formula VI, as Outlined in Scheme IV.

The phenol precursors II and IIA can be prepared by Claisen rearrangement of the appropriate substituted compounds of formula VII as outlined in Scheme V.

Scheme V

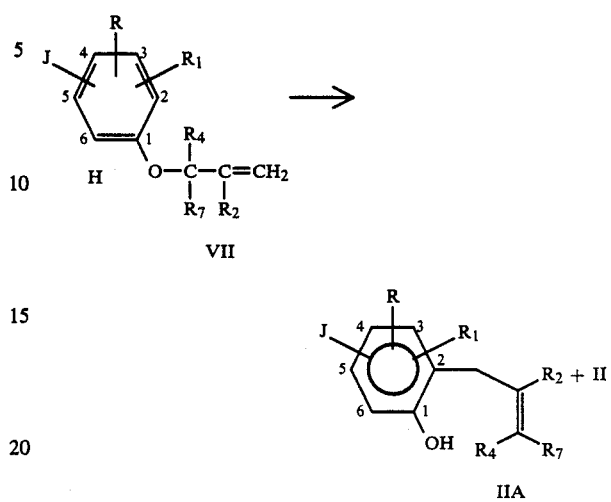

VII

IIA

When $R^1$ is hydrogen at position two, the product is ordinarily a mixture of the two isomeric forms IIA an II. When $R^1$ is other than hydrogen, only the isomeric form II is obtained. The rearrangement is effected by heating the allyloxyphenyl precursor VII at a moderately elevated temperature—for example a temperature within the range of from about 120° C. to about 250° C. The precursor VII per se (i.e., neat) may be used or it may be in solution in a suitable inert solvent, such as N,N-dimethylaniline. Alternatively, the rearrangement can be effected at about 0° C. to room temperature by employing a Lewis acid catalyst, such as boron trichloride, in an inert solvent, such as methylene chloride, following a procedure described by R. Barner, et al., *Helv. Chim. Acta*, 56, 14 (1973). It is to be noted that in some cases, at least, when the precursor is heated at a temperature within the upper portion of the indicated range—for example, above about 200° C.—cyclization may occur, in addition to the rearrangement.

Generally speaking, mixtures of the benzofuran and benzopyran will be obtained from all of the cyclization procedures, the relative proportions of the two materials depending upon the character of the moieties $R_2$, $R_4$ and $R_7$ and the method, (a), (b), (c), or epoxidation, followed by treatment with acid or base to effect the cyclization.

Allyloxyphenyl precursors VII can be prepared by treating a solution of the appropriate substituted compounds of formula VIII with appropriate allyl halides IX.

Scheme VI

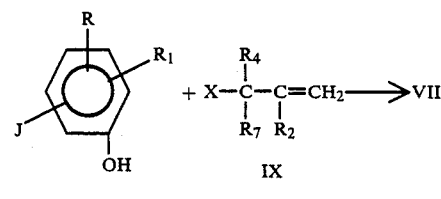

VIII    IX

The reaction is best run with the bromide at about room temperature to 100° C. in an inert solvent (such as acetone, acetonitrile or N,N-dimethylformamide) in the presence of Potassium carbonate.

Precursor phenols VIII can be prepared by conventional procedures, as by heating a mixture of an appropriate phthalic or 3,4,5,6-tetrahydrophthalic anhydride and an appropriate aniline X

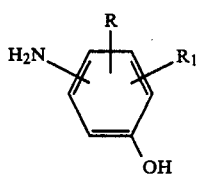

X in acetic acid, toluene or xylene. The reaction can be catalyzed in xylene or toluene by an amine such as triethylamine or DBU (1,8-diazabicyclo[5.4.0]-undec-7-ene). Procedures for preparing such precursor phenols VIII are well known, being described inter alia, in U.S. Pat. No. 4,452,981, European Patent Application No. 61,741 and United Kingdom Patent Application No. 2,046,754, and in references cited therein.

Alternatively, allyloxyphenyl precursors VII can be prepared by heating a mixture of an appropriate anhydride, such as phthalic or 3,4,5,6-tetrahydrophthalic anhydride, and an appropriate allyloxyaniline of formula XI

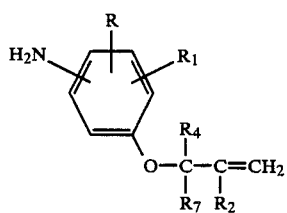

XI in acetic acid, these anilines being prepared from the corresponding allyloxynitrobenzenes (as by treating the nitrobenzene with stannous chloride in a solvent. such as ethyl acetate), the allyloxynitrobenzenes being prepared by treating the corresponding nitrophenols with the appropriate allyl halides IX as described earlier in Scheme VI.

The thio-analogs, where J is as defined in the 5-position, $R_2$ is hydrogen, R is fluorine and is in the 4-position and $R_1$ is chlorine and is in the 2-position, may be prepared as described below. The allylphenol XII when treated with N,N-dimethylthiocarbamoyl chloride in the presence of DABCO (1,4-diazabicyclo[2.2.2]octane) in DMF at about 0° C. to room temperature affords thiocarbamate XIII as outlined in Scheme VII.

Scheme VII

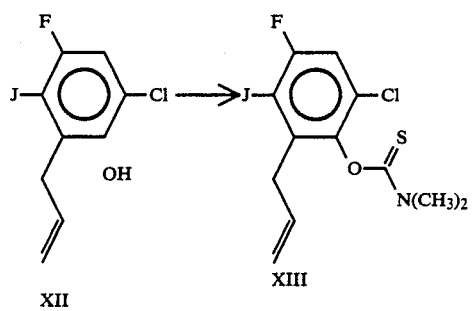

Thermal rearrangement of XIII may be effected in a suitable inert solvent such as o-dichlorobenzene at 150°–250° C. to produce carbamate derivative XIV. Cyclization of XIV with an anhydrous acid, such as hydrogen bromide in acetic acid at refluxing temperatures affords XV as outlined in Scheme VIII.

Scheme VIII

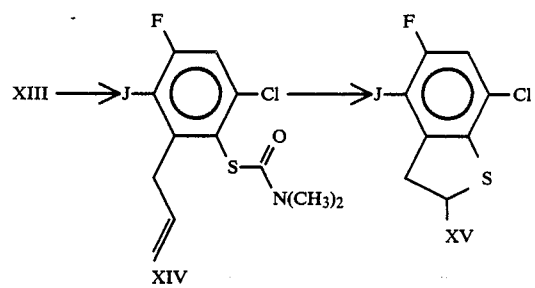

Treatment of XIV with N-bromosuccinimide in a mixture of carbon tetrachloride and chloroform at about 0° C. to room temperature affords the bromide XVI. Reaction of XVI with a mixture of acetic acid and sodium acetate at refluxing temperature gives the acetate derivative XVII, as outlined in Scheme IX.

Scheme IX

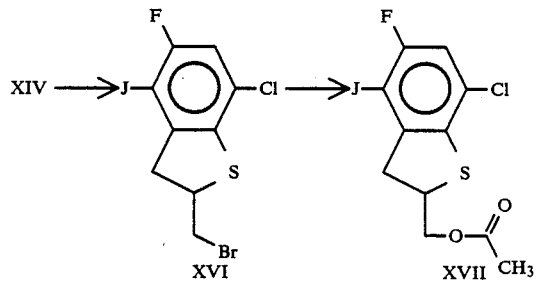

Hydrolysis of XVII, for example with refluxing aqueous ethanolic hydrogen chloride or treatment of XVI with dimethylsulfoxide containing traces of moisture at about 80°–110° C. results in the formation of the alcohol derivative XVIII as outlined in Sheme X.

Scheme X

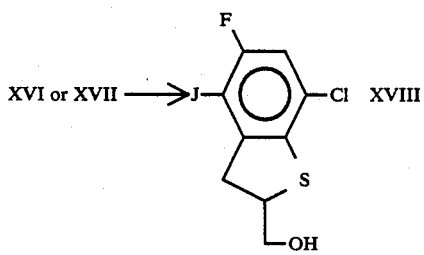

Oxidation of XVIII, for example with a mixture consisting of pyridinium dichromate, acetic anhydride, and tert-butanol in an inert solvent as previously described would afford the tert-butyl ester XIX, where $R_4=C(CH_3)_3$. Hydrolysis of the tert-butyl ester may be achieved for example with trifluoroacetic acid as described above to produce the carboxylic acid XX, where $R_4=H$. Esterification of XX with diazomethane in methylene chloride at 0° C. would afford methyl ester XXI, where $R_4=CH_3$. This is outlined in Scheme XI.

Scheme XI

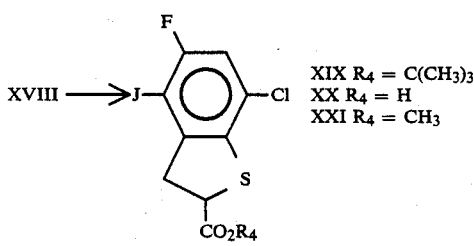

XIX $R_4 = C(CH_3)_3$
XX $R_4 = H$
XXI $R_4 = CH_3$

Compounds of Formula I wherein $R_3$ is one of the defined functional moieties can be prepared by treatment of an appropriate compound of Formula I by conventional procedures and reagents, as illustrated in the Examples, hereinafter. Thus, various subclasses of compounds of formulae I can be prepared as follows from precursors wherein $R_3$ is —$CH(R_2)$—OH.

Compounds wherein $R_3$ is —$CH(R_2)$—OH, (1) upon treatment with a carboxylic acid anhydride or acid chloride produce an ester, $CHR_2OC(O)R_4$; (2) by treatment of the alcohol with an alkylsulfonyl chloride produce a sulfonate, $CHR_2OSO_2(C_1-C_4 \text{ alkyl})$; or (3) treatment of the alcohol with cyanic acid, an isocyanate, or a carbamoyl chloride produce carbamates, $CHR_2OC(O)N(R_2)_2$, $CHR_2OC(O)N(R_2)OCH_3$, and $CHR_2OC(O)N(R_2)Ph$.

Compounds wherein $R_3$ is —$C(R_2)=NO(R_6)$ also may be prepared by conventional procedures: oxidation of an appropriate compound of Formula I wherein $R_3$ is —$CH(R_2)OH$ with a mixture of oxalyl chloride, dimethylsulfoxide and triethylamine, according to the procedure reviewed by A. J. Mancuso and D. Swern, *Synthesis.* 165 (1981), to form an aldehyde or ketone wherein $R_3$ is —$C(O)$—$(R_2)$, which can be subsequently treated with a hydroxylamine to form the oxime, (—$C(R_2)=NOR_6$).

The aldehyde, upon treatment with methylene triphenylphosphorane in a suitable inert solvent such as dimethylsulfoxide or benzene at about 0° C. to 70° C., produces the olefin wherein $R_3$ is $CH=CH_2$. Such Wittig-type reactions are reviewed in A. Maercker, *Org. React.*, 14, 270 (1965) and H. House, "Modern Synthetic Reactions", Benjamin, Menlo Park, Calif., 1972, pp. 682–709.

Compounds wherein $R_3$ is —$C(O)$—$O(R_4)$, —$C(O)N(R_4)(R_2)$, —$C(O)Cl$ or —$CN$ can be prepared by conventional treatment of an alcohol, —$CH(R_2)$—OH where $R_2$ is hydrogen, with Jones' reagent or pyridinium dichromate to give the corresponding carboxylic acid, $R_3$ is —$C(O)OH$. Alternatively, oxidation of the alcohol, where $R_2$ is hydrogen, with pyridinium dichromate in the presence of tert-butanol and acetic anhydride in an inert solvent such as methylene chloride at about 0° C. to 40° C. as described by E. J. Corey and B. Samuelsson, *J. Org. Chem.*, 49, 4735 (1984), affords the tertiary butyl ester, $R_3=CO_2C(CH_3)_3$. Hydrolysis of the tert-butyl ester with trifluoroacetic acid at about 0° C. to 50° C. provides the carboxylic acid, $R_3$ is $CO_2H$. The carboxylic acid which can be converted to a salt, or to an ester $CO_2R_4$, or to an amide —$C(O)N(R_4)(R_2)$, by treatment of the acid with thionyl chloride to form the acid chloride ($R_3$=—$C(O)Cl$) and treatment of the acid chloride with an appropriate alcohol $R_4$—OH or amine H—$N(R_4)(R_2)$, respectively. Treatment of the acid chloride with ammonia produces the unsubstituted amide, which is dehydrated by conventional procedures to the nitrile, $R_3$=—$CN$. Treatment of the acid chloride with the lithium dianion of methyl phenyl sulfone in tetrahydrofuran (THF), conversion of the resultant intermediate to the corresponding O,O-diphenylenol phosphate derivative, and reduction with sodium in a liquid ammonia-THF solution affords the acetylene derivative, where $R_3$ is $C\equiv CH$. Such procedures are described by P. A. Bartlett et al., *J. Am. Chem. Soc.*, 100, 4852 (1978).

Compounds wherein $R_3$ is $C(R_2)(R_7)CN$ are prepared by treating an appropriate compound of Formula I wherein $R_3$ is —$CH(R_2)OH$, with mesyl chloride to form the mesylate, and treating the mesylate with potassium cyanide.

Compounds wherein $R_3$ is $C_1-C_4$ haloalkyl are prepared by treating an appropriate compound of Formula I wherein $R_3$ is —$CH(R_2)OH$ with a carbon tetrahalide derivative in the presence of triphenylphosphine in an inert solvent such as methylene chloride following the procedures of P. J. Kocienski et al., *J Org. Chem.*, 42, 353 (1977).

Compounds of Formula I can also be prepared by the following general methods:

$J=J-1$, $J-2$ in addition to the methods already described, these compounds can be prepared by treating an appropriate phthalic or tetrahydrophthalic anhydride with an appropriate aniline, by fusing the two reagents at a temperature of 120°–220° C., or by refluxing a mixture of the reagents in a solvent such as acetic acid, toluene or xylene. The reaction can be catalyzed in xylene or toluene by an amine such as triethylamine or DBU (1,8-diazabicyclo[5.4.0]undec-7-ene). The products wherein one or both of X and Y is (are) sulfur can be prepared by treating (i.e., thionating) a product wherein X and Y are both oxygen with phosphorus pentasulfide or Lawesson's Reagent (2,4-bis-(4-methoxyphenyl)-1,3-dithia-2,4-diphosphetane-2,4-disulfide), in an inert solvent such as benzene, toluene, xylene or chloroform at room temperature to reflux temperature, according to the method of S. O. Lawesson et al., *Nouv. J. Chim.*, 4, 47 (1980).

J=J-3: such are prepared by reacting 3,4,5,6-tetrahydrophthalic anhydride with an appropriate aniline in an inert solvent such as tetrahydrofuran or toluene to give an intermediate acid-amide. The resulting intermediate is dehydrated with DCC (1,3-dicyclohexylcarbodiimide) or like dehydrating/condensation agent Reference: U.S. Pat. No. 4,472,190.

J=J-4, Z=nitrogen, X=O, Y=O or S: 1-(ethoxycarbonyl)piperidazine is treated with an iso(thio)cyanate prepared from an appropriate aniline by conventional methods, and treating the resulting intermediate product with sodium hydride. Alternatively, an appropriate N-(alkoxycarbonyl)hydrazine is treated with an appropriate iso(thio)cyanate, and the resulting intermediate is cyclized with a base to provide a urazole. Alkylation of the disodium salt of the urazole with 1,4-dibromobutane or 1,5-dibromopentane yields the desired product. Reference: European Pat. No. 104484; German Offenlegungschrift No. 3,504,051. J-4 compounds wherein Z=carbon, X=O or S, Y=O: ethyl pipecolinate is treated with the iso(thio)cyanate prepared from the appropriate aniline, in an inert solvent, such as THF, and the resulting (thio)urea intermediate is treated with ethanolic hydrogen chloride at reflux. Reference: U.S. Pat. No. 4,560,752. Thionation as described for J=J-1, provides those compounds wherein both X and Y=S.

J=J-5: these are prepared by methods analogous for those described for J=J-4, Z=carbon except that the (thio)urea intermediate is treated with either aqueous hydrochloric acid or sodium methoxide in methanol. Reference: European Pat. No. 70,389.

J=J-6: an appropriate aniline is diazotized and coupled with pipecolinic acid in the presence of triethylamine. Reference: U.S. Pat. Nos. 4,599,104; 4,002,636; 3,939,174.

J=J-7: an appropriate aniline is diazotized, and the product is reduced with stannous chloride to give a phenylhydrazine. The phenylhydrazine or its corresponding hydrochloride salt are condensed with a 2-(alkoxycarbonyl)cycloalkanone in an inert solvent such as toluene or ethanol, optionally in the presence of a basic catalyst such as triethylamine or sodium acetate, to afford an intermediate 4,5-fused-2,3-dihydropyrazol-3-one derivative. The intermediate is halogenated with phosphorous oxychloride or phosphorous oxybromide, optionally in the presence of a dehydrohalogenating agent such as N,N-diethylaniline at about 130°–160° C. to provide J-7 where $R_9$ is bromine or chlorine. Preparation of such compounds, and those wherein $R_9$ is other than halogen, is described in U.S. Pat. Nos. 4,059,434; 4,124,373, and European Pat. No. 138,527.

J=J-8: an appropriate aniline is converted to a phenylhydrazine, which is treated with 6-(hydroxyimino)-1-morpholinocyclohexene, and the resulting product is oxidized with cupric sulfate in pyridine. Reference: European Pat. No. 142,769.

J=J-9: an appropriate aniline is converted to a phenylhydrazine, which is treated with an acyl halide to form the acylhydrazide, which is treated with trichloromethyl chloroformate or phosgene, optionally in the presence of triethylamine. Reference: U.S. Pat. No. 3,385,862.

J=J-10: an appropriate aniline is converted to a phenylhydrazine hydrochloride salt, which is condensed with a cyclic iminoether derivative in an inert solvent such as tetrahydrofuran at about 25° C. to 67° C. to produce an amidrazone hydrochloride salt. The amidrazone is treated with thiophosgene, optionally in the presence of a base such as triethylamine, in an inert solvent such as dioxane at 80° C. to 105° C. to afford J-10 where X is sulfur. Alternatively, the amidrazone is treated with phosgene or trichloromethyl chloroformate, optionally in the presence of triethylamine, in an inert solvent such as dioxane at 80° C. to 105° C. to afford J-10 where X is oxygen. Reference: U.S. Pat. No. 4,213,773.

J=J-11: an iso(thio)cyanate prepared from the appropriate aniline is treated with trimethylsilyl azide ($R_{10}$ is hydrogen), which may be alkylated by conventional means. Reference: WIPO Pat. No. WO 85/01939 and EP-A No. 161, 304.

J=J-12: an appropriate aniline is diazotized and treated with malonyldiurethane. The resulting product is cyclized by treatment first with ethanolic potassium hydroxide in THF, then with aqueous hydrochloric acid to give a triazinedionecarboxylic acid, which is decarboxylated in the presence of mercaptoacetic acid and xylene to give J-12 wherein $R_{10}$ is hydrogen. Alternatively, an appropriately substituted aniline is diazotized and coupled with N-cyanoacetylurethane to afford an ethyl N-((aryl)cyanoacetyl) carbamate, which is cyclized in refluxing xylene in the presence of molecular sieves to remove ethanol. The resulting triazinedione-carbonitrile intermediate is then hdrolyzed with refluxing hydrochloric acid, and the resulting carboxylic acid is decarboxylated at 200°–250° C., optionally in the presence of an inert solvent such as Dowtherm ®, to produce J-12 where $R_{10}$ is hydrogen. alkylation of J-12 where $R_{10}$ is hydrogen is effected by reaction with sodium hydride and an alkyl halide in a suitable inert solvent such as DMF at about 0° C. to room temperature to afford J-12 wherein $R_{10}$ is one of the defined moieties. Reference: PCT application No. WO 86/00072. The patent also describes other suitable methods.

J=J-13: these are prepared by treating tetrahydrohomophthalic acid (2-carboxycyclohexene-1-acetic acid: (R. Grewe and A. Mondon, Chemische Berichte, volume 81, pages 279–286 (1948)), at page 283) with an appropriate aniline in refluxing acetic acid solvent.

J=J-14: an isocyanate prepared from an appropriate aniline is treated with sarcosine methyl ester hydrochloride in the presence of triethylamine, followed by treatment of the resulting urea with aqueous ethanolic hydrogen chloride. Reference: U.S. Pat. No. 4,560,752.

J=J-15: an appropriate aniline is converted to a phenylhydrazine, which is condensed with an α-ketoacid to form a hydrazone. The hydrazone is treated with diphenylphosphoryl azide in the presence of triethylamine in refluxing toluene to give a J-15 compound wherein $R_8$ is one of the defined moieties other than chlorine and $R_{10}$ is hydrogen. Alkylation of J-15 where $R_{10}$ is hydrogen is effected by reaction with sodium hydride and an alkyl halide in an inert solvent such as THF at about 0° C. to room temperature to produce J-15 wherein $R_{10}$ is one of the defined moieties. References: U.S. Pat. Nos. 4,213,773; 4,315,767; WIPO Pat. No. WO 85/01637.

An appropriate aniline or isocyanate reagent can be prepared from a compound of Formula I, wherein J is other than one of those defined herein, prepared by methods described herein. In such a case, the moiety J might appropriately be one of benzhydrylamino, benzoylamino or acetylamino, benzylamino, allylamino and trichloroacetylamino. As is shown in the examples, the aniline or isocyanate can be prepared from the J compound by conventional means.

It is to be understood that the following classes of compounds are novel and constitute aspects of this invention:

(1) Compounds of Formula I, including those wherein J is one of J-1 through J-15, those wherein J is one of the moieties described in the paragraph immediately above, and those wherein J is amino (—$NH_2$) or isocyanato (—NCO);
(2) Compounds of Formula II;
(3) Compounds of Formula III;
(4) Compounds of Formula IV;
(5) Compounds of Formula V;
(6) Compounds of Formula VI;
(7) Compounds of Formula IIA;
(8) Compounds of Formula XII;
(9) Compounds of Formula XIII;
(10) Compounds of Formula XIV;
(11) Compounds of Formula XV;
(12) Compounds of Formula XVI;
(13) Compounds of Formula XVII;
(14) Compounds of Formula XVIII;
(15) Compounds of Formula XIX;
(16) Compounds of Formula XX;
(17) Compounds of Formula XXI.

The preparation, isolation and testing of typical individual species of the compounds of Formulae I are described in the examples, following. The genus of compounds is further illustrated and exemplified by the following further individual species in Tables 1 to 21, all of which are specifically contemplated in this invention. In the interest of brevity, and clarity, and to avoid repetition of long chemical names, these species will be identified in terms of Formula I and the other symbols used therein.

The following examples further exemplify the invention. In each case, the identity of each product, and each of any intermediate involved, was confirmed by appropriate chemical and spectral analyses.

EXAMPLE 1

N-(2,3-dihydro-2-methyl-6-benzofuranyl)-3,4,5,6-tetrahydrophthalimide

A mixture of 25.0 g of 3,4,5,6-tetrahydrophthalic anhydride (THPA), 17.9 g of 3-aminophenol and 350 mL of glacial acetic acid was refluxed for 1 hour, then cooled and poured slowly into 1400 mL of ice-water. The resulting mixture was filtered. The collected solids were washed with cold water and dried (oven, reduced pressure) to give N-(3-hydroxyphenyl)-3,4,5,6-tetrahydrophthalimide (1A), as yellow crystals, m.p.: 196°–197.5° C.

3.0 g of powdered potassium carbonate, then 2.6 g of allyl bromide were added to a stirred suspension of 5.0 g of 1A in 25 mL of acetone. The mixture was refluxed for 1 hour, then stirred overnight at room temperature. The solvent was evaporated, water was added to the residue and the pH of the mixture was adjusted to 11 by addition of 10% aqueous sodium hydroxide. The resulting mixture was extracted with ethyl acetate, the extract was washed with brine and dried ($Na_2SO_4$), the solvent was evaporated and the residue was flash chromatographed on silica gel with a 1:9 v:v mixture of ethyl acetate and hexane as eluent to give N-(3-allyloxyphenyl)-3,4,5,6-tetrahydrophthalimide (1B), as yellow crystals, m.p.: 88°–90° C.

1 g of 1B was heated on an oil bath at 200°–210° C. for 5 hours and the product was flash chromatographed on silica gel with a 1:4 v:v mixture of ethyl acetate and hexane as eluent. Two products were isolated, N-(4-allyl-3-hydroxyphenyl)-3,4,5,6-tetrahydrophthalimide (1C), as yellow crystals, m.p.: 147°–148° C. and N-(2-allyl-3-hydroxyphenyl)-3,4,5,6-tetrahydrophthalimide (1D), as a white solid, m.p.: 72°–75° C.

A mixture of 0.20 g of 1C, 100 mg of p-toluenesulfonic acid (PTSA), and 10 mL of xylene was refluxed for 24 hours, then cooled and poured into a saturated aqueous solution of sodium bicarbonate. The resulting mixture was extracted with ethyl acetate, and the extract was washed in succession with sodium bicarbonate solution, water and brine, dried ($Na_2SO_4$) and filtered. The solvent was evaporated and the residue was chromatographed on a Chromatotron ™ plate, starting with a 3:17 v:v mixture of ethyl acetate and hexane as eluent and gradually increasing the ethyl acetate content in the eluent, to give the title compound, as yellow crystals, m.p.: 114°–118° C.

EXAMPLE 2

N-(2,3-dihydro-2-methyl-4-benzofuranyl)-3,4,5,6-tetrahydrophthalimide

Example 2 was prepared, as a yellow oil, by treating 0.48 g of 1D with PTSA in xylene according to the procedures described in Example 1.

EXAMPLE 3

N-(7-chloro-2,3-dihydro-2-methyl-4-benzofuranyl)-3,4,5,6-tetrahydrophthalimide

A mixture of 7.4 g of 2-chloro-5-nitrophenol, 5.4 g of allyl bromide, 5.9 g of anhydrous potassium carbonate and 50 mL of dry N,N-dimethylformamide (DMF) was stirred at room temperature over a weekend. Then the mixture was poured into water, and the resulting mixture was extracted twice with ethyl acetate and twice with ether. The combined extracts were washed with water, then with brine, dried ($Na_2SO_4$), filtered and stripped of the solvents. The residue was recrystallized from hexane to give 1-(allyloxy)-2-chloro-5-nitrobenzene (3A), as orange needles, m.p.: 58°–59.5° C.

A suspension of 1.0 g of 3A and 5.3 g of stannous chloride dihydrate in 10 mL of absolute ethanol was heated for 1 hour. The resulting mixture was poured into 100 g of ice, then sufficient 10% aqueous sodium hydroxide solution was added, with stirring, to bring the pH of the mixture to 10. The mixture was extracted with ethyl acetate, then with ether. The combined extracts were washed with water, then brine, then dried ($Na_2SO_4$) and stripped of the solvents, to give 3-(allyloxy)-4-chloroaniline (3B), as a brown oil.

A mixture of 4.4 g of THPA, 5.3 g of 3B and 60 mL of glacial acetic acid was refluxed for 1 hour, then poured into 300 mL of ice water. The resulting mixture was allowed to stand for 10 minutes, then filtered. The collected solid was washed with cold water, dried under reduced pressure and recrystallized from ethyl acetate/hexane, to give N-(3-(allyloxy)-4-chlorophenyl)-3,4,5,6-tetrahydrophthalimide (3C), as yellow crystals, m.p.: 118.5°–120° C.

7.2 g of 3C was heated at 210° C. for 1.5 hours, then the product was cooled and flash chromatographed on silica gel, with a 1:5 v:v mixture of ethyl acetate and hexane as eluent, to yield a viscous yellow oil that solidified on standing to give N-(2-allyl-4-chloro-3-hydroxyphenyl)-3,4,5,6-tetrahydrophthalimide (3D), m.p.: 80°-82.5° C.

The title compound was prepared, as yellow crystals, m.p.: 134°-137° C., from 3D by the procedures described in Example 1.

EXAMPLE 4

N-(7-chloro-2,3-dihydro-2-(hydroxymethyl)-4-benzofuranyl)-3,4,5,6-tetrahydrophthalimide A solution of 1.50 g of 80% m-chloroperbenzoic acid (MCPBA) in 20 mL of 1,2-dichloroethane was added dropwise to a solution of 2.0 g of 3D in 25 mL of 1,2-dichloroethane at room temperature. The resulting mixture was heated at 70° C. for four hours, cooled and extracted with saturated aqueous sodium sulfite solution, until no reaction to starch/iodide paper occurred. The organic phase was separated, washed with saturated aqueous sodium bicarbonate solution, water, brine, dried (Na$_2$SO$_4$) and stripped of solvent. The residue was flash chromatographed over silica gel, with a 2:3 v:v mixture of ethyl acetate and hexane as eluent, to obtain the title compound, as yellow crystals, m.p.: 193°-195° C.

EXAMPLE 5

N-(2,3-dihydro-2,7-dimethyl-4-benzofuranyl)-3,4,5,6-tetrahydrophthalimide

N-(2-allyl-3-hydroxy-4-methylphenyl)-3,4,5,6-tetrahydrophthalimide (5A) was prepared, as yellow crystals, m.p.: 141°-143° C., from 2-methyl-5-nitrophenol and allyl bromide by the procedures described in Example 3 for preparing 3D from 2-chloro-5-nitrophenol and allyl bromide.

The title compound was prepared, as yellow crystals, m.p.: 158°-160° C., from 5A, according to the procedure described in Example 1.

EXAMPLE 6

N-(2,3-dihydro-2-(hydroxymethyl)-7-methyl-4-benzofuranyl)-3,4,5,6-tetrahydrophthalimide The title compound was prepared, as yellow crystals; m.p.: 177°-179° C., from 5A, by the procedures described in Example 4.

EXAMPLE 7

N-(2-((allyloxyimino)methyl)-7-chloro-2,3-dihydro-4-benzofuranyl)-3,4,5,6-tetrahydrophthalimide A solution of 40 microliters of oxalyl chloride in 4 mL of methylene chloride was stirred under argon at −60° C. 65 microliters of dimethyl sulfoxide was added, and the mixture was stirred for 10 minutes. A solution of 0.1 g of Example 4 in 4 mL of methylene chloride was added and the mixture was stirred for 30 minutes. 0.28 mL of triethylamine was added and the mixture was allowed to warm to room temperature. 4 mL of dry pyridine and 40 mg of allyloxyamine hydrochloride were added and the mixture was stirred at room temperature for 1.5 hours. The solvents were removed by distillation with toluene; the residue was dissolved in ethyl acetate, the solution was filtered and the filtrate was chromatographed on a Chromatotron ™ plate; by using initially a 1:9 v:v mixture of ethyl acetate and hexane as eluent and gradually increasing the ethyl acetate content; the title compound was obtained, as a yellow oil.

EXAMPLE 8

N-(2-(acetoxymethyl)-7-chloro-2,3-dihydro-4-benzofuranyl)-3,4,5,6-tetrahydrophthalimide The title compound, the acetic acid ester of Example 4, was obtained as a yellow glass, by treating Example 4 with acetic anhydride in the presence of 4-(dimethylamino)pyridine (DMAP) and pyridine.

EXAMPLE 9

N-(2-carboxy-7-chloro-2,3-dihydro-4-benzofuranyl)-3,4,5,6-tetrahydrophthalimide

The alcohol, from Example 4, was converted to the title acid, which was obtained as a beige solid, m.p.: 215°-217° C., by treating the alcohol with Jones' Reagent.

EXAMPLE 10

N-(2-(bromomethyl)-7-chloro-2,3-dihydro-4-benzofuranyl)-3,4,5,6-tetrahydrophthalimide 1.67 g of Example 4 was dissolved in a minimum amount of methylene chloride. 2.07 g of carbon tetrabromide was added, then the solution was stirred under nitrogen at 5° C. while 2.0 g of triphenylphosphine was added in portions over 10 minutes. The mixture was stirred for 10 minutes in an ice bath, then for 4 hours at room temperature. The solvent was evaporated; the residue was triturated with a 9:1 v:v mixture of ether and hexane. The supernatant liquid was decanted and stripped of solvent and the residue was flash chromatographed on silica gel, by using a 1:4 v:v mixture of ethyl acetate and hexane as eluent, to give the title compound, as white crystals, m.p. 134°-136° C.

EXAMPLE 11

N-(2-(tert-butoxycarbonyl)-2,3-dihydro-7-chloro-4-benzofuranyl)-3,4,5,6-tetrahydrophthalimide 0.33 g of Example 4 was dissolved in a minimum amount of methylene chloride. 1.5 g of tert-butyl alcohol, 1.0 mL of acetic anhydride and 0.75 g of pyridinium dichromate were added, and the mixture was stirred for 1 hour at room temperature. The mixture was flushed through silica gel, the column was rinsed with methylene chloride, the solvent was evaporated and the residue was chromatographed on silica gel, by using a 1:4 mixture of ethyl acetate and hexane as eluent, to give the title compound, as a yellow glass.

EXAMPLE 12

The acetic acid ester of Example 6 was obtained as a yellow solid, m.p.: 130°-132° C., by treating Example 6 with acetic anhydride in the presence of DMAP and pyridine.

EXAMPLES 13 AND 14

The methyl ester—i.e., Example 13, obtained as a yellow solid, m.p.: 121°-123° C.—and the ethyl ester—i.e., Example 14, obtained as a yellow solid, m.p.: 71°-76° C.—were prepared by treating Example 9 with methanol and ethanol, respectively, in the presence of PTSA.

EXAMPLES 15 AND 16

The ammonium salt—i.e., Example 15, obtained as a white powder, m.p.: 197°-198° C. (with decomposition)—and the isopropylamine salt—i.e., Example 16, obtained as a tan solid, m.p.: 211°–213° C. (with decomposition)—of Example 9 were prepared by treating Example 9 with ammonia gas and isopropylamine, respectively.

EXAMPLE 17

The sodium salt of Example 9 was prepared, as a yellow powder, m.p.: 280°–28° C. (with decomposition) by treating Example 9 in ethanol with a water solution of sodium bicarbonate.

EXAMPLE 18

The alcohol of Example 6 was converted to the acid, Example 19, obtained as a tan solid, m.p.: 229°–231° C. (with decomposition) by treating the alcohol with Jones' reagent.

EXAMPLE 19

N-(7-Chloro-2,3-dihydro-5-fluoro-2-methyl-4-benzofuranyl)-3,4,5,6-tetrahydrophthalimide 3-(allyloxy)-4-chloro-6-fluoroaniline (19A) was prepared, as a brown oil, from 2-chloro-4fluorophenol and allyl bromide by procedures described in U.S. Pat. No. 4,452,981.

A mixture of 9.0 g of 19A, 6.8 g of THPA and 100 mL of glacial acetic acid was heated at reflux temperature for 4 hours. The resulting mixture was cooled to room temperature, poured into 450 mL of water and extracted with ether. The extract phase was washed with water, dried ($Na_2SO_4$), and filtered, and the solvent was evaporated from the filtrate. The residue was flash-chromatographed on silica gel, with a 15:85 v:v mixture of ethyl acetate and hexane as eluent, to give N-(3-(allyloxy)-4-chloro-6-fluorophenyl)-3,4,5,6-tetrahydrophthalimide (19B), as an orange oil.

9.8 g of 19B was heated in an oil bath at 200° C. for one hour. The resulting crude product was cooled to room temperature and flash chromatographed on silica gel, by using a 5:95 v:v mixture of acetone and toluene as solvent, to give N-(2-allyl-4-chloro-6-fluoro-3-hydroxyphenyl)-3,4,5,6-tetrahydrophthalimide (19C), as a tan solid, m.p.: 109°–111° C.

A mixture of 80 mL of xylene and 0.5 g of PTSA monohydrate was dehydrated by azeotroping for 30 minutes. The resulting solution was cooled to room temperature, 1.70 g of 19C was added and the resulting mixture was heated at reflux for 18 hours, then held at room temperature overnight. The mixture was washed with a saturated aqueous solution of sodium bicarbonate, then with water, then with brine, dried ($Na_2SO_4$), filtered and stripped of solvent. The residue was flash-chromatographed on silica gel, using a 1:4 v:v mixture of ethyl acetate and hexane as eluent, to give the title compound, as off-white crystals, m.p.: 169°–171° C.

EXAMPLE 20

N-(7-Chloro-2,3-dihydro-5-fluoro-2-(hydroxymethyl)-4-benzofuranyl)-3,4,5,6-tetrahydrophthalimide A solution of 0.67 g of 19C and 475 mg of 80% MCPBA in 15 mL of 1,2-dichloroethane was heated on an oil bath at 70° C. for 2.5 hours. A few milligrams of PTSA was added, the mixture was cooled to room temperature, washed with a saturated aqueous solution of sodium sulfite, followed by a saturated aqueous solution of sodium bicarbonate, dried ($Na_2SO_4$), filtered and stripped of solvent. The residue was flash chromatographed on silica gel with a 40:60 v:v mixture of ethyl acetate and hexane as eluent, to give the title compound, as white crystals, m.p.: 193°–195° C.

EXAMPLE 21

N-(2-(acetoxymethyl)-7-chloro-2,3-dihydro-5-fluoro-4-benzofuranyl)-3,4,5,6-tetrahydrophthalimide The title compound, the acetic acid ester of Example 20, was obtained, as off-white crystals, m.p.: 129°–131° C., by treating Example 20 with acetic anhydride in the presence of DMAP and pyridine.

EXAMPLE 22

N-(2-carboxy-7-chloro-2,3-dihydro-5-fluoro-4-benzofuranyl)-3,4,5,6-tetrahydrophthalimide The title compound was obtained, as a white powder, m.p.: 209°–211° C. (with decomposition) by treating Example 20 with Jones' Reagent.

EXAMPLE 23

N-(7-chloro 2,3-dihydro-5-fluoro-2-(methoxycarbonyl)-4-benzofuranyl)-3,4,5,6-tetrahydrophthalimide The title compound was prepared, as a yellow semi-solid, by treating Example 22 with methanol in the presence of PTSA.

EXAMPLE 24

N-(7-chloro-2,3-dihydro-2-((1-ethoxycarbonyl)ethoxycarbonyl)-5-fluoro-4-benzofuranyl)-3,4,5,6-tetrahydrophthalimide A mixture of 0.300 g of Example 22, 120 microliters of ethyl 2-bromopropionate, 0.136 g of potassium carbonate, 0.136 g of potassium iodide and 8 mL of acetonitrile was heated at reflux for 3 hours. The resulting mixture was partitioned between ether and water; the ether phase was separated, washed with water, then brine, dried ($MgSO_4$), filtered and stripped of solvent. The residue was flash chromatographed on silica gel, by using a 1:3 v:v mixture of ethyl acetate and hexane as eluent, to give the title compound, as a yellow semi-solid.

EXAMPLE 25

N-(7-chloro-2,3 dihydro-2-(hydroxymethyl)-4-benzofuranyl)phthalimide

The title compound was prepared, as a white solid, m.p.: 181°–183° C., from 3B and phthalic anhydride in three steps, according to the procedures described for preparing Example 4 from 3D.

EXAMPLE 26

N-(2-carboxy-7-chloro-2,3-dihydro-4-benzofuranyl)phthalimide was prepared as beige crystals, m.p.: 236°–239° C. (with decomposition) by treating Example 25 with Jones' Reagent.

EXAMPLES 27–30

By procedures described in the foregoing examples, the following compounds of Formula I were prepared Example 27, the ethyl ester of Example 26, as a yellow solid, m.p.: 134°–136° C.;

Example 28, the methyl ester of Example 26, as a yellow solid, m.p.: 136°–138° C.;

Example 29, the sodium salt of Example 26, as a yellow solid, m.p.: not determined (decomposition above 300° C.);

Example 30, the ammonium salt of Example 26, as a yellow powder, m.p.: 220°-223° C. (with decomposition).

EXAMPLE 31

N-(7-chloro-2,3-dihydro-2-methyl-4-benzofuranyl)phthalimide

The title compound was prepared, as a beige solid, m.p.: 197°-198° C., from 3B and phthalic anhydride, by the procedures described for preparing Example 3 from 3B.

EXAMPLE 32

2-(7-Chloro-2,3-dihydro-2-methyl-4-benzofuranyl-4-methyl-3,5-dioxo-1,2,4-triazine-3,5(2H,4H)-dione 15 g of hydrazine was added to a mixture of 30 g of Example 31 and 120 mL of dimethyl sulfoxide under nitrogen at room temperature. The mixture was stirred for 16 hours, then was added to 600 mL of water. The mixture was extracted with ether, the extract was washed with water, then with brine, dried and stripped of solvent to give 4-amino-7-chloro-2,3-dihydro-2-methylbenzofuran (32A), as a solid, m.p.: 70° C.

A mixture of 9.18 g of 32A, 10 mL of 12N hydrochloric acid and 10 mL of water was heated on a steam bath for 1 hour, then 10 mL of water was added and the mixture was stirred at room temperature overnight. Then 30 mL of water was added, the mixture was cooled to 0° C. and stirred while a solution of 3.45 g of sodium nitrite in 10 mL of water was added dropwise over 15 minutes, then was stirred for 1 hour at 0° C. The resulting mixture was added slowly to a stirred mixture of 7.8 g of N-cyanoacetylurethane, 35 mL of pyridine and 900 mL of water, at 0° C. The resulting mixture was stirred at 0° C. for 1.5 hours, and filtered. The collected solid phase was washed with water, dried under reduced pressure and recrystallized from acetone/petroleum ether to give ethyl N-((7-chloro-2,3-dihydro-2-methyl-4-benzofuranylhydrazono)cyanoacetyl)carbamate (32B), as a solid, m.p.: 175°-177° C. (with decomposition).

A mixture of 12.5 g of 32B and 600 mL of xylene was stirred at reflux temperature overnight under a Soxhlet extractor filled with 4A molecular sieves to collect the alcohol that was formed. The mixture was cooled to room temperature and filtered; the solid product was dried under reduced pressure to give 2-(7-chloro-2,3-dihydro-2-methyl-4-benzofuranyl)-2,3,4,5-tetrahydro-3,5-dioxo-1,2,4-triazine-6-carbonitrile (32C) as a tan solid, m.p.: 244°-245° C.

A mixture of 9.0 g of 32C, 150 mL of p-dioxane and 100 mL of 6N hydrochloric acid was stirred at reflux temperature overnight. Then 20 mL of 12N hydrochloric acid was added and the mixture was stirred at reflux temperature for 2 hours, and stripped of solvent. The residue was dissolved in ethyl acetate, the solution was washed with water, then brine, dried (MgSO$_4$) and stripped of solvent. The residue was recrystallized from ethyl acetate/petroleum ether to give 2-(7-chloro-2,3-dihydro-2-methyl-4-benzofuranyl)-2,3,4,5-tetrahydro-3,5-dioxo-1,2,4-triazine-6-carboxylic acid (32D), as an amber solid, m.p.: 235°-236° C. (with decomposition).

A mixture of 8.0 g of 32D and 80 mL of Dowtherm ® was heated at 200°-250° C. for 2 hours, cooled to room temperature, diluted with petroleum ether and filtered. The collected solid phase was dried under reduced pressure, and recrystallized from ethyl acetate/petroleum ether to give 2-(7-chloro-2,3-dihydro-2-methyl-4-benzofuranyl)-1,2,4-triazine-3,5(2H,4H)-dione, (32E) as a tan solid, m.p.: 184°-186° C.

2.8 g of 32E was added over 15 minutes to a stirred mixture of 0.5 g of hexane-washed sodium hydride, 1.6 g of methyl iodide and 30 mL of dry DMF, under nitrogen at 0° C. When gas evolution ended (30 minutes) the mixture was stirred at room temperature for 1.5 hours, poured into ice-water, and the resulting mixture was filtered. The collected solid was dissolved in ethyl acetate; the resulting solution was washed with water, then brine, dried (MgSO$_4$) and stripped of solvent. The residue was recrystallized from ethyl acetate/hexane to give the title compound, as a tan solid, m.p.: 131°-132° C.

EXAMPLES 33

2-(7-chloro-2,3-dihydro-2-methyl-4-benzofuranyl)-4-(difluoromethyl)-5-methyl-2H-1,2,4-triazol-3(4H)-one;

5.5 g of 32A was diazotized by the procedure described in Example 32. The diazotization mixture was cooled to −25° C. and a solution of 19.7 g of tin(II) chloride dihydrate in 25 mL of 12N hydrochloric acid was added dropwise over 20 minutes to the stirred mixture, which was stirred thereafter at −25° C. for 4 hours. Then a solution of 2.82 g of redistilled pyruvic acid in 20 mL of water was added dropwise to the stirred mixture at −25° C., then while being stirred was allowed to warm slowly to room temperature and stirred over a weekend. Then the mixture was filtered, and the solid material was washed with water and dissolved in a saturated aqueous solution of sodium bicarbonate. The solution was extracted with ethyl acetate, and the aqueous phase was acidified with 12N hydrochloric acid and extracted with ethyl acetate. The latter extract was washed with water, then with brine, dried (MgSO$_4$) and stripped of solvent. The residue was recrystallized from ethyl acetate/hexane to give 2-((7-chloro-2,3-dihydro-2-methyl-4-benzofuranyl)hydrazono)propanoic acid (33A), a mixture of isomers, m.p.: 155°-157° C.

5.1 g of triethylamine was added to a stirred mixture of 5.0 g of 33A and 100 mL of toluene, then 1.9 g of diphenylphosphoryl azide was added and over two hours the mixture was heated to and held at reflux temperature. The resulting mixture was poured into 110 mL of 10% w:v aqueous ice-cold potassium hydroxide solution. Two liquid phases resulted and were separated. The aqueous phase was acidified with 12N hydrochloric acid, and extracted with ethyl acetate. The extract was washed with water, then with brine, dried (MgSO$_4$) and stipped of solvent. The residue was recrystallized from ethyl acetate/hexane to give 2-(7-chloro-2,3-dihydro-2-methyl-4-benzofuranyl)-5-methyl-2H-1,2,4-triazol-3(4H)-one (33B), as a colorless solid, m.p.: 208°-209° C.

A mixture of 0.6 g of hexane-washed sodium hydride and 30 mL of THF was saturated with Freon 22 (chlorodifluoromethane) at 0° C., then a mixture of 1.33 g of 33B and 10 mL of THF was added and the mixture was stirred at room temperature for 6 hours, Freon 22 being bubbled into the mixture throughout that period. The mixture was stirred at room temperature for a week, 15 mL of water was added dropwise, and the solvent was stripped. The residue was dissolved in ethyl acetate, the solution was washed with water, then with brine, dried (MgSO$_4$) and stripped of solvent. The residue was chromatographed on silica gel, with a 1:3 v:v mixture of hexane and methylene chloride as eluent to give the title compound, as a colorless solid, m.p.: 122.5°–123.5° C., and the isomeric 2-(7-chloro-2,3-dihydro-2-methyl-4-benzofuranyl)-1-(difluoromethyl)-5-methyl-1H-1,2,4-triazol-3(2H)-one, as a cream-colored solid, m.p.: 78°–79° C.

EXAMPLE 34

2-(7-chloro-2,3-dihydro-2-methyl-4-benzofuranyl)hexahydro-1H-imidazo[3,4-a]pyridine-1,3(2H)-dione 6.07 g of triethylamine was added to a mixture of 9.18 g of 32A, 11.87 g of trichloromethyl chloroformate and 250 mL of dioxane, and the mixture was refluxed for 6 hours. The mixture was cooled, filtered, and the filtrate was stripped of solvent, to give 7-chloro-2,3-dihydro-4-isocyanato-2-methylbenzofuran (34A), as a brown liquid.

A solution of 2.36 g of ethyl pipecolinate in 20 mL of dry THF was added, at room temperature under nitrogen, to a mixture of 2.10 g of 34A and 60 mL of dry THF, the rate of addition being such as to maintain the temperature of the mixture at 25°–32° C., then the mixture was stirred overnight at room temperature, diluted with 250 mL of hexane and filtered. The collected solid phase was identified as ethyl 1-(((7-chloro-2,3-dihydro-2-methyl-4-benzofuranyl)amino)carbonyl)-2-piperidinecarboxylate (34B), m.p.: 169°–171° C.

A mixture of 2.0 g of 34B, 25 mL of ethanol and 25 mL of 2N hydrochloric acid was stirred and refluxed for 2 hours. Then the solvent was evaporated, the residue was mixed with 50 mL of water, and the resulting mixture was extracted with methylene chloride. The extract was dried (MgSO$_4$) and the solvent was evaporated. The residue was purified by filtration through a short pad of silica gel, with a 1:1 v:v mixture ethyl acetate and hexane as eluent, to give the title compound, as a solid, m.p.: 145°–148° C.

EXAMPLE 35

3-(7-Chloro-2,3-dihydro-2-methyl-4-benzofuranyl)-1-methylimidazolidine-2,4-dione 2.30 g of sarcosine ethyl ester hydrochloride was added over 5 minutes to a mixture of 2.10 g of 34A, 1.52 g of triethylamine and 60 mL of methylene chloride, under nitrogen at 25°–30° C. The mixture was stirred at room temperature for 24 hours, then diluted with 100 mL of methylene chloride, washed with water, then brine, dried (MgSO$_4$) and stripped of solvent. The residue was dissolved in 70 mL of a 1:1 v:v mixture of ethanol and 2N hydrochloric acid. The solution was refluxed for 4 hours, the resulting mixture was stirred at room temperature overnight, stripped of volatiles, diluted with water and extracted with methylene chloride. The extract was dried (MgSO$_4$) and stripped of solvent. The residue was purified by flash chromatography over silica gel with a 1:2 v:v mixture of hexane and ethyl acetate as eluent to give the title compound, as a glass/sticky solid.

EXAMPLE 36

N-(7-Chloro-5-fluoro-2,3-dihydro-2-methyl-4-benzofuranyl)phthalimide

The title compound was prepared, as a colorless solid, m.p.: 158.5°–160° C. from 3-(allyloxy)-4-chloro-6-fluoroaniline (19A) and phthalic anhydride by the procedures described for preparing Example 19 from 19A.

EXAMPLE 37

N-(7-Chloro-5-fluoro-2,3-dihydro-2-methyl-4-benzofuranyl)-3,4,5,6-tetrahydrohomophthalimide 8.3 g of hydrazine hydrate was added to a slurry of 11.0 g of Example 36 and 60 mL of dimethyl sulfoxide under nitrogen at 25°–35° C. The mixture was stirred at room temperature for 16 hours, then added to 250 mL of water. The mixture was extracted with ether, the extract was washed with water, brine, dried (MgSO$_4$) and stripped of solvent to give 4-amino-7-chloro-4-fluoro-2,3-dihydro-2-methyl-benzofuran (37A) as a light brown oil.

A mixture of 0.61 g of 3,4,5,6-tetrahydrohomophthalic acid, 0.55 g of 37A and 10 mL of acetic acid was refluxed for 19 hours and cooled. The solvent was removed in vacuo, the residue was purified by flash chromatography on silica gel, eluting with a 1:1 v:v mixture of ether and hexane to give the title compound as a cream colored solid, m.p. 124.5°–126.5° C.

EXAMPLE 38

5-tert-Butyl-3-(5,7-dichloro-2,3-dihydro-2-methyl-4-benzofuranyl)-1,3,4-oxadiazol-2(3H)-one 4-amino-5,7-dichloro-2,3-dihydro-2-methylbenzofuran (38A) was prepared as an orange oil in four steps from 3-(allyloxy)-4,6-dichloroaniline and phthalic anhydride by the procedures described for preparing Example 19 from 19A, followed by hydrazinolysis of the phthalimide intermediate as described for the preparation of 37A.

2.19 g of 38A was suspended in 9 mL of concentrated H$_2$SO$_4$ and 9 mL of water at −5° C. A solution of 0.69 g of sodium nitrite in 4 mL of H$_2$O was added slowly and the resulting solution was stirred at 0° C. for one hour. This solution was added slowly to a mixture of 4.51 g of tin (II) chloride in 15 mL of concentrated hydrochloric acid which was precooled to −10° C., so as to maintain −10° C. to −5° C. The mixture was slowly warmed to room temperature and stirred for 16 hours. With cooling, 50% sodium hydroxide solution was added to adjust the pH to 11. The mixture was extracted with ether. The extract was washed with water, brine, dried (M$_g$SO$_4$) and stripped of solvent to leave crude 5,7-dichloro-2,3-dihydro-4-hydrazino-2-methylbenzofuran (38B), as pale orange solid, m.p.: 59°–64° C.

To a solution of 0.73 g of 38B and 0.38 g of triethylamine in 10 mL of dry THF at 0° C under nitrogen was added a solution of 0.38 g of trimethylacetyl chloride in 2 mL of dry THF. The mixture was stirred at room temperature overnight, filtered, and evaporated. The residue was purified by flash chromatography on silica gel, using a 1:2 v:v mixture of ethyl acetate and hexane to afford the intermediate trimethylacetylphenylhydrazide (38C) as a solid, m.p.: 116°–118.5° C.

To a solution of 0.51 g of 38C and 0.32 g of trichloromethyl chloroformate in 20 mL of dry dioxane was added 0.20 g of triethylamine. The resulting mixture was refluxed under nitrogen for 7 hours, cooled to room temperature, filtered and evaporated. The residue was purified by flash chromatography on silica gel, eluting with a 1:4 v:v mixture of ethyl acetate and hexane to afford the title compound as a yellow solid, m.p.: 112°–115° C.

IR (cm$^{-1}$): 1775, 1610

NMR (CDCl$_3$, 200 MHz) δ 1.38 (s, 9H); 1.55 (d, 3H, J=6 Hz); 2.93 (dd, 1H; J TM 16, 8 Hz); 3.43 (dd, 1H; J=16, 9 Hz); 5.12 (m, 1H); 7.30 (s, 1H).

EXAMPLE 39

3-Chloro-2-(7-chloro-4-fluoro-2,3-dihydro-2-methyl-4-benzofuranyl)-4,5,6,7-tetrahydro-2H-indazole 7-chloro-4-fluoro-2,3-dihydro-4-hydrazino-2-methylbenzofuran (39A) was prepared as a low melting semisolid from 37A by diazotization and reduction with tin (II) chloride by the procedures described for preparing 38B from 38A. Reaction of 39A with hydrogen chloride gas in ether provided the corresponding arylhydrazine hydrochloride (39B) as a light brown solid, m.p.: 169°–172° C.

A mixture of 0.51 g of 39B, 0.34 g of ethyl cyclohexanone 2-carboxylate and 0.16 g of anhydrous sodium acetate in 10 mL of ethanol was refluxed under nitrogen for three days, cooled to room temperature, and the solvent was removed in vacuo. The residue was slurried in ether, filtered, and the filtrate residue was triturated with ether to afford 2-(7-chloro-4-fluoro-2,3-dihydro-2-methyl-4-benzofuranyl)-1,2,4,5,6,7-hexahydro-3H-indazol-3-one (39C) as a colorless solid, m.p.: 240°–242° C.

0.25 g of 39C was mixed with 0.14 g of phosphorous oxychloride and 0.15 g of N,N-diethylaniline and heated under nitrogen at 135°–140° C. for three hours, cooled, and diluted with ethyl acetate. The organic phase was washed with water, 10% hydrochloric acid, saturated sodium bicarbonate solution, brine, dried (MgSO$_4$) and stripped of solvent. The residue was purified by flash chromatography on silica gel, using a 1:4 v:v mixture of ether and hexane as eluent to afford the title compound as a yellow glass.

NMR (CDCl$_3$, 200 MHz) δ 1.53 (d, 3H, J=6 Hz) 1.83 (m, 4H); 2.50 (t, 2H, J=5 Hz); 2.70 (t, 2H, J=5 Hz); 2.90 (m, 1H); 3.35 (m, 1H); 5.10 (m, 1H); 7.05 (d, 1H, J=9Hz).

EXAMPLE 40

3-(7-Chloro-2,3-dihydro-2-methyl-4-benzofuranylimino)-4,5,6,7-tetrahydro-1(3H)-isobenzofuranone To a solution of 1.52 g of THPA in 10 mL of dry THF under nitrogen was added a solution of 1.84 g of 32A in 5 mL of dry THF. After 10 minutes, 50 mL of dry THF was added to facilitate stirring of the thick precipitate, and the mixture was stirred overnight. The solvent was removed in vacuo, the residue was slurried in ether/hexane, and the resultant solid was collected to give the intermediate acid - amide (40A) as a colorless solid.

2 95 g of 40A was slurried in 50 mL of benzene under nitrogen and treated with 1.81 g of 1,3-dicyclohexylcarbodiimide. After 18 hours at room temperature, the solution was diluted with 50 mL of hexane, filtered, and the solvent was removed to afford the title compound as a yellow solid, m.p.: 125°–127° C.

IR (cm$^{-1}$) 1780, 1680.

NMR (CDCl$_3$, 200 MHz) δ 6 1.55 (d, 3H, J=6 Hz); 1.85 (m, 4H); 2.42 (m, 2H); 2.55 (m, 2H); 2.85 (dd, 2H); 3.36 (dd, 1H); 5.06 (m, 1H); 6.75 (d, 1H, J=8 Hz); 7.12 (d, 1H, J=8 Hz).

EXAMPLE 41

2-(8-Chloro-6-fluoro-3,4-dihydro-2H-1-benzopyran-5-yl)-tetrahydro-1H-((1,2,4))triazolo((1,2-A)pyridazine-1,3(2H)-dione A mixture of 20.2 g of 19A and 14.8 g of phthalic anhydride in 300 mL of toluene was treated with 1.01 g of triethylamine and heated to reflux for hours with a Dean-stark trap to effect azeotropic removal of water. The toluene was removed in vacuo. the residue was dissolved in 800 mL of methylene chloride, and treated with 35 g charcoal. After filtration through celite and concentration of solvent in vacuo, the residue was recrystallized from ethanol afford N-[3-(allyloxy)-4-chloro-6-fluorophenyl]phthalimide (41A) as tan crystals, m.p.: 148°–150° C.

36.5 g of 41A was heated and stirred under a nitrogen atmosphere at 195° C for 1 hour. After cooling, methylene chloride was added and the crude product was purified by flash chromatography on silica gel, eluting with methylene chloride. Removal of solvent afforded N-[2-allyl-4-chloro-6-fluoro-3hydroxyphenyl]phthalimide (41B) as a nearly colorless solid, m.p.: 133.5°–135.5° C.

To a solution of 3.21 g of 41B dissolved in 10 mL dry THF under a nitrogen atmosphere was added dropwise over 10 minutes 9-BBN (38.7 mL of 0.5 M in THF). After 10 minutes, the solution was heated to reflux for 1 hour, cooled to 0° C, 12 mL of ethanol was added, followed by 6.45 mL of 3M aqueous sodium acetate solution. With ice-bath cooling, 6.4 mL of 30% hydrogen peroxide was added dropwise so as to maintain a temperature of about 25° C. The mixture was then heated to 55° C. for 1 hour, cooled to 10° C. and acidified to a pH of 4 with 10% hydrochloric acid. The mixture was diluted with ethyl acetate, extracted with brine, saturated sodium sulfite solution, brine, dried over MgSO$_4$ and stripped of solvent. Addition of ethanol and refrigeration afforded N-[2-(3-hydroxy)propyl-4 4-chloro-6-fluoro-3-hydroxyphenyl]phthalimide (41C) as a colorless solid, m.p.: 187°–188.5° C.

A mixture of 2.00 g of 41C and 0.54 g of PTSA•H$_2$O in 50 mL of xylene was azeotropically refluxed with a Dean-stark trap for 18 hours. The solution was treated further with 0.54 g of PTSA•H$_2$O and refluxed for 8 hours. The xylene was removed in vacuo and the residue was filtered through a pad of silica gel using methylene chloride as eluent to afford 8-chloro-6-fluoro-5-phthalimido chromane (41D) as a colorless solid, m.p.: 198°–200° C.

To a solution of 10.05 g of 41D in 60 mL of DMSO was added 7.58 g of hydrazine hydrate. The mixture was heated to 65°–75° C. for 3 hours, cooled, and poured into ice-water. The mixture was extracted with 3 portions of ether. The ether layer was extracted with water, brine, and dried over MgSO$_4$ to afford 5-amino-8-chloro-6-fluorochromane (41E) as a yellow oil which solidified on standing. m.p.: 47°–50° C.

8-chloro-6-fluoro-5-isocyamato-chromane (41F) was prepared, as a brown semisolid from 41E, trichloromethyl chloroformate, and triethylamine by the procedures described for preparing 34A from 32A. A solution of 1.06 g of 41F dissolved in 10 mL of toluene was added under nitrogen to 0.50 g of methyl hydrazinocarboxylate in 15 mL of toluene. After stirring overnight at room temperature, 50 mL of hexane was added, and the product was collected by filtration to afford methyl 2-(((8-chloro-6-fluoro-3,4-dihydro-2H-1-benzopyranyl-5-amino)carbonyl))-hydrazine carboxylate (41G) as a colorless solid, m.p.: 218°–220° C.

A mixture of 1.49 g of 41G and 0.94 g of sodium hydroxide in 8 mL of water was refluxed for 3.5 hours, cooled, acidified to a pH of 3 with concentrated hydrochloric acid, and the resultant solid was collected by filtration to give 4-(8-chloro-6-fluoro-3,4-dihydro-2H-1-benzopyran-5-yl)-1,2,4-triazolidine-3,5-dione (41H) as a colorless solid, m.p.: 271°–273° C.

A solution of 0.55 g of 41H in 10 mL of dry DMF was added under nitrogen to a slurry of 0.096 g of sodium hydride in 20 mL of dry DMF. The mixture was heated to 55° C. for 1 hour, cooled to room temperature, treated with 0.46 g of 1,4-dibromobutane, and stirred at room temperature overnight. The mixture was poured into water, extracted with ether, the extracts were washed with water, brine, dried (MgSO$_4$) and stripped of solvent. The residue was purified by flash chromatography on silica gel using a 1:2 to 1:1 v:v gradient of ethyl acetate and hexane to afford the title compound as colorless crystals, m.p.: 185°–188° C.

IR (cm$^{-1}$) 1770, 1708.

NMR (CDCl$_3$, 300 MHz) δ 6 1.92 (m, 4H); 2.02 (pentet, 2H, J=6 Hz); 2.72 (t, 2H, J=6Hz); 3.66 (m, 4H); 4.30 (t, 2H, J=5 Hz); 7.17 (d, 1H, J=8 Hz).

EXAMPLE 42

2-(5,7-Dichloro-2,3-dihydro-2-methyl-4-benzofuranyl)-5,6,7,8-tetrahydro-1,2,4-triazolo((4,3A))pyridine-3(2H)-one (5,7-dichloro-2,3-dihydro-2-methyl-4-benzofuranyl)-hydrazine hydrochloride (42A) was obtained as a pink solid, m.p.: 198°–200° C. by reaction of 38B with hydrogen chloride gas in ether.

A slurry of 0.61 g of 42A in 5 mL of dry THF was treated under nitrogen with 0.26 g of ethyl (3,4,5,6-tetrahydropyridyl)ether. The mixture was refluxed for 8 hours, cooled, an additional 0.03 g of ethyl (3,4,5,6-tetrahydropyridyl)ether was added, and refluxing was continued for 4 hours. The solvent was removed in vacuo, the residue was slurried in refluxing ether, cooled, and collected by filtration to afford (5,7-dichloro-2,3-dihydro-2-methyl-4-benzofuranyl)-2-piperidinone hydrazone hydrochloride (42B) as a hygroscopic solid, m.p. 79°–86° C.

0.44 g of triethylamine was added under nitrogen to a solution of 0.66 g of 42B and 0.45 g of trichloromethyl chloroformate in 30 mL of dry dioxane. The mixture was refluxed for 23 hours, cooled, filtered, and the filtrate residue was purified by flash chromatography on silica gel, using a 1:2 to 2:1 v:v gradient of ethyl acetate and hexane to afford the title compound as a light yellow solid, m.p.: 198°–202° C.

IR (cm-1) 1700, 1575.

NMR (CDCl$_3$, 200 MHz) δ 1.52 (d, 3H, J=6 Hz); 1.98 (m, 4H); 2.77 (m, 2H); 2.93 (m, 1H); 3.37 (m, 1H); 3.70 (m, 2H); 5.09 (m, 1H); 7.29 (s, 1H).

EXAMPLE 43

7-Chloro-5-fluoro-4(2,3,4,5,6,7-hexahydro-1,3-dioxo-1H-isoindol-2-yl)-2,3-dihydro-N,N-dimethyl-2-benzofurancarboxamide A mixture of 0.74 g of Example 22 in 10 mL of thionyl chloride was refluxed for 1 hour, cooled, stripped, and pumped under high vacuum to afford the corresponding acid chloride (43A) as a light yellow foam.

To a solution of 0.384 g of 43A in 5 mL of dry THF at 0° C. under nitrogen was added dropwise a solution of 0.17 g of dimethylamine hydrochloride and 0.24 g of triethylamine dissolved in 10 mL of dry THF. After one hour at 0° C., the mixture was stirred at room temperature for 2.5 hours, diluted with ethyl acetate, washed with 10% hydrochloric acid, water, brine, dried (MgSO$_4$) and stripped of solvent. The residue was purified by flash chromatography on silica gel, eluting with a 1:2 v:v mixture of ethyl acetate and hexane to afford the title compound as a pale yellow solid, m.p.: 190°–193° C.

IR (cm$^{-1}$): 2925, 1775, 1720, 1650.

NMR (CDCl$_3$), 200 MHz) δ 1.85 (m, 4H); 2.45 (m, 4H); 3.02 (s, 3H); 3.23 (s, 3H); 3.30 (dd, 1H, J=16, 10 Hz); 3.85 (dd, 1H, J=16, 7 Hz); 5.53 (dd, 1H, J=10, 7 hz); 7.04 (d, 1H, J=9 Hz).

Using the above disclosures, one skilled in the art may readily prepare the following compounds.

TABLE 1

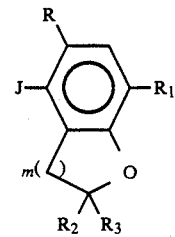

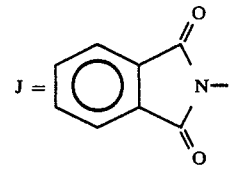

| m | R | R$_1$ | R$_2$ | R$_3$ | m.p. (°C.) |
|---|---|---|---|---|---|
| 1 | H | Cl | H | CH$_2$OH | 181–183 |
| 1 | H | Cl | H | CO$_2$H | 252–254 (dec) |
| 1 | H | Cl | H | CO$_2$C$_2$H$_5$ | 134–136 |
| 1 | H | Cl | H | CH$_3$ | 197–198 |
| 1 | H | C | H | CO$_2$CH$_3$ | 136–138 |
| 1 | H | Cl | H | CO$_2$Na | >300 (dec) |
| 1 | H | Cl | H | CO$_2$NH$_4$ | 220—223 (dec) |
| 1 | F | Cl | H | H | |
| 1 | F | Cl | H | CH$_3$ | 158.5–160 |
| 1 | F | Cl | H | CH$_2$OH | 221–213 |
| 1 | F | Cl | H | CO$_2$H | 195.5–197.5 |
| 1 | F | Cl | H | CO$_2$C(CH$_3$)$_3$ | 63–67 |
| 1 | F | Cl | H | CO$_2$CH$_3$ | 172.5–174.5 |
| 1 | Cl | Cl | H | CH$_3$ | 146.5–149 |
| 1 | Cl | Cl | CH$_3$ | | 162.5–164.5 |
| 2 | F | Cl | H | H | 198–200 |
| 2 | F | Cl | H | CH$_3$ | |
| 2 | F | Cl | CH$_3$ | CH$_3$ | |
| 2 | F | Br | H | H | |
| 2 | F | Br | H | CH$_3$ | |
| 2 | F | Br | CH$_3$ | CH$_3$ | |
| 2 | Cl | Cl | H | H | 210–212 |
| 2 | Cl | Cl | H | CH$_3$ | |

TABLE 1-continued

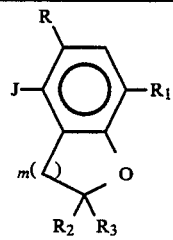

$J = $ 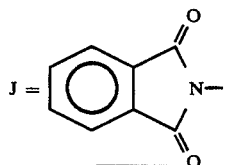

| m | R | $R_1$ | $R_2$ | $R_3$ | m.p. (°C.) |
|---|---|---|---|---|---|
| 2 | Cl | Cl | $CH_3$ | $CH_3$ | |

TABLE 2

$J = $ (hexahydroisoindole-1,3-dione group)

| m | R | $R_1$ | $R_2$ | $R_3$ | m.p. (°C.) |
|---|---|---|---|---|---|
| 1 | F | Cl | H | H | |
| 1 | F | Cl | H | $CH_2OH$ | 193–195 |
| 1 | F | Cl | H | $CH_2OC(O)CH_3$ | 129–131 |
| 1 | F | Cl | H | $CH_2OC(O)CH_2CH_3$ | oil |
| 1 | F | Cl | H | $CH_2OC(O)CH(CH_3)_2$ | oil |
| 1 | F | Cl | H | $CH_2OC(O)$ 1-methyl-cyclopropyl | oil |
| 1 | F | Cl | H | $CH_2OC(O)C(CH_3)_3$ | oil |
| 1 | F | Cl | H | $CH_2OC(O)C_6H_5$ | 127–129 |
| 1 | F | Cl | H | $CH_2OC(O)CH_2CO_2C_2H_5$ | oil |
| 1 | F | Cl | H | $CH_2OC(O)CH_2C(O)CH_3$ | glass |
| 1 | F | Cl | H | $CH_2OC(O)NHC_6H_5$ | glass |
| 1 | F | Cl | H | $CH_2OC(O)N(CH_3)OCH_3$ | glass |
| 1 | F | Cl | H | $CH_2OC(O)N(CH_3)_2$ | |
| 1 | F | Cl | H | $CH_2OC(O)CH_2Cl$ | |
| 1 | F | Cl | H | $CH_2OC(O)CH=CHCH_3$ | |
| 1 | F | Cl | H | $CH_2OC(O)\equiv CH$ | |
| 1 | F | Cl | H | $CH_2OC(O)CH=C(Cl)CH_3$ | |
| 1 | F | Cl | H | $CH_2OC(O)CH_2C_6H_5$ | |
| 1 | F | Cl | H | $CH_2OC(O)CH_2CH_2C_6H_5$ | |
| 1 | F | Cl | H | $CH_2OC(O)CH_2CH_2OCH_2CH_3$ | |
| 1 | F | Cl | H | $CH_2CH_3$ | 103.5–106.5 |
| 1 | F | Cl | H | $CH(CH_3)OH$ | 171–175 |
| 1 | F | Cl | H | $CH(CH_3)OC(O)CH_3$ | 136–139 |
| 1 | F | Cl | H | $CH_2CH_2CH_3$ | |
| 1 | F | Cl | H | $CH(C_2H_5)OH$ | |
| 1 | F | Cl | H | $CH(C_2H_5)OC(O)CH_3$ | |
| 1 | F | Cl | H | $CH_2OSO_2CH_3$ | |
| 1 | F | Cl | H | $CH_2Br$ | 126–130 |
| 1 | F | Cl | H | $CH(CH_3)Br$ | |
| 1 | F | Cl | H | $CH_2Cl$ | |
| 1 | F | Cl | H | $CH_2CH_2Cl$ | |
| 1 | F | Cl | H | $CH(CH_3)Cl$ | |
| 1 | F | Cl | H | $CH_2F$ | |
| 1 | F | Cl | H | $CH_2(CH_2)_2F$ | |
| 1 | F | Cl | H | $CH_2CN$ | |
| 1 | F | Cl | H | $CH(CH_3)CN$ | |
| 1 | F | Cl | H | $CH(NOCH_3)$ | |
| 1 | F | Cl | H | $CH(NOCH_2CH=CH_2)$ | |
| 1 | F | Cl | H | $C(O)CH_3$ | 175–177 |
| 1 | F | Cl | H | $C(NOCH_2CH=CH_2)CH_3$ | glass (syn/anti mixture) |
| 1 | F | Cl | H | $C(NOCH_2CO_2C_2H_5)CH_3$ | |
| 1 | F | Cl | H | $C(O)C_6H_5$ | |
| 1 | F | Cl | H | $CH=CH_2$ | |
| 1 | F | Cl | H | $C\equiv CH$ | |
| 1 | F | Cl | H | $COCl$ | amorphous foam |
| 1 | F | Cl | H | $CO_2H$ | 209–211(dec) |
| 1 | F | Cl | H | $CO_2CH_3$ | amorphous solid |
| 1 | F | Cl | H | $CO_2CH_2CH_3$ | 119–121 |
| 1 | F | Cl | H | $CO_2CH_2CH_2CH_3$ | glass |
| 1 | F | Cl | H | $CO_2CH(CH_3)_2$ | 55–57 |
| 1 | F | Cl | H | $CO_2(CH_2)_3CH_3$ | oil |
| 1 | F | Cl | H | $CO_2CH(CH_3)CH_2CH_3$ | glass |
| 1 | F | Cl | H | $CO_2CH_2CH_2OC_2H_5$ | 134–135.5 |
| 1 | F | Cl | H | $CO_2(CH_2)_3OH$ | glass |
| 1 | F | Cl | H | $CO_2(CH_2CH_2O)_2C_2H_5$ | oil |

TABLE 2-continued

J = 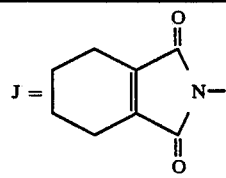

| m | R | R₁ | R₂ | R₃ | m.p. (°C.) |
|---|---|---|---|---|---|
| 1 | F | Cl | H | CO$_2$(CH$_2$CH$_2$O)$_2$H | 115-120 |
| 1 | F | Cl | H | CO$_2$(CH$_2$CH$_2$O)$_3$H | glass |
| 1 | F | Cl | H | CO$_2$(CH$_2$CH$_2$O)$_6$H | glass |
| 1 | F | Cl | H | CO$_2$C(CH$_3$)$_3$ | glass |
| 1 | F | Cl | H | CO$_2$CH$_2$CH=CH$_2$ | 104-107 |
| 1 | F | Cl | H | CO$_2$CH$_2$C(CH$_3$)=CH$_2$ | glass |
| 1 | F | Cl | H | CO$_2$CH$_2$C(Cl)=CH$_2$ | glass |
| 1 | F | Cl | H | CO$_2$CH$_2$C≡CH | 140-142 |
| 1 | F | Cl | H | CO$_2$CH$_2$C$_6$H$_5$ | 138-140 |
| 1 | F | Cl | H | CO$_2$CH$_2$CO$_2$C$_2$H$_5$ | 58-60 |
| 1 | F | Cl | H | CO$_2$CH(C$_2$H$_5$)CO$_2$C$_2$H$_5$ | stiff oil |
| 1 | F | Cl | H | CO$_2$CH(CH$_3$)CO$_2$CH$_3$ | glass |
| 1 | F | Cl | H | CO$_2$CH(CH$_3$)CO$_2$CH$_2$CH$_3$ | foam |
| 1 | F | Cl | H | CO$_2$CH$_2$CH$_2$CO$_2$CH$_3$ | glass |
| 1 | F | Cl | H | CO$_2$CH(CO$_2$C$_2$H$_5$)CH$_2$CO$_2$H$_5$ | glass |
| 1 | F | Cl | H | CO$_2$CH$_2$CH$_2$Si(CH$_3$)$_3$ | glass |
| 1 | F | Cl | H | CO$_2$CH$_2$CH$_2$Cl | |
| 1 | F | Cl | H | CO$_2$(CH$_2$)$_4$Br | |
| 1 | F | Cl | H | CN | |
| 1 | F | Cl | H | C(O)NH$_2$ | |
| 1 | F | Cl | H | C(O)NH(CH$_3$) | |
| 1 | F | Cl | H | C(O)N(CH$_3$)$_2$ | 190-193 |
| 1 | F | Cl | H | C(O)NHSO$_2$CH$_3$ | |
| 1 | F | Cl | H | C(O)NHC$_6$H$_5$ | 193-194 |
| 1 | F | Cl | H | C(O)NHCH$_2$CO$_2$C$_2$H$_5$ | 75-80 |
| 1 | F | Cl | H | C(O)NHCH(CH$_3$)CO$_2$CH$_3$ | 135-138 |
| 1 | F | Cl | H | C(O)NHCH(CH$_3$)C(O)NHCH(CH$_3$)CO$_2$CH$_3$ | foam |
| 1 | F | Cl | H | C(O)NHCH$_2$CH=CH$_2$ | |
| 1 | F | Cl | H | C(O)NHCH$_2$C≡CH | |
| 1 | F | Cl | H | C(O)N(CH$_3$)C$_6$H$_5$ | |
| 1 | F | Cl | H | C(O)NHCH(CH$_3$)C$_6$H$_5$ | |
| 1 | F | Cl | H | C(O)NH(CH$_2$)$_2$OCH$_2$CH$_3$ | |
| 1 | F | Cl | H | CH$_2$C(O)CH$_3$ | |
| 1 | F | Cl | H | CH$_2$C(NOH)CH$_3$ | |
| 1 | F | Cl | H | CH$_2$CH(NOC$_2$H$_5$) | |
| 1 | F | Cl | H | CH(CH$_3$)C(O)CH$_3$ | |
| 1 | F | Cl | H | CH$_2$CN | |
| 1 | F | Cl | H | CH$_2$CO$_2$H | |
| 1 | F | Cl | H | CH$_2$CO$_2$CH$_3$ | |
| 1 | F | Cl | H | CH(CH$_3$)CO$_2$CH$_2$CH=CH$_2$ | |
| 1 | F | Cl | H | CH(CH$_3$)$_2$ | |
| 1 | F | Cl | H | CH$_2$CH$_2$)$_3$Br | |
| 1 | F | Cl | H | CH(CH$_3$)CH$_2$CH=CH$_2$ | |
| 1 | F | Cl | CH$_3$ | CH$_3$ | |
| 1 | F | Cl | CH$_3$ | CH$_2$OH | |
| 1 | F | Cl | CH$_3$ | CH$_2$OC(O)CH$_3$ | |
| 1 | F | Cl | CH$_3$ | CH$_2$CH$_3$ | |
| 1 | F | Cl | CH$_3$ | CO$_2$H | |
| 1 | F | Cl | CH$_3$ | CO$_2$CH$_3$ | |
| 1 | F | Cl | CH$_3$ | CN | |
| 1 | F | Cl | CH$_3$ | CH$_2$C(O)CH$_3$ | |
| 1 | F | Cl | CH$_3$ | CH$_2$CO$_2$H | |
| 1 | F | Cl | CH$_3$ | CH$_2$CO$_2$CH$_3$ | |
| 1 | F | Cl | H | H | |
| 1 | F | Cl | H | CH$_2$OH | 196-197.5 |
| 1 | F | Cl | H | CH$_2$OC(O)CH$_3$ | foam |
| 1 | F | Cl | H | CH$_2$Br | 134-136 |
| 1 | F | Cl | H | CH(NOCH$_2$CH=CH$_2$) | yellow oil |
| 1 | F | Cl | H | CO$_2$H | 220-221(dec) |
| 1 | F | Cl | H | CO$_2$CH$_3$ | 121-123 |
| 1 | F | Cl | H | CO$_2$CH$_2$CH$_3$ | 71-76 |
| 1 | F | Cl | H | CO$_2$C(CH$_3$)$_3$ | foam |
| 1 | F | Cl | H | CO$_2$CH(CH$_3$)CO$_2$C$_2$H$_5$ | foam |
| 1 | F | Cl | H | CO$_2$NH$_4$ | 197-198(dec) |
| 1 | F | Cl | H | CO$_2$NH$_3$CH(CH$_3$)$_2$ | 211-213(dec) |
| 1 | F | Cl | H | CO$_2$NA | 280-284(dec) |
| 1 | F | Br | H | H | |
| 1 | F | Br | H | CH$_2$OH | 195-196.5 |
| 1 | F | Br | H | CH$_2$OC(O)CH$_3$ | |
| 1 | F | Br | H | CH$_2$CH$_3$ | |
| 1 | F | Br | H | CH$_2$Br | |
| 1 | F | Br | H | C(O)CH$_3$ | |

TABLE 2-continued

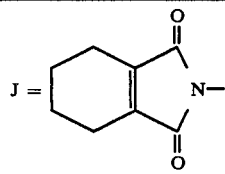

| m | R | $R_1$ | $R_2$ | $R_3$ | m.p. (°C.) |
|---|---|---|---|---|---|
| 1 | F | Br | H | CH(OH)CH$_3$ | |
| 1 | F | Br | H | CH(CH$_3$)OC(O)CH$_3$ | |
| 1 | F | Br | H | CO$_2$H | 200–205 |
| 1 | F | Br | H | CO$_2$CH$_3$ | foam |
| 1 | F | Br | H | COCl | oil |
| 1 | F | Br | H | CO$_2$C(CH$_3$)$_3$ | foam |
| 1 | F | Br | H | CO$_2$CH$_2$CH$_2$Cl | foam |
| 1 | F | Br | H | CN | |
| 1 | F | Br | H | CH(N—OC$_2$H$_5$) | |
| 1 | F | Br | H | C(O)N(CH$_3$)$_2$ | |
| 1 | F | Br | H | CH$_2$CO$_2$H | |
| 1 | F | Br | H | CH$_2$CO$_2$C$_2$H$_5$ | |
| 1 | F | Br | CH$_3$ | CH$_3$ | |
| 1 | F | Br | CH$_3$ | CH$_2$OH | |
| 1 | F | Br | CH$_3$ | CH$_2$OC(O)CH$_3$ | |
| 1 | F | Br | CH$_3$ | CH$_2$CH$_3$ | |
| 1 | F | Br | CH$_3$ | CO$_2$H | |
| 1 | F | Br | CH$_3$ | CO$_2$CH$_3$ | |
| 1 | F | Br | CH$_3$ | CH$_2$C(O)CH$_3$ | |
| 1 | F | Br | CH$_3$ | CH$_2$CO$_2$H | |
| 1 | F | Br | CH$_3$ | CH$_2$CO$_2$CH$_3$ | |
| 1 | Cl | Cl | H | CH$_2$OH | |
| 1 | Cl | Cl | H | CH$_2$OC(O)CH$_3$ | |
| 1 | Cl | Cl | H | CO$_2$H | |
| 1 | Cl | Cl | H | CO$_2$CH$_2$CH=CH$_2$ | |
| 1 | Cl | Cl | CH$_3$ | CH$_3$ | 160.5–162 |
| 1 | Cl | Cl | CH$_3$ | CH$_2$OH | |
| 1 | Cl | Cl | CH$_3$ | CO$_2$CH$_3$ | |
| 1 | Cl | Cl | CH$_3$ | CONHCH$_3$ | |
| 1 | H | CH$_3$ | H | CH$_2$OH | 177–179 |
| 1 | H | CH$_3$ | H | CH$_2$OC(O)CH$_3$ | 130–132 |
| 1 | H | CH$_3$ | H | CO$_2$H | 229–231(dec) |
| 1 | H | CH$_3$ | H | CO$_2$CH$_3$ | |
| 1 | H | CH$_3$ | H | CON(C$_2$H$_5$)$_2$ | |
| 1 | H | CH$_3$ | CH$_3$ | CH$_3$ | |
| 1 | H | CH$_3$ | CH$_3$ | CH$_2$OH | |
| 1 | H | CH$_3$ | CH$_3$ | CO$_2$H | |
| 1 | H | CH$_3$ | CH$_3$ | CO$_2$CH$_2$C≡CH | |
| 1 | F | CH$_3$ | H | CH$_2$OH | |
| 1 | F | CH$_3$ | H | CH$_2$OC(O)CH$_3$ | |
| 1 | F | CH$_3$ | H | CO$_2$H | |
| 1 | F | CH$_3$ | H | CO$_2$CH$_3$ | |
| 1 | F | CH$_3$ | H | C(O)CH$_3$ | |
| 1 | F | CH$_3$ | H | C(O)N(CH$_3$)$_2$ | |
| 1 | F | CH$_3$ | CH$_3$ | CH$_3$ | |
| 1 | F | CH$_3$ | CH$_3$ | CH$_2$OH | |
| 1 | F | CH$_3$ | CH$_3$ | CH$_2$OC(O)C$_2$H$_5$ | |
| 1 | F | CH$_3$ | CH$_3$ | CO$_2$H | |
| 1 | F | CH$_3$ | CH$_3$ | CO$_2$CH$_2$CH$_3$ | |
| 1 | F | CH$_3$ | CH$_3$ | CH$_2$CH$_3$ | |
| 1 | H | H | H | CH$_3$ | oil |
| 1 | F | H | H | CH$_3$ | |
| 1 | Cl | H | H | CH$_3$ | |
| 1 | CH$_3$ | H | H | CH$_3$ | |
| 1 | C$_2$H$_5$ | H | H | CH$_3$ | |
| 1 | CH$_3$O | H | H | CH$_3$ | |
| 1 | C$_2$H$_5$O | H | H | CH$_3$ | |
| 1 | C$_3$H$_7$O | H | H | CH$_3$ | |
| 1 | (CH$_3$)$_2$CHO | H | H | CH$_3$ | |
| 1 | H | Cl | H | CH$_3$ | 134–137 |
| 1 | F | Cl | H | CH$_3$ | 169–171 |
| 1 | Cl | Cl | H | CH$_3$ | 169.5–171 |
| 1 | CH$_3$ | Cl | H | CH$_3$ | |
| 1 | C$_2$H$_5$ | Cl | H | CH$_3$ | |
| 1 | CH$_3$O | Cl | H | CH$_3$ | |
| 1 | C$_2$H$_5$O | Cl | H | CH$_3$ | |
| 1 | C$_3$H$_7$O | Cl | H | CH$_3$ | |
| 1 | (CH$_3$)$_2$CHO | Cl | H | CH$_3$ | |
| 1 | H | Br | H | CH$_3$ | |
| 1 | F | Br | H | CH$_3$ | 147–151 |
| 1 | Cl | Br | H | CH$_3$ | |
| 1 | CH$_3$ | Br | H | CH$_3$ | |

TABLE 2-continued

J = 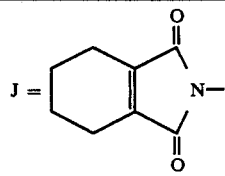

| m | R | $R_1$ | $R_2$ | $R_3$ | m.p. (°C.) |
|---|---|---|---|---|---|
| 1 | $C_2H_5$ | Br | H | $CH_3$ | |
| 1 | $CH_3O$ | Br | H | $CH_3$ | |
| 1 | $C_2H_5O$ | Br | H | $CH_3$ | |
| 1 | $C_3H_7O$ | Br | H | $CH_3$ | |
| 1 | $(CH_3)_2CHO$ | Br | H | $CH_3$ | |
| 1 | H | $CH_3$ | H | $CH_3$ | 158–160 |
| 1 | F | $CH_3$ | H | $CH_3$ | |
| 1 | Cl | $CH_3$ | H | $CH_3$ | |
| 1 | $CH_3$ | $CH_3$ | H | $CH_3$ | |
| 1 | $C_2H_5$ | $CH_3$ | H | $CH_3$ | |
| 1 | $CH_3O$ | $CH_3$ | H | $CH_3$ | |
| 1 | $C_2H_5O$ | $CH_3$ | H | $CH_3$ | |
| 1 | $C_3H_7O$ | $CH_3$ | H | $CH_3$ | |
| 1 | $(CH_3)_2CHO$ | $CH_3$ | H | $CH_3$ | |
| 1 | H | $OCH_3$ | H | $CH_3$ | |
| 1 | F | $OCH_3$ | H | $CH_3$ | |
| 1 | Cl | $OCH_3$ | H | $CH_3$ | |
| 1 | $CH_3$ | $OCH_3$ | H | $CH_3$ | |
| 1 | $C_2H_5$ | $OCH_3$ | H | $CH_3$ | |
| 1 | $CH_3O$ | $OCH_3$ | H | $CH_3$ | |
| 1 | $C_2H_5O$ | $OCH_3$ | H | $CH_3$ | |
| 1 | $C_3H_7O$ | $OCH_3$ | H | $CH_3$ | |
| 1 | $(CH_3)_2CHO$ | $OCH_3$ | H | $CH_3$ | |
| 1 | H | CN | H | $CH_3$ | |
| 1 | F | CN | H | $CH_3$ | |
| 1 | Cl | CN | H | $CH_3$ | |
| 1 | $CH_3$ | CN | H | $CH_3$ | |
| 1 | $C_2H_5$ | CN | H | $CH_3$ | |
| 1 | $CH_3O$ | CN | H | $CH_3$ | |
| 1 | $C_2H_5O$ | CN | H | $CH_3$ | |
| 1 | $C_3H_7O$ | CN | H | $CH_3$ | |
| 1 | $(CH_3)_2CHO$ | CN | H | $CH_3$ | |
| 1 | H | $CF_3$ | H | $CH_3$ | |
| 1 | F | $CF_3$ | H | $CH_3$ | |
| 1 | Cl | $CF_3$ | H | $CH_3$ | |
| 1 | $CH_3$ | $CF_3$ | H | $CH_3$ | |
| 1 | $C_2H_5$ | $CF_3$ | H | $CH_3$ | |
| 1 | $CH_3O$ | $CF_3$ | H | $CH_3$ | |
| 1 | $C_2H_5O$ | $CF_3$ | H | $CH_3$ | |
| 1 | $C_3H_7O$ | $CF_3$ | H | $CH_3$ | |
| 1 | $(CH_3)_2CHO$ | $CF_3$ | H | $CH_3$ | |
| 1 | H | $OCF_3$ | H | $CH_3$ | |
| 1 | F | $OCF_3$ | H | $CH_3$ | |
| 1 | Cl | $OCF_3$ | H | $CH_3$ | |
| 1 | $CH_3$ | $OCF_3$ | H | $CH_3$ | |
| 1 | $C_2H_5$ | $OCF_3$ | H | $CH_3$ | |
| 1 | $CH_3O$ | $OCF_3$ | H | $CH_3$ | |
| 1 | $C_2H_5O$ | $OCF_3$ | H | $CH_3$ | |
| 1 | $C_3H_7O$ | $OCF_3$ | H | $CH_3$ | |
| 1 | $(CH_3)_2CHO$ | $OCF_3$ | H | $CH_3$ | |
| 1 | H | $OCF_2H$ | H | $CH_3$ | |
| 1 | F | $OCF_2H$ | H | $CH_3$ | |
| 1 | Cl | $OCF_2H$ | H | $CH_3$ | |
| 1 | $CH_3$ | $OCF_2H$ | H | $CH_3$ | |
| 1 | $C_2H_5$ | $OCF_2H$ | H | $CH_3$ | |
| 1 | $CH_3O$ | $OCF_2H$ | H | $CH_3$ | |
| 1 | $C_2H_5O$ | $OCF_2H$ | H | $CH_3$ | |
| 1 | $C_3H_7O$ | $OCF_2H$ | H | $CH_3$ | |
| 1 | $(CH_3)_2CHO$ | $OCF_2H$ | H | $CH_3$ | |
| 2 | F | Cl | H | $CH_2OH$ | |
| 2 | F | Cl | H | $CH_2OC(O)CH_3$ | |
| 2 | F | Cl | H | $CH_2CH_3$ | |
| 2 | F | Cl | H | $CH(CH_3)OH$ | |
| 2 | F | Cl | H | $CH(CH_3)OC(O)CH_3$ | |
| 2 | F | Cl | H | $CH_2Br$ | |
| 2 | F | Cl | H | $C(O)CH_3$ | |
| 2 | F | Cl | H | $C(NOCH_2CH=CH_2)CH_3$ | |
| 2 | F | Cl | H | $CO_2H$ | |
| 2 | F | Cl | H | $CO_2CH_3$ | |
| 2 | F | Cl | H | CN | |
| 2 | F | Cl | H | $C(O)N(CH_3)_2$ | |
| 2 | F | Cl | H | $C(O)NHSO_2CH_3$ | |

TABLE 2-continued

J = 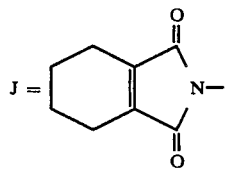

| m | R | $R_1$ | $R_2$ | $R_3$ | m.p. (°C.) |
|---|---|---|---|---|---|
| 2 | F | Cl | $CH_3$ | $CH_3$ | |
| 2 | F | Cl | $CH_3$ | $CH_2OC(O)CH_3$ | |
| 2 | F | Cl | $CH_3$ | $CO_2H$ | |
| 2 | F | Cl | $CH_3$ | $CO_2CH_3$ | |
| 2 | F | Cl | $CH_3$ | CN | |
| 2 | F | Cl | $CH_3$ | $C_2H_5$ | |
| 2 | F | Br | H | H | |
| 2 | F | Br | H | $CH_3$ | |
| 2 | F | Br | H | $CH_2OH$ | |
| 2 | F | Br | H | $CH_2OC(O)CH_3$ | |
| 2 | F | Br | H | $CH_2CH_3$ | |
| 2 | F | Br | H | $CH(CH_3)OH$ | |
| 2 | F | Br | H | $CH(CH_3)OC(O)CH_3$ | |
| 2 | F | Br | H | $CH_2Br$ | |
| 2 | F | Br | H | $C(O)CH_3$ | |
| 2 | F | Br | H | $C(NOCH_2CH=CH_2)CH_3$ | |
| 2 | F | Br | H | $CO_2H$ | |
| 2 | F | Br | H | $CO_2CH_3$ | |
| 2 | F | Br | H | CN | |
| 2 | F | Br | H | $C(O)N(CH_3)_2$ | |
| 2 | F | Br | H | $C(O)NHSO_2CH_3$ | |
| 2 | F | Br | $CH_3$ | $CH_3$ | |
| 2 | F | Br | $CH_3$ | $CH_2OC(O)CH_3$ | |
| 2 | F | Br | $CH_3$ | $CO_2H$ | |
| 2 | F | Br | $CH_3$ | $CO_2CH_3$ | |
| 2 | F | Br | $CH_3$ | CN | |
| 2 | F | Br | $CH_3$ | $C_2H_5$ | |
| 2 | Cl | Cl | H | H | 191-193 |
| 2 | Cl | Cl | H | $CH_3$ | |
| 2 | Cl | Cl | H | $CH_2OH$ | |
| 2 | Cl | Cl | H | $CH_2OC(O)CH_3$ | |
| 2 | Cl | Cl | H | $CH_2CH_3$ | |
| 2 | Cl | Cl | H | $CH(CH_3)OH$ | |
| 2 | Cl | Cl | H | $CH(CH_3)OC(O)CH_3$ | |
| 2 | Cl | Cl | H | $CH_2Br$ | |
| 2 | Cl | Cl | H | $C(O)CH_3$ | |
| 2 | Cl | Cl | H | $C(NOCH_2CH=CH_2)CH_3$ | |
| 2 | Cl | Cl | H | $CO_2H$ | |
| 2 | Cl | Cl | H | $CO_2CH_3$ | |
| 2 | Cl | Cl | H | CN | |
| 2 | Cl | Cl | H | $C(O)N(CH_3)_2$ | |
| 2 | Cl | Cl | H | $C(O)NHSO_2CH_3$ | |
| 2 | Cl | Cl | $CH_3$ | $CH_3$ | |
| 2 | Cl | Cl | $CH_3$ | $CH_2OC(O)CH_3$ | |
| 2 | Cl | Cl | $CH_3$ | $CO_2H$ | |
| 2 | Cl | Cl | $CH_3$ | $CO_2CH_3$ | |
| 2 | Cl | Cl | $CH_3$ | CN | |
| 2 | Cl | Cl | $CH_3$ | $C_2H_5$ | |

TABLE 3

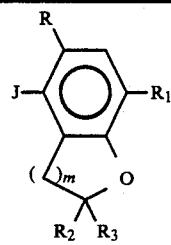

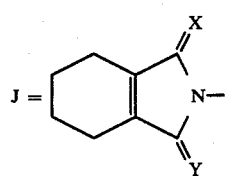

| m | X | Y | R | R₁ | R₂ | R₃ | m.p. (°C.) |
|---|---|---|---|----|----|----|-----------|
| 1 | S | S | H  | Cl | H   | CH₃       | glass |
| 1 | S | S | F  | Cl | CH₃ | CH₃       |       |
| 1 | S | S | Cl | Cl | H   | CO₂CH₃    |       |
| 1 | S | S | F  | Br | H   | CH₃       |       |
| 1 | S | O | H  | Cl | H   | CH₃       | foam |
| 1 | S | O | F  | Cl | CH₃ | CH₃       |       |
| 1 | S | O | Cl | Cl | H   | CO₂CH₃    |       |
| 1 | S | O | F  | Br | H   | CH₃       |       |
| 2 | S | S | F  | Cl | H   | H         |       |
| 2 | S | O | F  | Br | H   | CH₃       |       |

TABLE 4

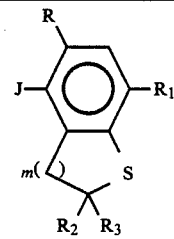

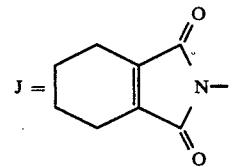

| m | R | R₁ | R₂ | R₃ | m.p. (°C.) |
|---|---|----|----|----|-----------|
|   | F | Cl | H  | H         |        |
| 1 | F | Cl | H  | CH₃       | glass  |
| 1 | F | Cl | H  | CH₂OH     | 75–77  |
| 1 | F | Cl | H  | CH₂OC(O)CH₃ | oil  |
| 1 | F | Cl | H  | CH₂CH₃    |        |
| 1 | F | Cl | H  | CH(CH₃)OH |        |
| 1 | F | Cl | H  | CH(CH₃)OC(O)CH₃ |  |
| 1 | F | Cl | H  | CH₂Br     | 144–146 |
| 1 | F | Cl | H  | C(O)CH₃   |        |
| 1 | F | Cl | H  | C(NOCH₂CH=CH₂)CH₃ | |
| 1 | F | Cl | H  | CO₂H      | oil    |
| 1 | F | Cl | H  | CO₂CH₃    | oil    |
| 1 | F | Cl | H  | CN        |        |
| 1 | F | Cl | H  | C(O)N(CH₃)₂ |      |
| 1 | F | Cl | H  | C(O)NHSO₂CH₃ |    |
| 1 | F | Cl | CH₃ | CH₃      |        |
| 1 | F | Cl | CH₃ | CH₂OC(O)CH₃ |    |
| 1 | F | Cl | CH₃ | CO₂H     |        |
| 1 | F | Cl | CH₃ | CO₂CH₃   |        |
| 1 | F | Cl | CH₃ | CN       |        |
| 1 | F | Cl | CH₃ | C₂H₅     |        |
| 2 | F | Cl | H  | H         |        |
| 2 | F | Cl | H  | CH₃       |        |

TABLE 4-continued

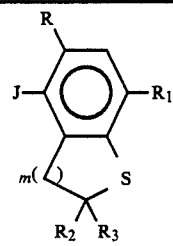

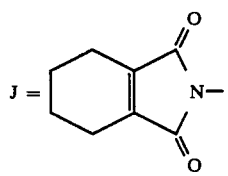

| m | R | R₁ | R₂ | R₃ | m.p. (°C.) |
|---|---|----|----|----|-----------|
| 2 | F | Cl | H  | CH₂OH     |  |
| 2 | F | Cl | H  | CH₂OC(O)CH₃ |  |
| 2 | F | Cl | H  | CH₂CH₃    |  |
| 2 | F | Cl | H  | CH(CH₃)OH |  |
| 2 | F | Cl | H  | CH(CH₃)OC(O)CH₃ |  |
| 2 | F | Cl | H  | CH₂Br     |  |
| 2 | F | Cl | H  | C(O)CH₃   |  |
| 2 | F | Cl | H  | C(NOCH₂CH=CH₂)CH₃ |  |
| 2 | F | Cl | H  | CO₂H      |  |
| 2 | F | Cl | H  | CO₂CH₃    |  |
| 2 | F | Cl | H  | CN        |  |
| 2 | F | Cl | H  | C(O)N(CH₃)₂ |  |
| 2 | F | Cl | H  | C(O)NHSO₂CH₃ |  |
| 2 | F | Cl | CH₃ | CH₃      |  |
| 2 | F | Cl | CH₃ | CH₂OC(O)CH₃ |  |
| 2 | F | Cl | CH₃ | CO₂H     |  |
| 2 | F | Cl | CH₃ | CO₂CH₃   |  |
| 2 | F | Cl | CH₃ | CN       |  |
| 2 | F | Cl | CH₃ | C₂H₅     |  |

TABLE 5

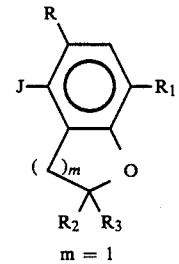

m = 1

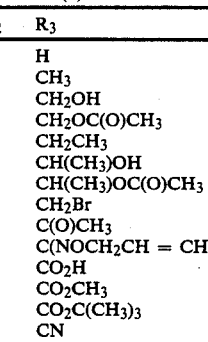

| n | R | R₁ | R₂ | R₃ | m.p. (°C.) |
|---|---|----|----|----|-----------|
| 1 | F | Cl | H  | H         |        |
| 1 | F | Cl | H  | CH₃       | 158–159 |
| 1 | F | Cl | H  | CH₂OH     | 236–238 |
| 1 | F | Cl | H  | CH₂OC(O)CH₃ | stiff oil |
| 1 | F | Cl | H  | CH₂CH₃    |        |
| 1 | F | Cl | H  | CH(CH₃)OH |        |
| 1 | F | Cl | H  | CH(CH₃)OC(O)CH₃ |  |
| 1 | F | Cl | H  | CH₂Br     |        |
| 1 | F | Cl | H  | C(O)CH₃   |        |
| 1 | F | Cl | H  | C(NOCH₂CH=CH₂)CH₃ |  |
| 1 | F | Cl | H  | CO₂H      | 239–241 |
| 1 | F | Cl | H  | CO₂CH₃    | foam   |
| 1 | F | Cl | H  | CO₂C(CH₃)₃ | foam  |
| 1 | F | Cl | H  | CN        |        |

TABLE 5-continued

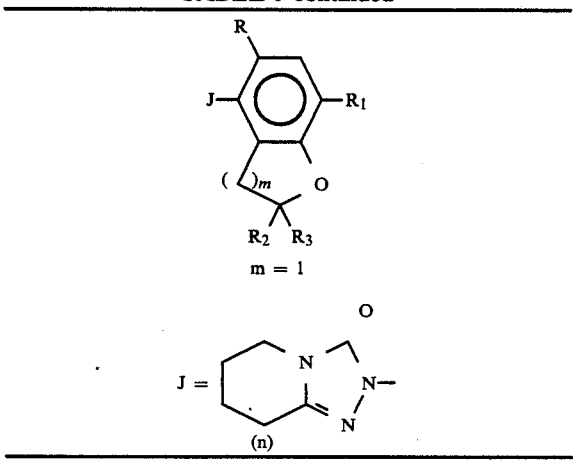

m = 1

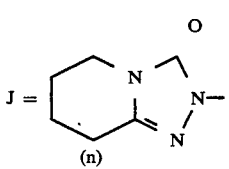

| n | R | R₁ | R₂ | R₃ | m.p.(°C.) |
|---|---|---|---|---|---|
| 1 | F | Cl | H | C(O)N(CH₃)₂ | foam |
| 1 | F | Cl | H | C(O)NHSO₂CH₃ | |
| 1 | F | Cl | H | C(O)Cl | foam |
| 1 | F | Cl | CH₃ | CH₃ | |
| 1 | F | Cl | CH₃ | CH₂OH | |
| 1 | F | Cl | CH₃ | CH₂OC(O)CH(CH₃)₂ | |
| 1 | F | Cl | CH₃ | CO₂H | |
| 1 | F | Cl | CH₃ | CO₂CH₃ | |
| 1 | F | Cl | CH₃ | CN | |
| 1 | F | Cl | CH₃ | C(O)NH(CH₃) | |
| 1 | F | Cl | CH₃ | C₂H₅ | |
| 1 | Cl | Cl | H | H | |
| 1 | Cl | Cl | H | CH₃ | 198–202 |
| 1 | Cl | Cl | H | CH₂OH | |
| 1 | Cl | Cl | H | CH₂OC(O)CH3 | |
| 1 | Cl | Cl | H | CH₂CH₃ | |
| 1 | Cl | Cl | H | CH(CH₃)OH | |
| 1 | Cl | Cl | H | CH(CH₃)OC(O)CH₃ | |
| 1 | Cl | Cl | H | CH₂Br | |
| 1 | Cl | Cl | H | C(O)CH₃ | |
| 1 | Cl | Cl | H | C(NOCH₂CH=CH₂)CH₃ | |
| 1 | Cl | Cl | H | CO₂H | |
| 1 | Cl | Cl | H | CO₂CH₃ | |
| 1 | Cl | Cl | H | CO₂C(CH₃)₃ | |
| 1 | Cl | Cl | H | CN | |
| 1 | Cl | Cl | H | C(O)N(CH₃)₂ | |
| 1 | Cl | Cl | H | C(O)NHSO₂CH₃ | |
| 1 | Cl | Cl | CH₃ | CH₃ | |
| 1 | Cl | Cl | CH₃ | CH₂OH | |
| 1 | Cl | Cl | CH₃ | CH₂OC(O)CH₃ | |
| 1 | Cl | CL | CH₃ | CO₂H | |
| 1 | Cl | Cl | CH₃ | CO₂CH₃ | |
| 1 | Cl | Cl | CH₃ | CN | |

| n | m | R | R₁ | R₂ | R₃ | m.p.(°C.) |
|---|---|---|---|---|---|---|
| 1 | 1 | Cl | Cl | CH₃ | C(O)NH(CH₃) | |
| 1 | 1 | Cl | Cl | CH₃ | C₂H₅ | |
| 1 | 1 | F | Br | H | H | |
| 1 | 1 | F | Br | H | CH₃ | |
| 1 | 1 | F | Br | H | CH₂OH | |
| 1 | 1 | F | Br | H | CH₂OC(O)CH₃ | |
| 1 | 1 | F | Br | H | CH₂CH₃ | |
| 1 | 1 | F | Br | H | CO₂H | |
| 1 | 1 | F | Br | H | CO₂CH₃ | |
| 1 | 1 | F | Br | H | C(O)N(CH₃)₂ | |
| 1 | 1 | F | Br | CH₃ | CH₃ | |
| 1 | 1 | F | Br | CH₃ | CH₂OC(O)CH₃ | |
| 1 | 1 | F | Br | CH₃ | CO₂CH₃ | |
| 1 | 1 | F | Br | CH₃ | CONH(CH₃) | |
| 1 | 1 | H | Cl | H | CH₃ | 170.5–172 |
| 2 | 1 | F | Cl | H | CH₃ | |
| 2 | 1 | Cl | Cl | H | CH₃ | |
| 2 | 1 | H | Cl | H | CH₃ | 148–150 |
| 2 | 1 | F | Br | H | CH₃ | |
| 2 | 1 | F | Cl | CH₃ | CH₃ | |
| 2 | 1 | Cl | CL | CH₃ | CH₃ | |
| 2 | 1 | H | Cl | CH₃ | CH₃ | |
| 2 | 1 | F | Br | CH₃ | CH₃ | |
| 1 | 2 | Cl | Cl | H | H | 221–224 |
| 1 | 2 | Cl | Cl | H | CH₃ | |
| 1 | 2 | Cl | Cl | H | CH₂OH | |
| 1 | 2 | Cl | Cl | H | CH₂OC(O)CH₃ | |
| 1 | 2 | Cl | Cl | H | CH₂CH₃ | |
| 1 | 2 | Cl | Cl | H | CH₂Br | |
| 1 | 2 | Cl | Cl | H | C(O)CH₃ | |
| 1 | 2 | Cl | Cl | H | CO₂H | |
| 1 | 2 | Cl | Cl | H | CO₂CH₃ | |
| 1 | 2 | Cl | Cl | H | CO₂C(CH₃)₃ | |
| 1 | 2 | Cl | Cl | H | CN | |
| 1 | 2 | Cl | Cl | H | C(O)N(CH₃)₂ | |
| 1 | 2 | Cl | Cl | H | C(O)NHSO₂CH₃ | |
| 1 | 2 | Cl | Cl | CH₃ | CH₃ | |
| 1 | 2 | Cl | Cl | CH₃ | CH₂OH | |
| 1 | 2 | Cl | Cl | CH₃ | CO₂H | |
| 1 | 2 | Cl | Cl | CH₃ | CO₂CH₃ | |
| 1 | 2 | Cl | Cl | CH₃ | CN | |
| 1 | 2 | Cl | Cl | CH₃ | C(O)NH(CH₃) | |
| 1 | 2 | Cl | Cl | CH₃ | C₂H₅ | |
| 1 | 2 | F | Br | H | H | |
| 1 | 2 | F | Br | H | CH₃ | |
| 1 | 2 | F | Br | H | CH₂OH | |
| 1 | 2 | F | Br | H | CH₂OC(O)CH₃ | |
| 1 | 2 | F | Br | H | CH₂CH₃ | |
| 1 | 2 | F | Br | H | CO₂H | |
| 1 | 2 | F | Br | H | CO₂CH₃ | |
| 1 | 2 | F | Br | H | C(O)N(CH₃)₂ | |
| 1 | 2 | F | Br | CH₃ | CH₃ | |
| 1 | 2 | F | Br | CH₃ | CH₂OC(O)CH₃ | |
| 1 | 2 | F | Br | CH₃ | CO₂CH₃ | |
| 1 | 2 | F | Br | CH₃ | CONH(CH₃) | |
| 2 | 2 | H | Cl | H | CH₃ | |
| 2 | 2 | F | Cl | H | CH₃ | |
| 2 | 2 | H | Cl | H | CH₃ | |
| 2 | 2 | F | Br | H | CH₃ | |
| 2 | 2 | F | Cl | CH₃ | CH₃ | |
| 2 | 2 | Cl | Cl | CH₃ | CH₃ | |
| 2 | 2 | H | Cl | CH₃ | CH₃ | |
| 2 | 2 | F | Br | CH₃ | CH₃ | |
| 1 | 2 | F | Cl | H | H | 178–180 |
| 1 | 2 | F | Cl | H | CH₃ | |
| 1 | 2 | F | Cl | H | CH₂OH | |
| 1 | 2 | F | Cl | H | CH₂OC(O)CH₃ | |
| 1 | 2 | F | Cl | H | CH₂CH₃ | |
| 1 | 2 | F | Cl | H | CH₂Br | |
| 1 | 2 | F | Cl | H | C(O)CH₃ | |
| 1 | 2 | F | Cl | H | CO₂H | |
| 1 | 2 | F | Cl | H | CO₂CH₃ | |
| 1 | 2 | F | Cl | H | CO₂C(CH₃)₃ | |
| 1 | 2 | F | Cl | H | CN | |
| 1 | 2 | F | Cl | H | C(O)N(CH₃)₂ | |
| 1 | 2 | F | Cl | H | C(O)NHSO₂CH₃ | |
| 1 | 2 | F | Cl | CH₃ | CH₃ | |
| 1 | 2 | F | Cl | CH₃ | CH₂OH | |
| 1 | 2 | F | Cl | CH₃ | CO₂H | |
| 1 | 2 | F | Cl | CH₃ | CO₂CH₃ | |
| 1 | 2 | F | Cl | CH₃ | CN | |
| 1 | 2 | F | Cl | CH₃ | C(O)NH(CH₃) | |
| 1 | 2 | F | Cl | CH₃ | C₂H₅ | |

TABLE 5a

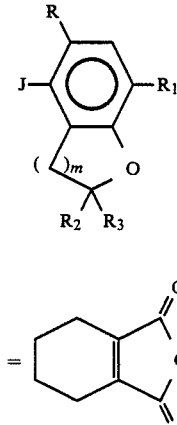

$$J = \text{(piperidine fused triazolone ring system with n)}$$

| m | n | R | R₁ | R₂ | R₃ | m.p. (°C.) |
|---|---|---|----|----|----|-----------|
| 1 | 1 | F | Cl | H | H | |
| 1 | 1 | F | Cl | H | CH₃ | |
| 1 | 1 | F | Cl | H | CH₂OH | |
| 1 | 1 | F | Cl | H | CO₂CH₃ | |
| 1 | 1 | F | Cl | CH₃ | CH₃ | |
| 2 | 1 | F | Cl | H | H | |
| 2 | 1 | F | Cl | H | CH₃ | |
| 2 | 1 | F | Cl | H | CH₂OH | |
| 2 | 1 | F | Cl | H | CO₂CH₃ | |
| 2 | 1 | F | Cl | CH₃ | CH₃ | |
| 1 | 2 | F | Cl | H | H | |
| 1 | 2 | F | Cl | H | CH₃ | |
| 1 | 2 | F | Cl | H | CH₂OH | |
| 1 | 2 | F | Cl | H | CO₂CH₃ | |
| 1 | 2 | F | Cl | CH₃ | CH₃ | |
| 2 | 2 | F | Cl | H | H | |
| 2 | 2 | F | Cl | H | CH₃ | |
| 2 | 2 | F | Cl | H | CH₂OH | |
| 2 | 2 | F | Cl | H | CO₂CH₃ | |
| 2 | 2 | F | Cl | CH₃ | CH₃ | |
| 1 | 1 | Cl | Cl | H | H | |
| 1 | 1 | Cl | Cl | H | CH₃ | |
| 1 | 1 | Cl | Cl | H | CH₂OH | |
| 1 | 1 | Cl | Cl | H | CO₂CH₃ | |
| 1 | 1 | Cl | Cl | CH₃ | CH₃ | |
| 2 | 1 | Cl | Cl | H | H | |
| 2 | 1 | Cl | Cl | H | CH₃ | |
| 2 | 1 | Cl | Cl | H | CH₂OH | |
| 2 | 1 | Cl | Cl | H | CO₂CH₃ | |
| 2 | 1 | Cl | Cl | CH₃ | CH₃ | |
| 1 | 2 | Cl | Cl | H | H | |
| 1 | 2 | Cl | Cl | H | CH₃ | |
| 1 | 2 | Cl | Cl | H | CH₂OH | |
| 1 | 2 | Cl | Cl | H | CO₂CH₃ | |
| 1 | 2 | Cl | Cl | CH₃ | CH₃ | |
| 2 | 2 | Cl | Cl | H | H | |
| 2 | 2 | Cl | Cl | H | CH₃ | |
| 2 | 2 | Cl | Cl | H | CH₂OH | |
| 2 | 2 | Cl | Cl | H | CO₂CH₃ | |
| 2 | 2 | Cl | Cl | CH₃ | CH₃ | |
| 1 | 1 | F | Br | H | H | |
| 1 | 1 | F | Br | H | CH₃ | |
| 1 | 1 | F | Br | H | CH₂OH | |
| 1 | 1 | F | Br | H | CO₂CH₃ | |
| 1 | 1 | F | Br | CH₃ | CH₃ | |
| 2 | 1 | F | Br | H | H | |
| 2 | 1 | F | Br | H | CH₃ | |
| 2 | 1 | F | Br | H | CH₂OH | |
| 2 | 1 | F | Br | H | CO₂CH₃ | |
| 2 | 1 | F | Br | CH₃ | CH₃ | |
| 1 | 2 | F | Br | H | H | |
| 1 | 2 | F | Br | H | CH₃ | |
| 1 | 2 | F | Br | H | CH₂OH | |
| 1 | 2 | F | Br | H | CO₂CH₃ | |
| 1 | 2 | F | Br | CH₃ | CH₃ | |
| 2 | 2 | F | Br | H | H | |
| 2 | 2 | F | Br | H | CH₃ | |
| 2 | 2 | F | Br | H | CH₂OH | |
| 2 | 2 | F | Br | H | CO₂CH₃ | |

TABLE 5a-continued

| m | n | R | R₁ | R₂ | R₃ | m.p. (°C.) |
|---|---|---|----|----|----|-----------|
| 2 | 2 | F | Br | CH₃ | CH₃ | |

TABLE 6

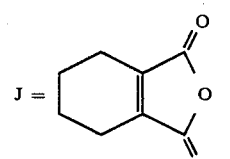

| m | R | R₁ | R₂ | R₃ | m.p.(°C.) |
|---|---|----|----|----|-----------|
| 1 | H | Cl | H | CH₃ | 125–127 |
| 1 | F | Cl | H | H | |
| 1 | F | Cl | H | CH₃ | glass |
| 1 | F | Cl | H | CH₂OC(O)CH₃ | |
| 1 | F | Cl | H | CO₂CH₃ | |
| 1 | F | Cl | CH₃ | CH₃ | |
| 2 | F | Cl | H | H | 131–133 |
| 2 | F | Cl | H | CH₃ | |
| 2 | F | Cl | H | CH₂OC(O)CH₃ | |
| 2 | F | Cl | H | CO₂CH₃ | |
| 2 | F | Cl | CH₃ | CH₃ | |
| 1 | F | Br | H | H | |
| 1 | F | Br | H | CH₃ | |
| 1 | F | Br | CH₃ | CH₃ | |
| 2 | F | Br | H | H | |
| 2 | F | Br | H | CH₃ | |
| 2 | F | Br | CH₃ | CH₃ | |

TABLE 7

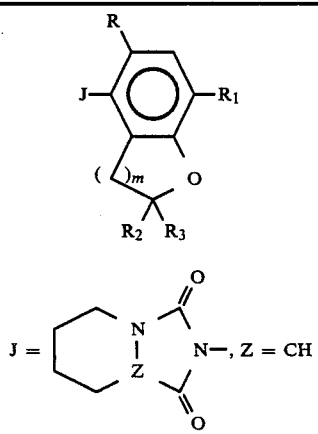

| m | R  | R₁ | R₂  | R₃           | m.p.(°C.)        |
|---|----|----|-----|--------------|------------------|
| 1 | H  | Cl | H   | CH₃          | 145–148          |
| 1 | Cl | Cl | H   | CH₃          | 182–185(Isomer 1)|
| 1 | Cl | Cl | H   | CH₃          | 206–108(Isomer 2)|
| 1 | Cl | Cl | CH₃ | CH₃          |                  |
| 1 | F  | Cl | H   | CH₃          | 150–152          |
| 1 | F  | Cl | H   | CH₂OC(O)CH₃  |                  |
| 1 | F  | Cl | H   | CO₂CH₃       | foam             |
| 1 | F  | Cl | CH₃ | CH₃          |                  |
| 1 | F  | Br | H   | CH₃          |                  |
| 1 | F  | Br | CH₃ | CH₃          |                  |
| 2 | F  | Cl | H   | H            | 169–172(Isomer 1)|
| 2 | F  | Cl | H   | CH₃          | 161–163(Isomer 2)|
| 2 | F  | Cl | CH₃ | CH₃          |                  |
| 2 | Cl | Cl | H   | H            | 204–208(Isomer 1)|
| 2 | Cl | Cl | H   | CH₃          | 209–211(Isomer 2)|
| 2 | Cl | Cl | CH₃ | CH₃          |                  |
| 2 | F  | Br | H   | H            |                  |
| 2 | F  | Br | H   | CH₃          |                  |
| 2 | F  | Br | CH₃ | CH₃          |                  |

TABLE 8

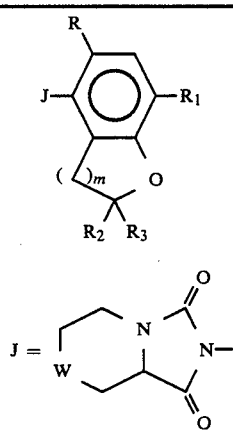

| m | W   | R  | R₁ | R₂  | R₃  | m.p.(°C.) |
|---|-----|----|----|-----|-----|-----------|
| 1 | S   | F  | Cl | H   | H   |           |
| 1 | S   | F  | Cl | CH₃ | CH₃ |           |
| 1 | S   | Cl | Cl | H   | H   |           |
| 1 | S   | Cl | Cl | CH₃ | CH₃ |           |
| 1 | S   | Cl | Cl | CH₃ | CH₃ |           |
| 1 | S   | F  | Br | H   | H   |           |
| 1 | S   | F  | Br | H   | CH₃ |           |
| 1 | S   | F  | Br | CH₃ | CH₃ |           |
| 1 | SO₂ | F  | Cl | H   | CH₃ |           |
| 1 | SO₂ | Cl | Cl | H   | H   |           |
| 1 | SO₂ | F  | Br | CH₃ | CH₃ |           |

TABLE 8-continued

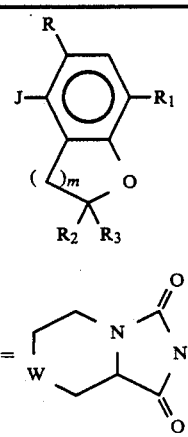

| m | W   | R  | R₁ | R₂  | R₃  | m.p.(°C.) |
|---|-----|----|----|-----|-----|-----------|
| 2 | S   | F  | Cl | H   | H   |           |
| 2 | S   | Cl | Cl | H   | CH₃ |           |
| 2 | S   | F  | Br | CH₃ | CH₃ |           |
| 2 | SO₂ | F  | Cl | H   | CH₃ |           |
| 2 | SO₂ | Cl | Cl | H   | H   |           |
| 2 | SO₂ | F  | Br | CH₃ | CH₃ |           |

TABLE 9

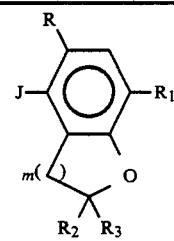

| m | n | R  | R₁ | R₂  | R₃             | m.p. (°C.)   |
|---|---|----|----|-----|----------------|--------------|
| 1 | 1 | H  | Cl | H   | CH₃            | 175–177      |
| 1 | 1 | Cl | Cl | H   | CH₃            | 201.5–203.5  |
| 1 | 1 | Cl | Cl | CH₃ | CH₃            |              |
| 1 | 1 | F  | Cl | H   | CH₃            | 192–194.5    |
| 1 | 1 | F  | Cl | CH₃ | CH₃            |              |
| 1 | 1 | F  | Cl | H   | CO₂(CH₂)₄Br    | oil          |
| 1 | 1 | F  | Cl | H   | CO₂CH₃         | glass        |
| 1 | 1 | F  | Br | H   | CH₃            |              |
| 1 | 1 | F  | Br | CH₃ | CH₃            |              |
| 2 | 1 | F  | Cl | H   | H              | 185–188      |
| 2 | 1 | F  | Cl | H   | CH₃            |              |
| 2 | 1 | F  | Cl | CH₃ | CH₃            |              |
| 2 | 1 | Cl | Cl | H   | H              | 210–214      |
| 2 | 1 | Cl | Cl | H   | CH₃            |              |
| 2 | 1 | Cl | Cl | CH₃ | CH₃            |              |
| 2 | 1 | F  | Br | H   | H              |              |
| 2 | 1 | F  | Br | H   | CH₃            |              |
| 2 | 1 | F  | Br | CH₃ | CH₃            |              |
| 1 | 2 | F  | Cl | H   | CH₃            |              |
| 1 | 2 | F  | Cl | CH₃ | CH₃            |              |
| 1 | 2 | Cl | Cl | H   | CH₃            |              |
| 1 | 2 | Cl | Cl | CH₃ | CH₃            |              |
| 1 | 2 | F  | Br | H   | CH₃            |              |
| 1 | 2 | F  | Br | CH₃ | CH₃            |              |
| 2 | 2 | F  | Cl | H   | H              | 174–178      |
| 2 | 2 | F  | Cl | H   | CH₃            |              |
| 2 | 2 | F  | Cl | CH₃ | CH₃            |              |

TABLE 9-continued

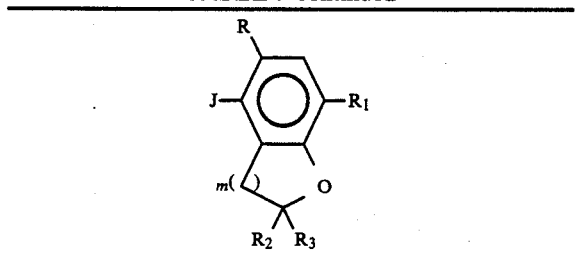

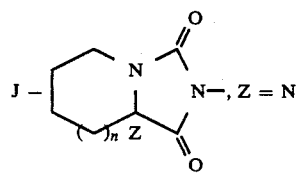

| m | n | R | R₁ | R₂ | R₃ | m.p. (°C.) |
|---|---|---|---|----|----|------------|
| 2 | 2 | Cl | Cl | H | H | 149–153 |
| 2 | 2 | Cl | Cl | H | CH₃ | |
| 2 | 2 | Cl | Cl | CH₃ | CH₃ | |
| 2 | 2 | F | Br | H | H | |
| 2 | 2 | F | Br | H | CH₃ | |
| 2 | 2 | F | Br | CH₃ | CH₃ | |

TABLE 10

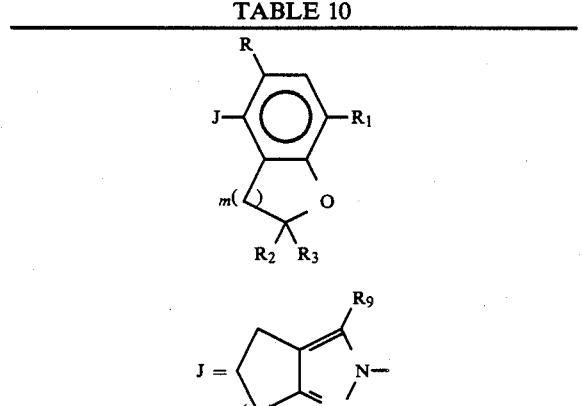

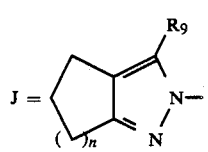

| m | n | R | R₁ | R₂ | R₃ | R₉ | m.p. (°C.) |
|---|---|---|----|----|----|----|-----------|
| 1 | 2 | F | Cl | H | CH₃ | F | |
| 1 | 2 | F | Cl | H | CH₃ | Cl | |
| 1 | 2 | F | Cl | H | CH₃ | Br | |
| 1 | 2 | F | Cl | H | CH₃ | CH₃ | |
| 1 | 2 | F | Cl | H | CH₃ | CN | |
| 1 | 2 | F | Cl | H | CH₃ | OCH₃ | |
| 1 | 2 | F | Cl | H | CH₃ | SCH₃ | |
| 1 | 2 | F | Cl | H | CH₃ | SO₂CH₃ | |
| 1 | 1 | F | Cl | H | CH₃ | Cl | |
| 1 | 1 | F | Cl | H | CH₃ | Br | |
| 1 | 1 | F | Cl | H | CH₃ | CN | |
| 1 | 2 | H | Cl | H | CH₃ | Cl | oil |
| 1 | 2 | F | Cl | H | CH₃ | Cl | glass |
| 1 | 2 | F | Cl | H | CH₂OC(O)CH₃ | Cl | |
| 1 | 2 | F | Cl | H | CO₂CH₃ | Cl | |
| 1 | 2 | F | Cl | H | C(O)N(CH₃)₂ | Cl | |
| 1 | 2 | F | Cl | H | CH₃ | Br | |
| 1 | 2 | F | Br | H | CH₃ | Cl | |
| 1 | 2 | F | Br | H | C₂H₅ | Br | |
| 1 | 2 | F | Br | H | CH₂OH | Cl | |
| 1 | 2 | F | Br | H | CO₂CH₃ | Cl | |
| 1 | 2 | F | Br | CH₃ | CH₃ | Br | |
| 2 | 1 | F | Cl | H | H | Cl | |
| 2 | 1 | F | Cl | H | H | Br | |
| 2 | 1 | F | Cl | H | H | CN | |
| 2 | 2 | F | Cl | H | H | Cl | |
| 2 | 2 | F | Cl | H | H | Br | |
| 2 | 2 | F | Cl | H | H | CN | |
| 2 | 2 | F | Cl | H | CH₃ | Cl | |

TABLE 10-continued

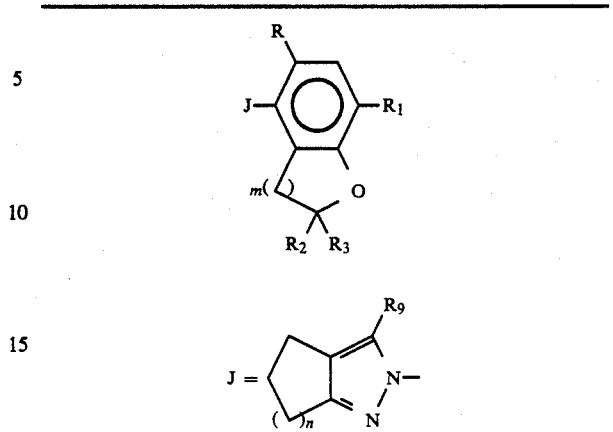

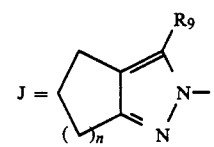

| m | n | R | R₁ | R₂ | R₃ | R₉ | m.p. (°C.) |
|---|---|---|----|----|----|----|-----------|
| 2 | 2 | F | Cl | H | C₂H₅ | Br | |
| 2 | 2 | F | Cl | H | CH₂OC(O)CH₃ | Cl | |
| 2 | 2 | F | Cl | H | CO₂C₂H₅ | CN | |
| 2 | 2 | F | Cl | CH₃ | CH₃ | Cl | |
| 2 | 2 | F | Br | H | H | Cl | |
| 2 | 2 | F | Br | H | CH₃ | Br | |
| 2 | 2 | F | Br | CH₃ | CH₃ | CN | |

TABLE II

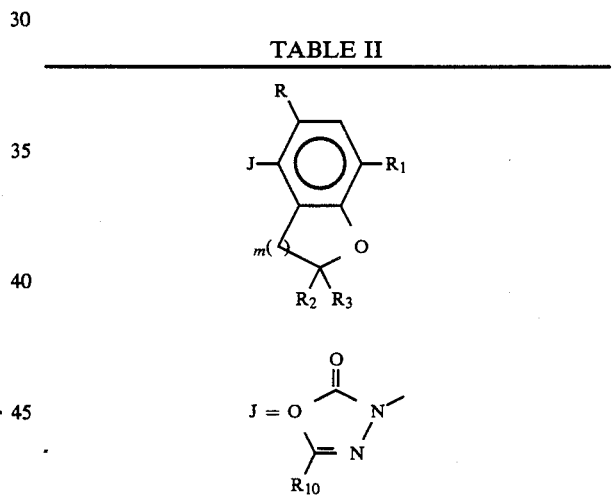

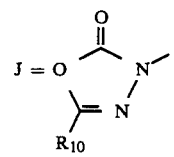

| m | R | R₁ | R₂ | R₃ | R₁₀ | m.p. (°C.) |
|---|---|----|----|----|-----|------------|
| 1 | F | Cl | H | CH₃ | CH₃ | |
| 1 | F | Cl | H | CH₃ | C₂H₅ | |
| 1 | F | Cl | H | CH₃ | C₃H₇ | |
| 1 | F | Cl | H | CH₃ | CH(CH₃)₂ | |
| 1 | F | Cl | H | CH₃ | C₄H₉ | |
| 1 | F | Cl | H | CH₃ | CH₂CH(CH₃)₂ | |
| 1 | F | Cl | H | CH₃ | CH(CH₃)C₂H₅ | |
| 1 | F | Cl | H | CH₃ | C(CH₃)₃ | |
| 1 | F | Cl | H | CH₃ | CH₂F | |
| 1 | F | Cl | H | CH₃ | CH₂CH₂Br | |
| 1 | F | Cl | H | CH₃ | CH₂CH₂CH₂Cl | |
| 1 | F | Cl | H | CH₃ | (CH₂)₃CH₂F | |
| 1 | H | Cl | H | CH₃ | C(CH₃)₃ | 79–81 |
| 1 | Cl | Cl | H | CH₃ | C(CH₃)₃ | 112–115 |
| 1 | F | Br | H | CH₃ | C(CH₃)₃ | |

TABLE 12

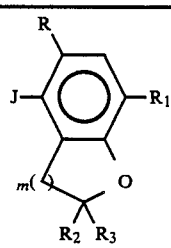

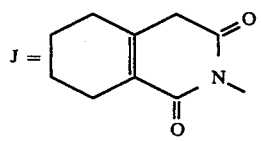

| m | R | R₁ | R₂ | R₃ | m.p. (°C.) |
|---|---|---|---|---|---|
| 1 | H | Cl | H | CH₃ | 188–191 |
| 1 | F | Cl | H | CH₃ | 124.5–126.5 |
| 1 | F | Cl | H | CH₂OH | |
| 1 | F | Cl | H | CO₂CH₃ | |
| 1 | F | Cl | CH₃ | CH₃ | |
| 1 | F | Br | H | CH₃ | |
| 1 | F | Br | H | CO₂CH₃ | |
| 2 | F | Cl | H | H | |
| 2 | F | Br | H | H | |

TABLE 13

$$J = CH_3-N\underset{O}{\overset{O}{\bigcirc}}N-$$

| m | R | R₁ | R₂ | R₃ | m.p. (°C.) |
|---|---|---|---|---|---|
| 1 | H | Cl | H | CH₃ | semi-solid |
| 1 | F | Cl | H | CH₃ | |
| 1 | F | Br | CH₃ | CH₃ | |

TABLE 14

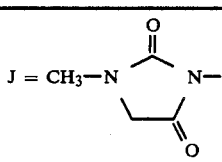

| m | R | R₁ | R₂ | R₃ | R₈ | R₁₀ | m.p. (°C.) |
|---|---|---|---|---|---|---|---|
| 1 | H | Cl | H | CH₃ | CH₃ | CF₂H | 122.5–123.5 |
| 1 | F | Cl | H | CH₃ | Cl | (CF₂)₃CH₃ | |
| 1 | F | Cl | H | CH₃ | CH₃ | CF₂H | |
| 1 | F | Cl | H | CH₃ | C₂H₅ | (CH₂)₂CH₃ | |
| 1 | F | Cl | H | CH₃ | C₃H₇ | C₂H₅ | |
| 1 | F | Cl | H | CH₃ | C(CH₃)₃ | CH₃ | |
| 1 | F | Cl | H | CH₃ | CF₂H | CF₂CHClF | |
| 1 | F | Cl | H | CH₃ | CH₂CH₂Cl | (CH₂)₃F | |

TABLE 14-continued

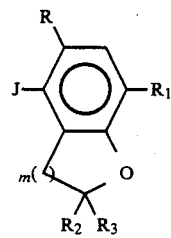

| m | R | R₁ | R₂ | R₃ | R₈ | R₁₀ | m.p. (°C.) |
|---|---|---|---|---|---|---|---|
| 1 | F | Cl | H | CH₃ | (CH₂)₃F | (CH₃)₄Br | |
| 1 | Cl | Cl | CH₃ | CH₃ | CH₃ | CF₂H | |
| 1 | F | Br | H | CO₂CH₃ | CH₃ | CF₂H | |
| 2 | F | Cl | H | H | CH₃ | CF₂H | |
| 2 | Cl | Cl | H | CH₃ | CH₃ | CF₂H | |
| 2 | F | Br | CH₃ | CH₃ | CH₃ | CF₂H | |

TABLE 15

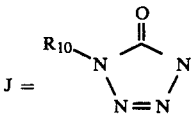

| m | R | R₁ | R₂ | R₃ | R₁₀ | m.p. (°C.) |
|---|---|---|---|---|---|---|
| 1 | F | Cl | H | CH₃ | CH₃ | |
| 1 | F | Cl | H | CH₃ | C₂H₅ | |
| 1 | F | Cl | H | CH₃ | C₃H₇ | |
| 1 | F | Cl | H | CH₃ | CH(CH₃)₂ | |
| 1 | F | Cl | H | CH₃ | C₄H₉ | |
| 1 | F | Cl | H | CH₃ | CF₂H | |
| 1 | F | Cl | H | CH₃ | CH₂CH₂Br | |
| 1 | F | Cl | H | CH₃ | (CH₂)₃F | |
| 1 | F | Cl | H | CH₃ | (CH₂)₄Cl | |
| 1 | F | Cl | H | CO₂CH₃ | (CH₂)₃F | |
| 1 | F | Cl | CH₃ | CH₃ | (CH₂)₃F | |
| 1 | Cl | Cl | H | C₂H₅ | (CH₂)₃F | |
| 1 | F | Br | H | CH₂OC(O)CH₃ | (CH₂)₃F | |
| 2 | F | Cl | H | H | (CH₂)₃F | |
| 2 | Cl | Cl | CH₃ | CH₃ | (CH₂)₃F | |
| 2 | F | Br | H | CO₂CH₃ | (CH₂)₃F | |
| 2 | F | Cl | H | H | CF₂H | |
| 2 | Cl | Cl | CH₃ | CH₃ | CF₂H | |
| 2 | F | Br | H | CO₂CH₃ | CF₂H | |

TABLE 16

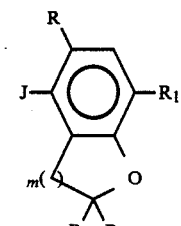

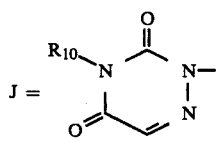

| m | R | R₁ | R₂ | R₃ | R₁₀ | m.p. (°C.) |
|---|---|----|----|----|-----|------------|
| 1 | H | Cl | H | CH₃ | CH₃ | 131–132 |
| 1 | F | Cl | H | CH₃ | C₂H₅ | |
| 1 | F | Cl | H | CH₃ | C₃H₇ | |
| 1 | F | Cl | H | CH₃ | CH(CH₃)₂ | |
| 1 | F | Cl | H | CH₃ | C₄H₉ | |
| 1 | F | Cl | H | CH₃ | CH₂F | |
| 1 | F | Cl | H | CH₃ | CH₂CH₂Br | |
| 1 | F | Cl | H | CH₃ | (CH₂)₃F | |
| 1 | F | Cl | H | CH₃ | (CH₂)₄Cl | |
| 1 | F | Cl | H | CH₃ | CH₃ | |
| 1 | F | Cl | H | CH₂OC(O)CH₃ | CH₃ | |
| 1 | F | Cl | CH₃ | CH₃ | CH₃ | |
| 1 | Cl | Cl | H | CO₂CH₃ | CH₃ | |
| 1 | F | Br | H | C₂H₅ | CH₃ | |
| 2 | F | Cl | H | H | CH₃ | |
| 2 | Cl | Cl | H | CH₃ | CH₃ | |
| 2 | F | Br | H | CO₂CH₃ | CH₃ | |

TABLE 17

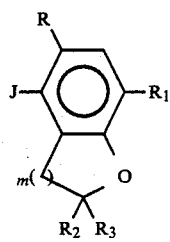

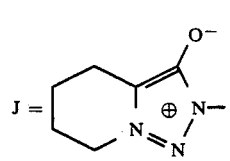

| m | R | R₁ | R₂ | R₃ | m.p. (°C.) |
|---|---|----|----|----|------------|
| 1 | F | Cl | H | CH₃ | |
| 1 | Cl | Cl | H | C₂H₅ | |
| 1 | F | Br | CH₃ | CH₃ | |
| 2 | F | Cl | H | H | |

TABLE 18

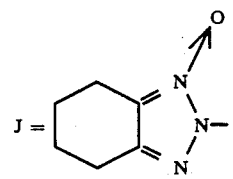

| m | R | R₁ | R₂ | R₃ | m.p. (°C.) |
|---|---|----|----|----|------------|
| 1 | F | Cl | H | CH₃ | |
| 1 | Cl | Cl | H | C₂H₅ | |
| 1 | F | Br | CH₃ | CH₃ | |
| 2 | F | Cl | H | H | |

TABLE 19

| m | R | R₁ | R₂ | R₃ | m.p. (°C.) |
|---|---|----|----|----|------------|

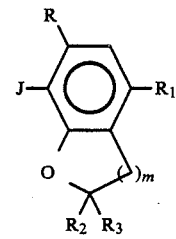

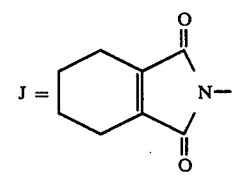

| 1 | H | H | H | H | 127–128 |
| 1 | F | Cl | H | CH₃ | |
| 1 | Cl | Cl | CH₃ | CH₃ | |
| 1 | F | Br | H | CO₂CH₃ | |
| 2 | F | Cl | H | H | |
| 2 | Cl | Cl | H | CH₃ | |
| 2 | F | Br | CH₃ | CH₃ | |

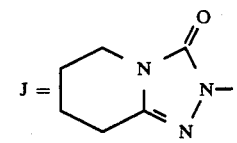

| 1 | F | Cl | H | CH₃ | |
| 1 | Cl | Cl | CH₃ | CH₃ | |
| 1 | F | Br | H | CO₂CH₃ | |
| 2 | F | Cl | H | H | |
| 2 | Cl | Cl | H | CH₃ | |
| 2 | F | Br | CH₃ | CH₃ | |

TABLE 20

| m | R | R₁ | R₂ | R₃ | m.p. (°C.) |
|---|---|----|----|----|------------|

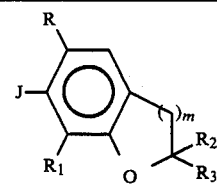

TABLE 20-continued

| m | R | $R_1$ | $R_2$ | $R_3$ | m.p. (°C.) |
|---|---|-------|-------|-------|------------|

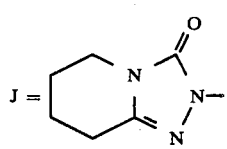

| m | R | $R_1$ | $R_2$ | $R_3$ | m.p. (°C.) |
|---|---|-------|-------|-------|------------|
| 1 | H  | H | H   | $CH_3$     | 114–118 |
| 1 | F  | H | H   | $CH_3$     |         |
| 1 | F  | H | $CH_3$ | $CH_3$  |         |
| 1 | F  | H | H   | $CO_2CH_3$ |         |
| 2 | F  | H | H   | H          |         |
| 2 | F  | H | H   | $CH_3$     |         |
| 2 | F  | H | $CH_3$ | $CH_3$  |         |

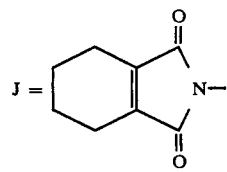

| m | R | $R_1$ | $R_2$ | $R_3$ | m.p. (°C.) |
|---|---|-------|-------|-------|------------|
| 1 | F  | H | H     | $CH_3$     |  |
| 1 | Cl | H | $CH_3$ | $CH_3$    |  |
| 1 | F  | H | H     | $CO_2CH_3$ |  |
| 2 | F  | H | H     | H          |  |
| 2 | Cl | H | H     | $CH_3$     |  |
| 2 | F  | H | $CH_3$ | $CH_3$    |  |

TABLE 21

| m | R | $R_1$ | $R_2$ | $R_3$ | m.p. (°C.) |
|---|---|-------|-------|-------|------------|

(Structure with R, J, $R_1$, $R_2$, $R_3$ on benzene ring)

(Second structure: fused bicyclic imide)

| 1 | H  | H | H     | H              | 165–167 |
| 1 | H  | H | $CH_3$ | $CH_3$        | 144–146 |
| 1 | H  | H | H     | $CH_3$         | 140–143 |
| 1 | H  | H | H     | $CH_2OH$       | 140–145 |
| 1 | H  | H | H     | $CO_2C(CH_3)_3$ | yellow foam |
| 1 | H  | H | H     | $CO_2H$        | 179–181 |
| 1 | H  | H | H     | $CO_2CH_3$     | yellow foam |
| 1 | H  | H | H     | $CON(CH_3)_2$  | yellow foam |
| 1 | H  | H | H     | $CH_2OC(O)CH_3$ | 142–144 |
| 1 | F  | H | H     | $CH_3$         |  |
| 1 | F  | H | $CH_3$ | $CH_3$        |  |
| 2 | F  | H | H     | H              |  |
| 2 | F  | H | H     | $CH_3$         |  |
| 2 | F  | H | $CH_3$ | $CH_3$        |  |

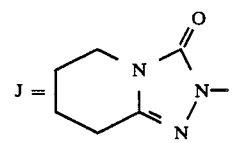

| 1 | F  | H | H     | $CH_3$     |  |
| 1 | Cl | H | $CH_3$ | $CH_3$    |  |
| 1 | F  | H | H     | $CO_2CH_3$ |  |

TABLE 21-continued

| m | R | $R_1$ | $R_2$ | $R_3$ | m.p. (°C.) |
|---|---|-------|-------|-------|------------|
| 2 | F  | H | H     | H      |  |
| 2 | Cl | H | H     | $CH_3$ |  |
| 2 | F  | H | $CH_3$ | $CH_3$ |  |

Formulations

Useful formulations of the compounds of Formula I can be prepared in Cconventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE 22

|  | Active Ingredient | Weight Percent* | |
|---|---|---|---|
|  |  | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., Mcgraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE A

| Wettable Powder | |
|---|---|
| ((1,2,4))triazolo((4,3-A))pyridin-3(2H)-one, 2-(5,7-dichloro-2,3-dihydro-2-methyl-4-benzofuranyl)-5,6,7,8-tetrahydro | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 micros, blended, and packaged.

EXAMPLE B

| Low Strength Granule | |
|---|---|
| ((1,2,4))triazolo((4,3-A))pyridin-3(2H)-one, 2-(5,7-dichloro-2,3-dihydro-2-methyl-4-benzofuranyl)-5,6,7,8-tetrahydro | 1% |
| N,N-dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE C

| | |
|---|---|
| ((1,2,4))triazolo((4,3-A))pyridin-3(2H)-one, 2-(5,7-dichloro-2,3-dihydro-2-methyl-4-benzofuranyl)-5,6,7,8-tetrahydro | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground in a sand mill to produce particles essentially all under 5 microns in size.

EXAMPLE D

| Granule | |
|---|---|
| ((1,2,4))triazolo((4,3-A))pyridin-3(2H)-one, 2-(5,7-dichloro-2,3-dihydro-2-methyl-4-benzofuranyl)-5,6,7,8-tetrahydro | 80% |
| wetting agent | 1% |
| crude ligninsulfonate salt (containing 5–20 of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE E

| High Strength Concentrate | |
|---|---|
| ((1,2,4))triazolo((4,3-A))pyridin-3(2H)-one, 2-(5,7-dichloro-2,3-dihydro-2-methyl-4-benzofuranyl)-5,6,7,8-tetrahydro | 99% |
| silica aerogel | 0.5% |
| synthetic amorhous silica | 0.5% |

The ingredients are blended and ground in a hammer-mill to produce a material essentially all passing a U.S.S. No. 50 screen (0.3 mm opening). The concentrate may be formulated further if necessary.

EXAMPLE F

| Extruded Pellet | |
|---|---|
| ((1,2,4))triazolo((4,3-A))pyridin-3(2H)-one, 2-5,7-dichloro-2,3-dihydro-2-methyl-4-benzofuranyl)-5,6,7,8-tetrahydro | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be crushed to pass a U.S.S. No. 10 sieve (0.84 mm openings). The granules held on a U.S.S. No. 40 sieve (0.42mm openings) may be packaged for use and the fines recycled.

EXAMPLE G

| Oil Suspension | |
|---|---|
| ((1,2,4))triazolo((4,3-A))pyridin-3(2H)-one, 2-(5,7-dichloro-2,3-dihydro-2-methyl-4-benzofuranyl)-5,6,7,8-tetrahydro | 25% |

| Oil Suspension | |
|---|---|
| polyoxyethylene sorbitol hexoleate | 5% |
| highly aliphatic hydrocarbon oil | 70% |

The ingredient are ground together in a sand mill until the mold particles have been reduced to under about 5 microns. The resulting thick suspension may be applied directly, but preferably after being extended with oils or emulsified in water.

EXAMPLE H

| Dust | |
|---|---|
| ((1,2,4))triazolo((4,3-A))pyridin-3(2H)-one, 2-(5,7-dichloro-2,3-dihydro-2-methyl-4-benzofuranyl)-5,6,7,8-tetrahydro | 10% |
| attapulgite | 10% |
| pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE I

| Emulsifiable Concentrate | |
|---|---|
| ((1,2,4))triazolo((4,3-A))pyridin-3(2H)-one, 2-(5,7-dichloro-2,3-dihydro-2-methyl-4-benzofuranyl)-5,6,7,8-tetrahydro | 20% |
| chlorobenzene | 74% |
| sorbitan monostearate and polyoxyethylene condensates thereof | 6% |

The ingredients are combined and stirred to produce a solution which can be emulsified in water for application.

Utility

Test results indicate that the compounds of the present invention are active herbicides. They have utility for broad-spectrum pre- and/or post-emergence weed control in areas where complete control of all vegetation is desired, such as around industrial storage areas, parking lots, drive-in theaters, around billboards, highway and railroad structures. Some of the compounds have utility for selective weed control in crops such as rice, wheat, barley, corn, soybeans, sugarbeets and cotton. Alternatively, the subject compounds are useful to modify plant growth.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.001 to 20 kg/ha, the lower rates being suggested for use on lighter soils and/or those having a low organic matter content, for plant growth modification or for situations where only short-term persistence is required, such as a herbicide for fallow land.

The compounds of the invention may be used in combination with any other commercial herbicide, non-limiting examples of which are listed below.

| Common Name | Chemical Name |
|---|---|
| acetochlor | 2-chloro-B-(ethoxymethyl)-N-(2-ethyl-6-methylphenyl)acetamide |
| acifluorfen | 5-[2-chloro-4-(trifluoromethyl)phenoxy]-2-nitrobenzoic acid |
| acrolein | 2-propenal |
| alachlor | 2-chloro-2,6-diethylphenyl-N-(methoxy methyl)acetanilide |
| ametryn | N-ethyl-N'-1(1-methylethyl)-6-(methylthio)-1,3,5-triazine-2,4-diamine |
| amitrole | 1H-1,2,4-triazol-3-amine |
| AMS | ammonium sulfamate |
| asulam | methyl [(4-aminophenyl)sulfonyl]carbamate |
| atrazine | 6-chloro-N-ethyl-N'-(1-methylethyl)-1,3,5-triazine-2,4-diamine |
| barban | 4-chloro-2-butynyl 3-chlorophenylcarbamate |
| benefin | N-butyl-N-ethyl-2,6-dinitro-4-(trifluoromethyl)benzenamine |
| bensulfuron methyl | 2-methyl-[[[[[(4,6-dimethoxy-2-pyrimidinyl)-amino]carbonyl]amino]sulfonyl]methyl]-benzoic acid, methyl ester |
| bensulide | O,O-bis(1-methylethyl) S-[2-[(phenylsulfonyl)-amino]ethyl]phosphorodithioate |
| bentazon | 3-(1-methylethyl)-(1H)-2,1,3-benzothiadiazin0 4(3H)-one, 2,2-dioxide |
| benzofluor | N-[4-(ethylthio)-2-(trifluoromethyl)phenyl]-methanesulfonamide |
| benzoylprop | N-benzoyl-N-(3,4-dichlorophenyl)-DL-alaine |
| bifenox | methyl 5-(2,4-dichlorophenoxy)-2-nitrobenzoate |
| bromacil | 5-bromo-6-methyl-3-(1-methylpropyl)-2,4-(1H,3H)pyrimidinedione |
| bromoxynil | 3,5-dibromo-4-hydroxybenzonitrile |
| butachlor | N-(butoxymethyl)-2-chloro-N-(2,6-diethyl-phenyl)acetamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| butylate | S-ethyl-bis(2-methylpropyl)carbamothioate |
| cacodylic acid | dimethyl arsinic acid |
| CDAA | 2-chloro-N,N-di-2-propenylacetamide |
| CDEC | 2-chloroallyl diethyldithiocarbamate |
| chloramben | 3-amino-2,5-dichlorobenzoic acid |
| chlorbromuron | 3-(4-bromo-3-chlorophenyl)-1-methoxy-1-methylurea |
| chlorimuron ethyl | 2-[[[[(4-chloro-6-methoxy-2-pyrimidinyl)-amino]carbonyl]amino]sulfonyl]benzoic-acid, ethyl ester |
| chloroxuron | N'-[4-(4-chlorophenoxy)phenyl]-N,N-dimethylurea |
| chlorpropham | 1-methylethyl 3-chlorophenylcarbamate |
| chlorsulfuron | 2-chloro-N-[(4-methoxy-6-methyl-1,3,5-triazin-2-yl)amino]carbonyl]benzene-sulfonamide |
| chlortoluron | N'-(3-chloro-4-methylphenyl)-N,N-dimethylurea |
| cinmethylin | exo-1-methyl-4-(1-methylethyl)-2-[(2-methylphenyl)methoxy]-7-oxabicyclo[2.2.1]heptane |
| clethodim | (E,E)-(±)-2-[[(3-chloro-2-propenyl)oxy]-imino]propyl]-5-[2-(ethylthio)-propyl]-3-hydroxy-2-cyclohexan-1-one |
| clomazone | 2-[(2-chlorophenyl)methyl]-4,4-dimethyl-3-isoxazolidinone |
| cloproxydim | (E,E)-2-[1-[[(3-chloro-2-propenyl)oxy) imino]butyl]-5-[2-(ethylthio)propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-triazin-2-yl]amino]-2-methyl-propanenitrile |
| cycloate | S-ethyl cyclohexylethylcarbamothioate |
| cycluron | 3-cyclooctyl-1,1-dimethylurea |

-continued

| Common Name | Chemical Name |
|---|---|
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropionic acid |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmediphan | ethyldesmetryn[3-[[(phenylamino)-carbonyl]oxy]phenyl]carbamate |
| desmetryn | 2-(isopropylamino)-4-(methylamino)-6-methylthio)-s-triazine |
| diallate | S-(2,3-dichloro-2-propenyl) bis(1-methylethyl)carbamothioate |
| dicamba | 3,6-dichloro-2-methoxybenzoic acid |
| dichlobenil | 2,6-dichlorobenzonitrile |
| dichlorprop acid | ($\pm$)-2-(2,4-dichlorophenoxy)propanoic |
| diclofop | ($\pm$)-2-[4-(2,4-dichlorophenoxy)phenoxy]-propanoic acid |
| diethatyl | N-(chloroacetyl)-N-(2,6-diethylphenyl)-glycine |
| difenzoquat | 1,2-dimethyl-3,5-diphenyl-1H-pyrazolium |
| dinitramine | $N^3,N^3$-diethyl-2,4-dinitro-6-(trifluoromethyl)-1,3-benzenediamine |
| dinoseb | 2-(1-methylpropyl)-4,6-dinitrophenol |
| diphenamide | N,N-dimethyl-$\alpha$-phenylbenzeneacetamide |
| dipropetryn | 6-(ethylthio)-N,N'-bis(1-methylethyl)-1,3,5-triazine-2,4-diamine |
| diquat | 6,7-dihydrodipyrido[1,2-a:2',1'-c]-pyrazinediium ion |
| diuron | N'-(3,4-dichlorophenyl)-N,N-dimethylurea |
| DNOC | 2-methyl-4,6-dinitrophenol |
| DPX-M6316 | 3-DSMA[[[[(4-methoxy-6-methyl-1,3,5-triazin-2-yl)amino]carbonyl]amino]-sulfonyl]-2-thiophenecarboxylic acid, methyl ester |
| DSMA | disodium salt of MAA |
| endothall | 7-oxabicyclo[2.2.1]heptane-2,3-dicarboxylic acid |
| EPTC | S-ethyl dipropylcarbamothioate |
| ethafluralin | N-ethyl-N-(2-methyl-2-propenyl)-2,6-dinitro-4-(trifluoromethyl)benzenamine |
| ethofumesate | ($\pm$)-2-ethoxy-2,3-dihydro-3,3-dimethyl-5-benzofuranyl methanesulfonate |
| Express ® | 2-[[[[N-(4-methoxy-6-methyl-1,3,5-triazine-2-yl)-N-methylamino]-carbonyl]amino]sulfonyl]benzoic acid, methyl ester |
| fenac | 2,3,6-trichlorophenylacetic acid |
| fenoxaprop | ($\pm$)-2-[4-[6-chloro-2-benzoxazolyl-oxy]phenoxy]propanoic acid |
| fenuron | N,N-dimethyl-N'-phenylurea |
| fenuron TCA | Salt of fenuron and TCA |
| flamprop | N-benzoyl-N-(3-chloro-4-fluorophenyl)-DL-alanine |
| fluazifop | ($\pm$)-2-[4-[[5-(trifluoromethyl)-2-pyridinyl]oxy]phenoxy]propanoic acid |
| fluazifop-P | (R)-2-[4-[[5-(trifluoromethyl)-2-pyridinyl]oxy]phenoxy]propanoic acid |
| fluchloralin | N-(2-chloroethyl)-2,6-dinitro-N-propyl-4-(trifluoromethyl)benzenamine |
| fluometuron | N,N-dimethyl-N'-[3-trifluoromethyl)phenyl]urea |
| fluorochloridone | 3-chloro-4-(chloromethyl)-1-[3-(trifluoromethyl)phenyl]-2-pyrrolidinone |
| fluorodifen | p-nitrophenyl a,a,a-trifluoro-2-nitro-p-tolyl ether |
| fluoroglycofen | carboxymethyl 5-[2-chloro-4-(trifluoromethyl)phenoxy]-2-nitrobenzoate |
| fluridone | 1-methyl-3-phenyl-5-[3-(trifluoromethyl)phenyl]-4(1H)-pyridinone |
| fomesafen | 5-[2-chloro-4-trifluoromethyl)phenoxy]-N-(methylsulfonyl)-2-nitrobenzamide |
| fosamine | ethyl hydrogen (aminocarbonyl)phosphate |
| glyphosate | N-(phosphonomethyl)glycine |
| halozyfop | 2-[4-[[3-chloro-5-(trifluoromethyl)-2-pyridinyl]oxy]phenoxy]propanoic acid |
| hexaflurate | potassium hexafluoroarsenate |
| hexazinone | 3-cyclohexyl-6-(dimethylamino)-1-methyl-1,3,5-triazine-2,4(1H,3H)-dione |
| imazamethabenz | 6-(4-isopropyl-4-methyl-5-oxo-2-imidazolin-2-yl)-p-toluic acid, methyl ester |
| imazapyr | ($\pm$)-[4,5-dihydro-4-methyl-4-(1-methylethyl-5-oxo-1H-imidazol-2-yl[-3-pyridinecarboxylic acid |
| imazaquin | 2-[4,5-dihydro-4-methyl-4-(1-methylethyl)-5-oxo-1H-imidazol-2-yl]-3-quinolinecarboxylic acid |
| imazethapyr | ($\pm$)-2-[4,5-dihydro-4-methyl-4-(1-methyl ethyl)-5-oxo-1H-imidazol-2-yl]-5-ethyl-3-pyridinecarboxylic acid |
| ioxynil | 4-hydroxy-3,5-diiodobenzonitrile |
| isopropalin | 4-(1-methylethyl)-2,6-dinitro-N,N-dipropylbenzenamine |
| isoproturon | N-(4-isopropylphenyl)-N',N'-dimethylurea |
| isouron | N'-[(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]-phenyl (1,1-dimethylethyl)-carbamate |
| lactofen | ($\pm$)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-1H-cyclopenta-pyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPB | 4-(4-chloro-2-methylphenoxy)butanoic acid |
| mecoprop | ($\pm$)-2-(4-chloro-2-methylphenoxy)-propanoic acid |
| mefluidide | N-[2,4-dimethyl-5-[[(trifluoromethyl)-sulfonyl]amino]phenyl]acetamide |
| methalpropalin | N-(2-methyl-2-propenyl)-2,6-dinitro-N-propyl-4-(trifluoromethyl)benzenamide |
| methabenzthiazuron | 1,3-dimethyl-3-(2-benzothiazolyl)urea |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)-N,N-dimethylurea |
| metolachlor | 2-chloro-N-(2-ethyl-6-methylphenyl)-N-(2-methoxy-1-methylethyl)acetamide |
| metribuzin | 4-amino-6-(1,1-dimethylethyl)-3-(methylthio)-1,2,4-triazin-5(4H)-one |
| metsulfuron | 2-[[[[(4-methoxy-6-methyl-1,3,5-triazin-2-yl)amino]carbonyl]amino]-sulfonyl]benzoic acid, methyl ester |
| MH | 1,2-dihydro-3,6-pyridazinedione |
| molinate | S-ethyl hexahydro-1H-azepine-1-carbothioate |
| monolinuron | 3-(p-chlorophenyl)-1-methoxy-1-methylurea |
| monuron | N'-(4-chlorophenyl)-N,N-dimethylurea |
| monuron TCA | salt of monuron and TCA |
| MSMA | monosodium salt of MAA |
| napropamide | N,N-diethyl-2-(1-naphthalenyloxy)-propanamide |
| naptalam | 2-[(1-naphthalenylamino)carbonyl]-benzoic acid |
| neburon | 1-butyl-3-(3,4-dichlorophenyl)-1-methylurea |
| nitralin | 4-(methylsulfonyl)-2,6-dinitro-N,N- |

| Common Name | Chemical Name |
|---|---|
| | dipropylaniline |
| nitrofen | 2,4-dichloro-1-(4-nitrophenoxy)benzene |
| nitrofluorfen | 2-chloro-1-(4-nitrophenoxy)-4-(trifluoromethyl)benzene |
| norea | N,N-dimethyl-N'-(octahydro-4,7-methano-1H-inden-5-yl)urea 3aα,4α,5α,7α,7aα-isomer |
| norflurazon | 4-chloro-5-(methylamino)-2-[3-(trifluoromethyl)phenyl]-3(2H)-pyridazinone |
| oryzalin | 4-(dipropylamino)-3,5-dinitrobenzenesulfonamide |
| oxadiazon | 3-[2,4-dichloro-5-(1-methylethoxy)phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methanesulfonamide |
| phenmedipham | 3-[(methoxycarbonyl)amino]phenyl-(3-methylphenyl)carbamate |
| picloram | 4-amino-3,5,6-trichloro-2-pyridinecarboxylic acid |
| PFG-1013 | 5-(2-chloro-4-(trifluoromethyl)phenoxy)-2-nitroacetophenone oxime-O-acetic acid, methyl ester |
| procyazine | 2-[[4-chloro-6-(cyclopropylamino)-1,3,5-triazine-2-yl]amino]-2-methylpropanenitrile |
| profluralin | N-(cyclopropylmethyl)-2,6-dinitro-N-propyl-4-(trifluoromethyl)benzenamine |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro N-(1,1-dimethyl-2-propynyl)benzamide |
| propachlor | 2-chloro-N-(1-methylethyl)-N-phenylacetamide |
| propanil | N-(3,4-dichlorophenyl)propanamide |
| propazine | 6-chloro-N,N'-bis(1-methylethyl)-1,3,5-triazine-2,4-diamine |
| propham | 1-methylethyl phenylcarbamate |
| prosulfalin | N-[[4-(dipropylamino)-3,5-dinitrophenyl]sulfonyl]-S,S-dimethylsulfilimine |
| prynachlor | 2-chloro-N-(1-methyl-2-propynyl)acetanilide |
| pyrazon | 5-amino-3-chloro-2-phenyl-3(2H)-pyridazinone |
| quizalofop ethyl | (±)-2-[4[(6-chloro-2-quinoxalinyl)]oxy]phenoxy]propanoic acid, ethyl ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexene-1-one |
| siduron | N-(2-methylcyclohexyl)-N'-phenylurea |
| simazine | 6-chloro-N,N'-diethyl-1,3,5-triazine-2,4-diamine |
| sulfometuron methyl | 2-[[[[(4,6-dimethyl-2-pyrimidinyl)amino]carbonyl]amino]sulfonyl]-benzoic acid, methyl ester |
| TCA | trichloroacetic acid |
| tebuthiuron | N-[5-(1,1-dimethylethyl)-1,3,4-thiadiazol-1-2-yl]-N,N'-dimethylurea |
| terbacil | 5-chloro-3(1,1-dimethylethyl)-6-methyl-2,4(1H,3H)-pyrimidinedione |
| terbuchlor | N-(butoxymethyl)-2-chloro-N-[2-(1,1-dimethylethyl)-6-methylphenyl]-acetamide |
| terbuthylazine | 2-(tert-butylamino)-4-chloro-6-(ethylamino)-s-triazine |
| terbutol | 2,6-di-tert-butyl-p-tolyl methylcarbamate |

| Common Name | Chemical Name |
|---|---|
| terbutryn | N-1,1-dimethylethyl)-N'-ethyl-6-methylthio)-1,3,5-triazine-2,4-diamine |
| thiameturon methyl | 3-[[[[(4-methoxy-6-methyl-1,3,5-triazin-2-yl)amino]carbonyl]amino]-sulfonyl]2-thiophenecarboxylic acid, methyl ester |
| thiobencarb | S-[(4-chlorophenyl)methyl]diethylcarbamothioate |
| triallate | S-(2,3,3-trichloro-2-propenyl)bis(1-methylethyl)carbamothioate |
| triclopyr | [(3,5,6-trichloro-2-pyridinyl)oxy]acetic acid |
| tridiphane | 2-(3,5-dichlorophenyl)-2-(2,2,2-trichloroethyl)oxirane |
| trifluralin | 2,6-dinitro-N,N-dipropyl-4-(trifluoromethyl)benzenamine |
| trimeturon | 1-(p-chlorophenyl)-2,3,3-trimethylpseudourea |
| 2,4-D | (2,4-dichlorophenoxy)acetic acid |
| 2,4-DB | 4-(2,4-dichlorophenoxy)butanoic acid |
| vernolate | S-propyl dipropylthiocarbamothioate |
| xylachlor | 2-chloro-N-(2,3-dimethylphenyl)-N-(1-methylethyl)acetamide |

The herbicidal properties of the subject compounds were discovered in a number of greenhouse tests. The test procedures and results follow.

BIOLOGICAL TABLES

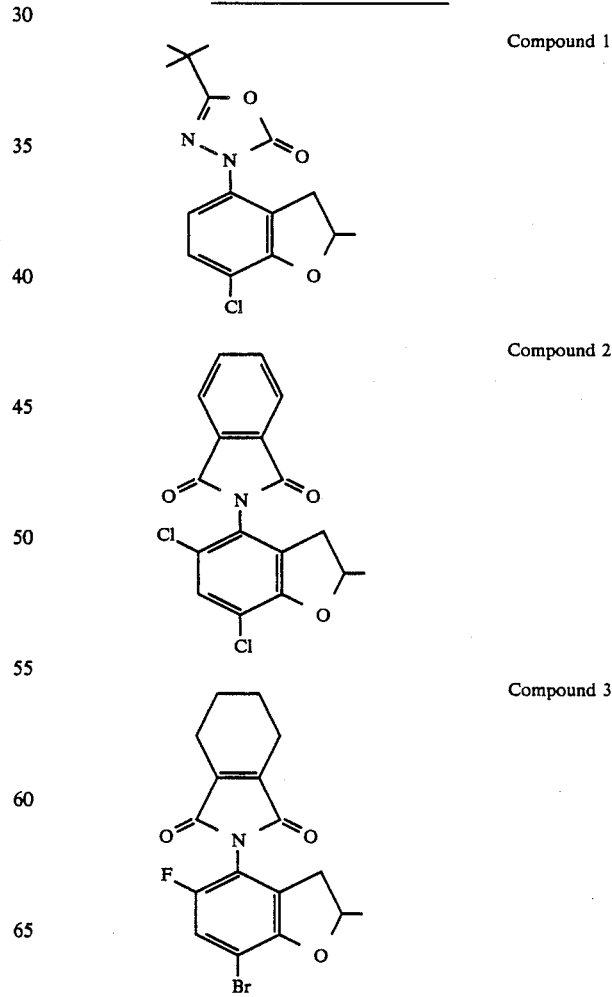

Compound 1

Compound 2

Compound 3

-continued
BIOLOGICAL TABLES
Compound 4
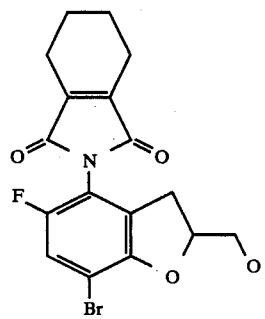
Compound 5
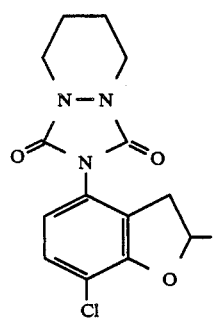
Compound 6
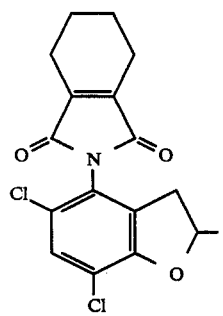
Compound 7
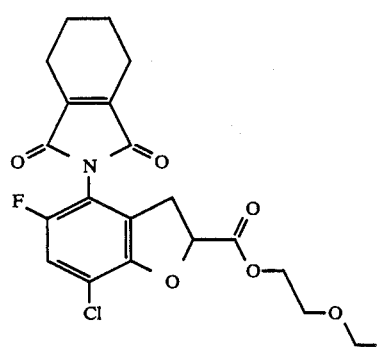
-continued
BIOLOGICAL TABLES
Compound 8
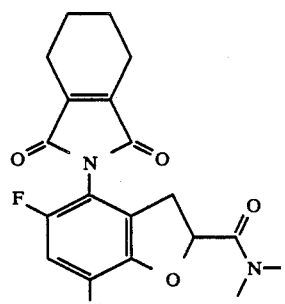
Compound 9
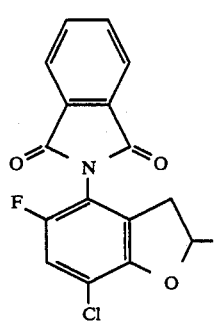
Compound 10
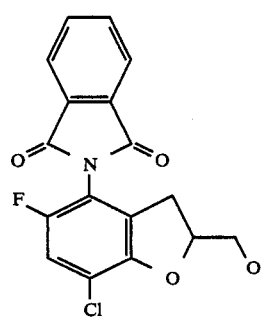
Compound 11
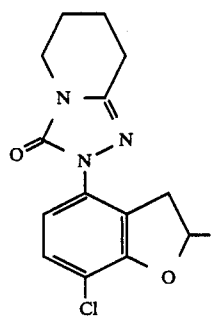
Compound 12
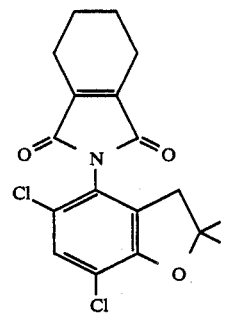

-continued
BIOLOGICAL TABLES
Compound 13
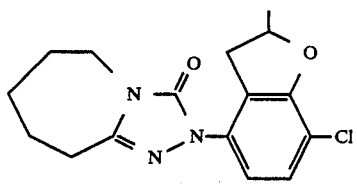
Compound 14
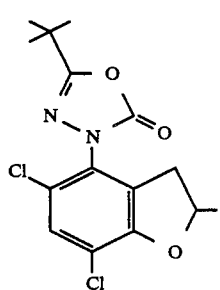
Compound 15
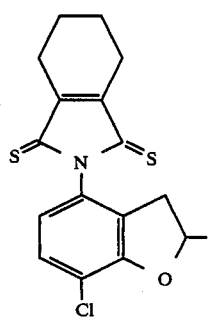
Compound 16
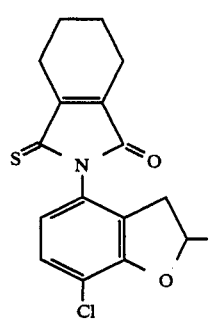
Compound 17
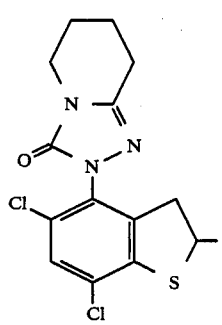
-continued
BIOLOGICAL TABLES
Compound 18
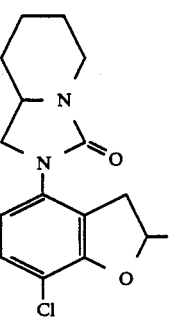
Compound 19
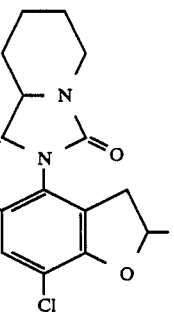
Compound 20
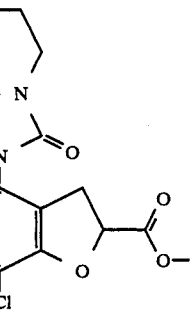
Compound 21
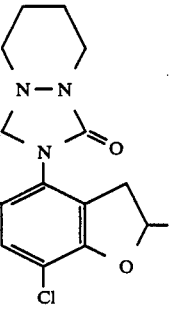
Compound 22
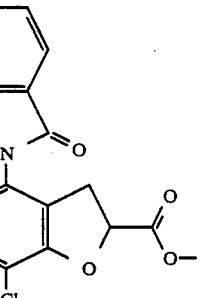

-continued
BIOLOGICAL TABLES
Compound 23
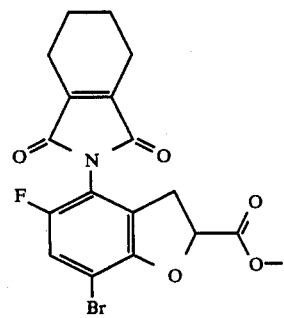
Compound 24
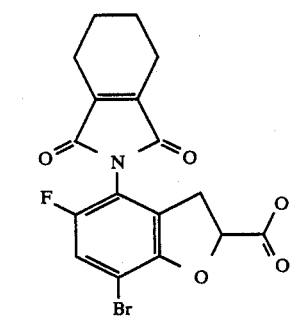
Compound 25
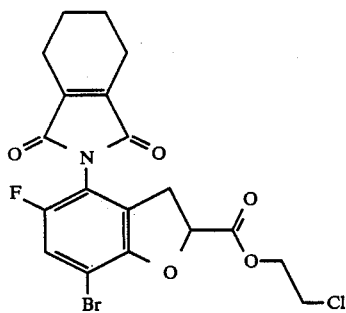
Compound 26
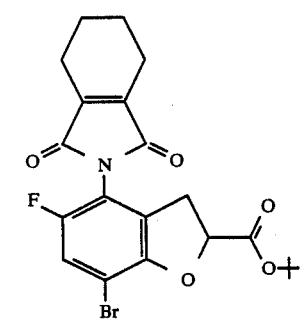
-continued
BIOLOGICAL TABLES
Compound 27
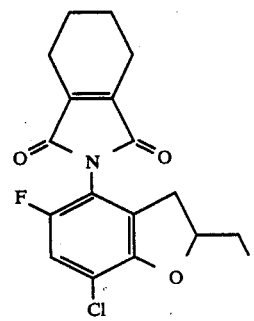
Compound 28
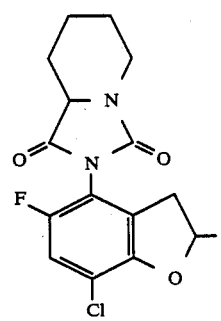
Compound 29
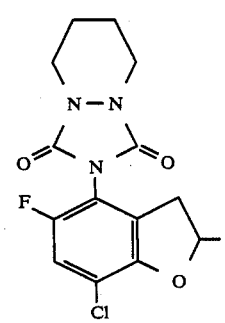
Compound 30
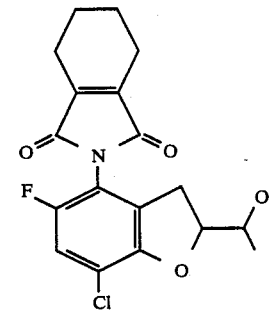
Compound 31
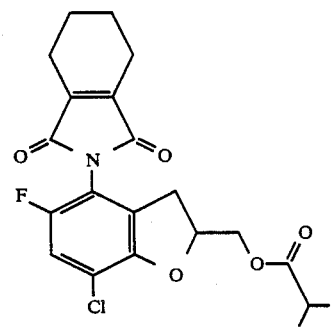

-continued
BIOLOGICAL TABLES
Compound 32
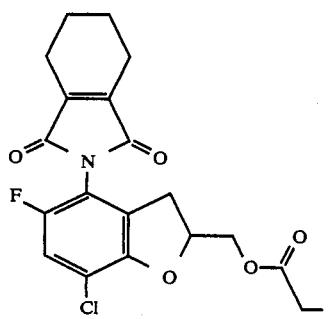
Compound 33
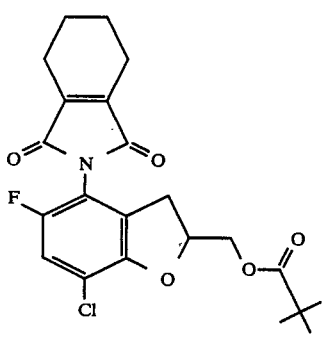
Compound 34
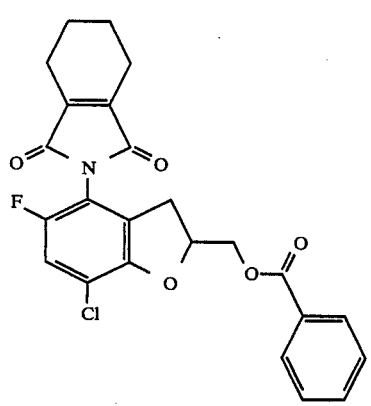
Compound 35
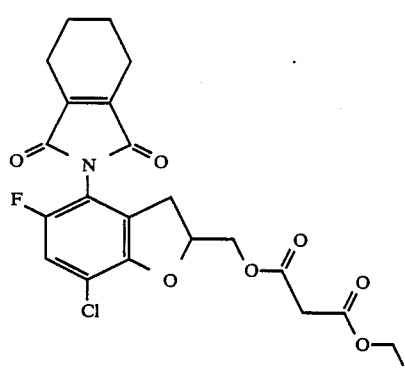
-continued
BIOLOGICAL TABLES
Compound 36
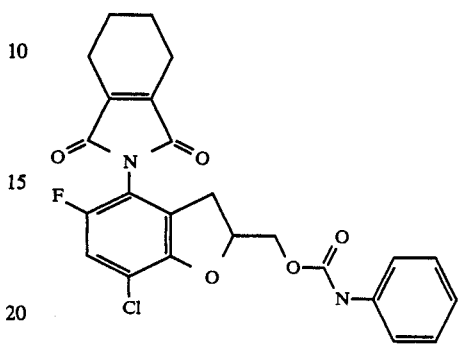
Compound 37
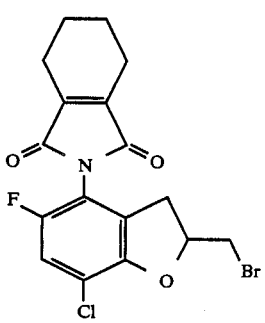
Compound 38
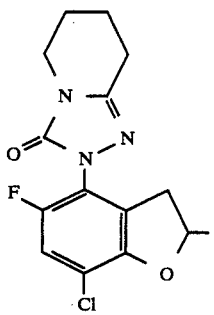
Compound 39
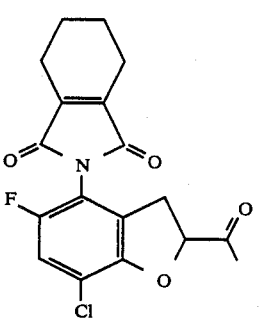

-continued
BIOLOGICAL TABLES
Compound 40
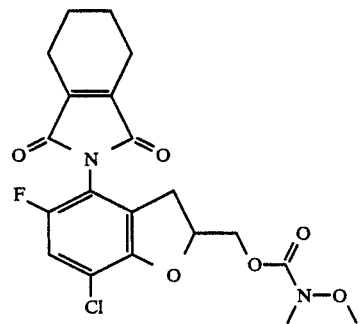
Compound 41
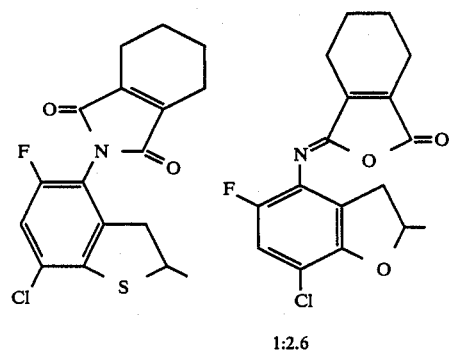
1:2.6
Compound 42
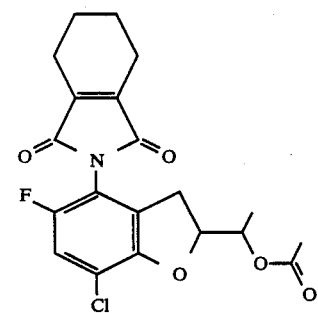
Compound 43
-continued
BIOLOGICAL TABLES
Compound 44
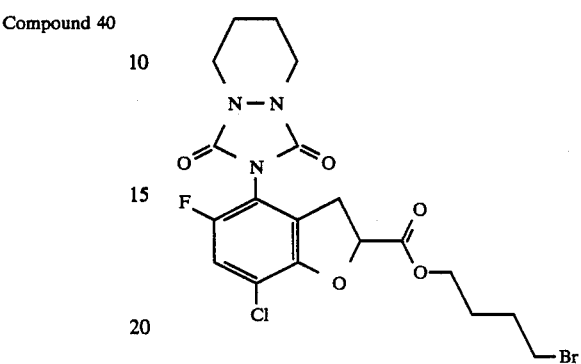
Compound 45
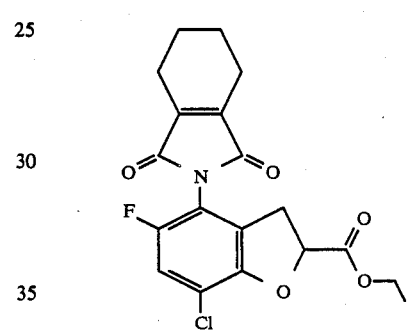
Compound 46
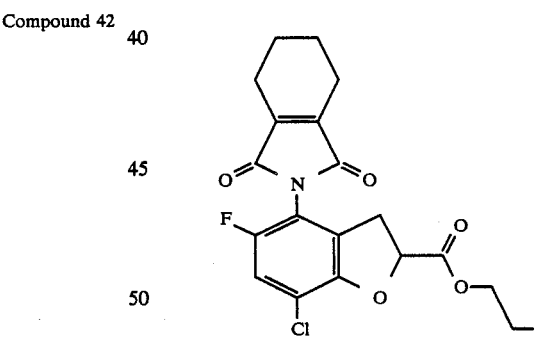
Compound 47
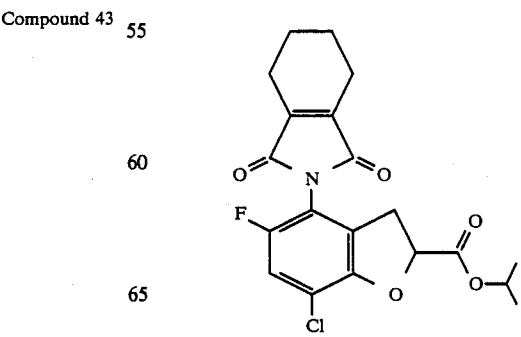

-continued
BIOLOGICAL TABLES
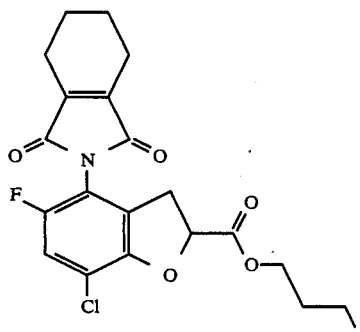
Compound 48
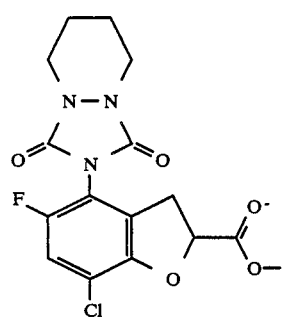
Compound 49
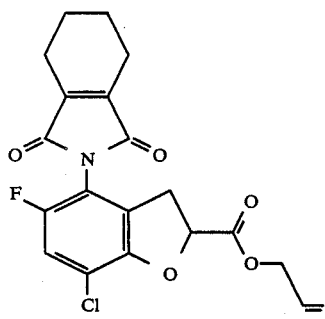
Compound 50
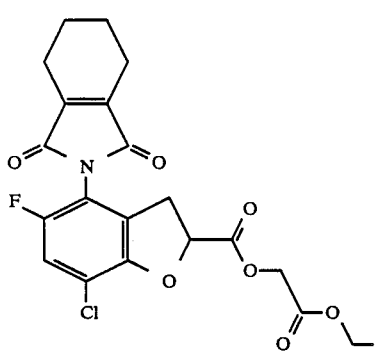
Compound 51
-continued
BIOLOGICAL TABLES
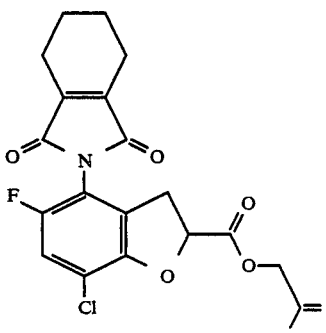
Compound 52
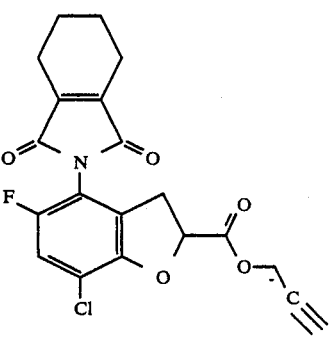
Compound 53
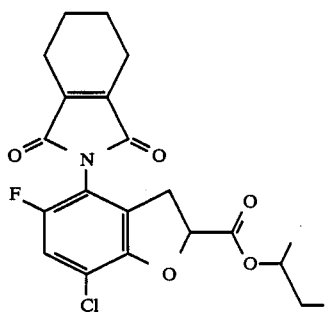
Compound 54
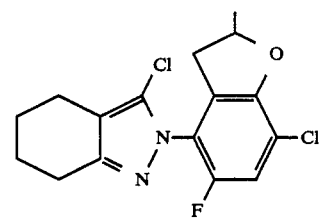
Compound 55
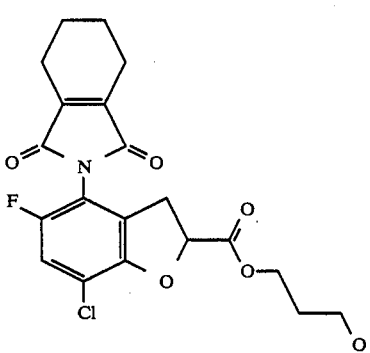
Compound 56

BIOLOGICAL TABLES
Compound 57
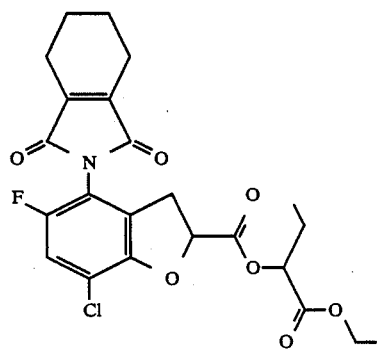
Compound 58
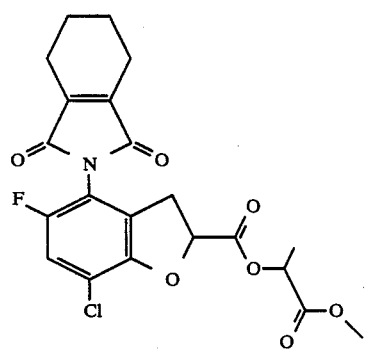
Compound 59
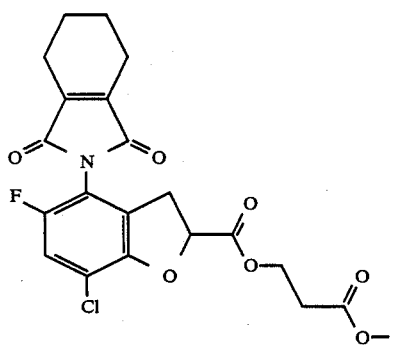
Compound 60
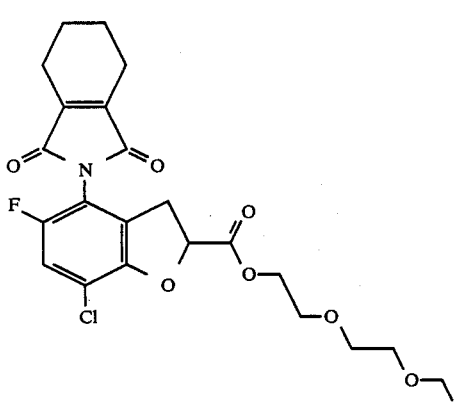
Compound 61
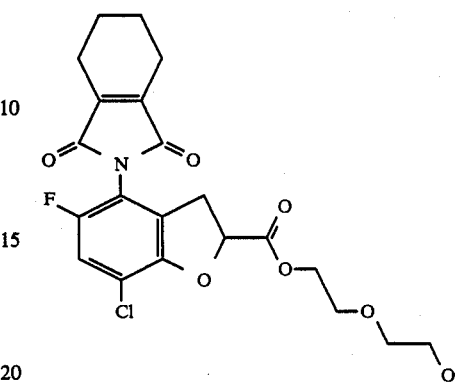
Compound 62
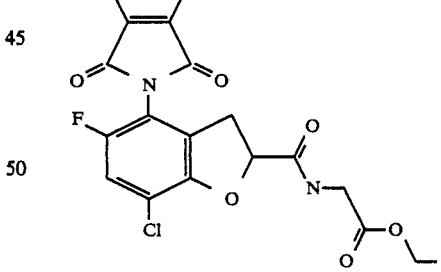
Compound 63
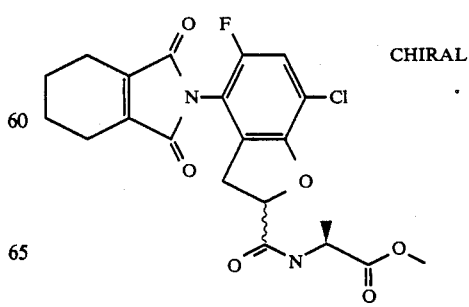
Compound 64
CHIRAL -continued
BIOLOGICAL TABLES
Compound 65
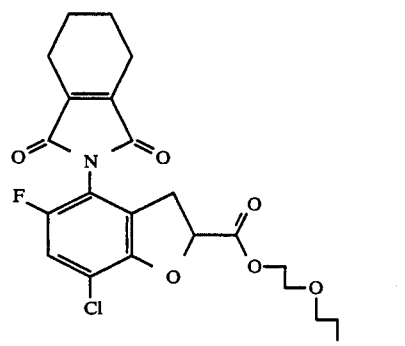
Compound 66
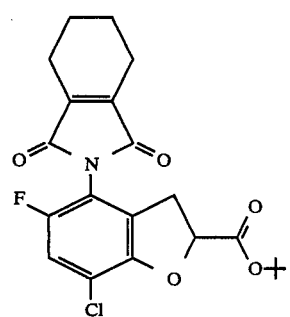
Compound 67
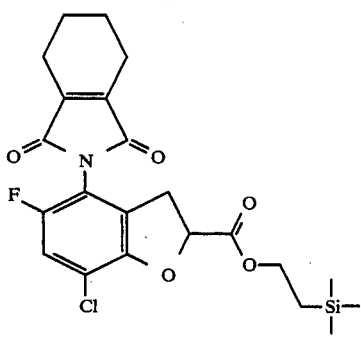
Compound 68
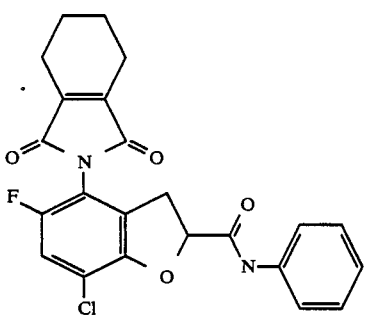
-continued
BIOLOGICAL TABLES
Compound 69
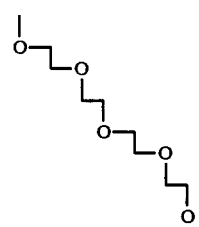
Compound 70
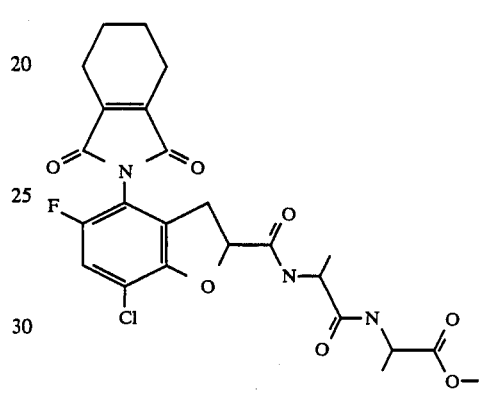
Compound 71
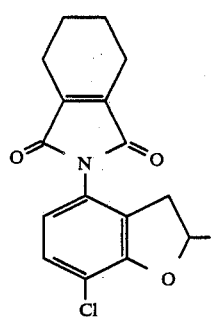
Compound 72
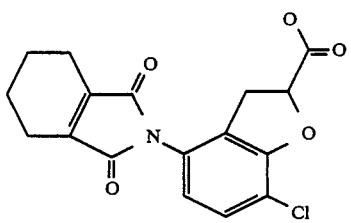
Compound 73
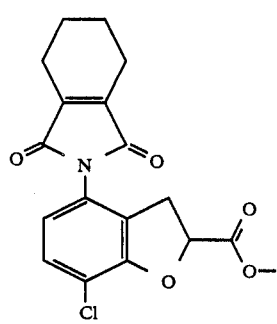

Compound 74
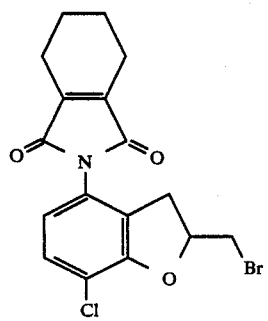
Compound 75
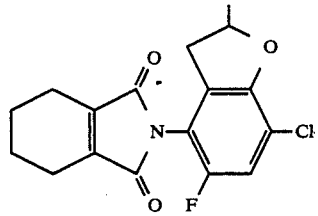
Compound 76
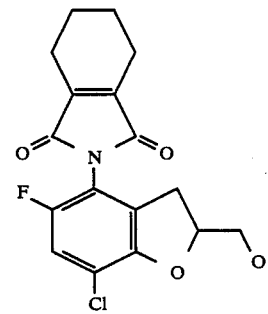
Compound 77
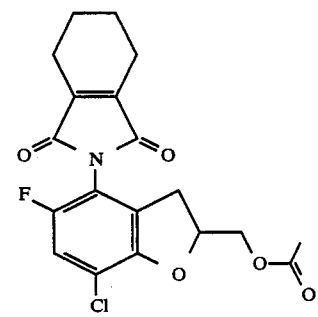
Compound 78
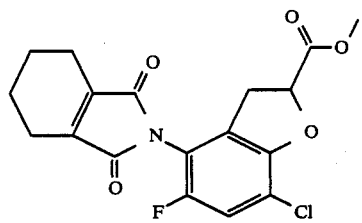
Compound 79
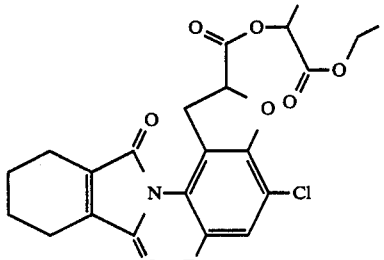
Compound 80
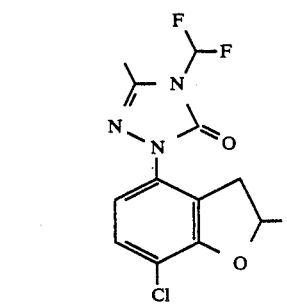
Compound 81
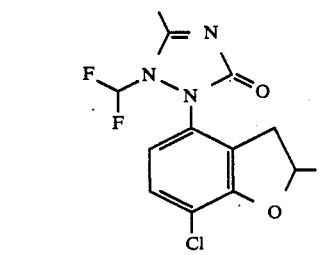
Compound 82
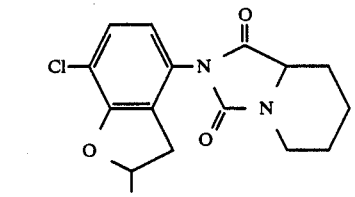
Compound 83
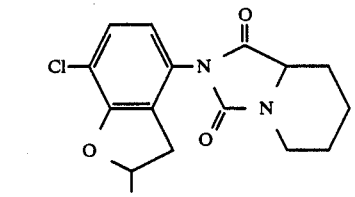
Compound 84
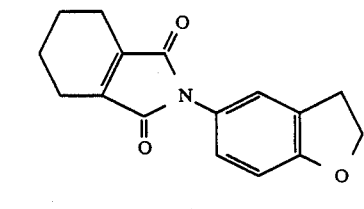
Compound 85
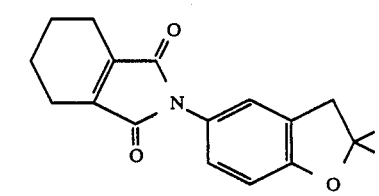

-continued
BIOLOGICAL TABLES
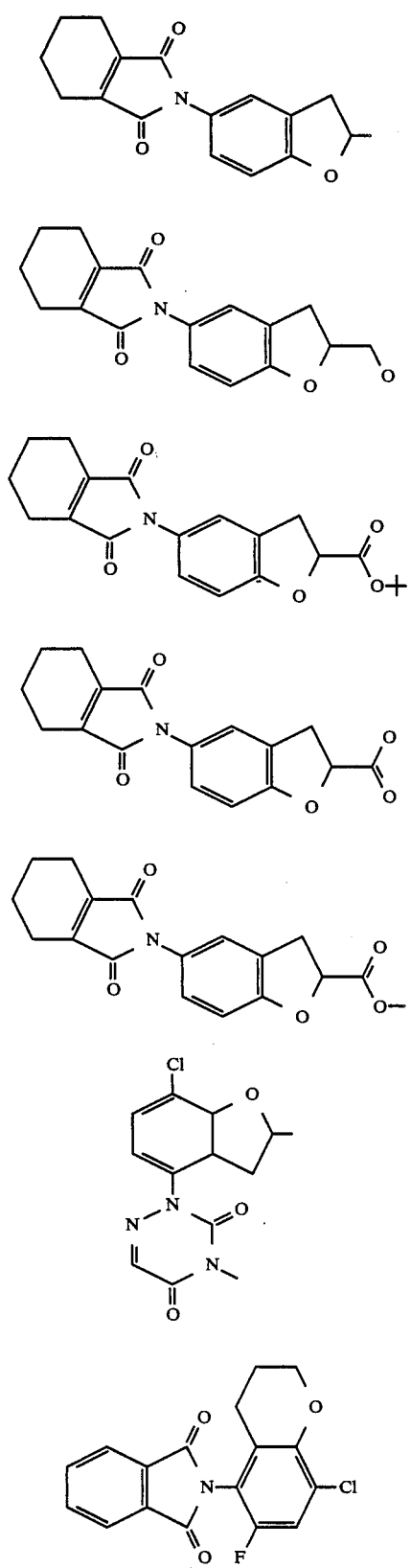
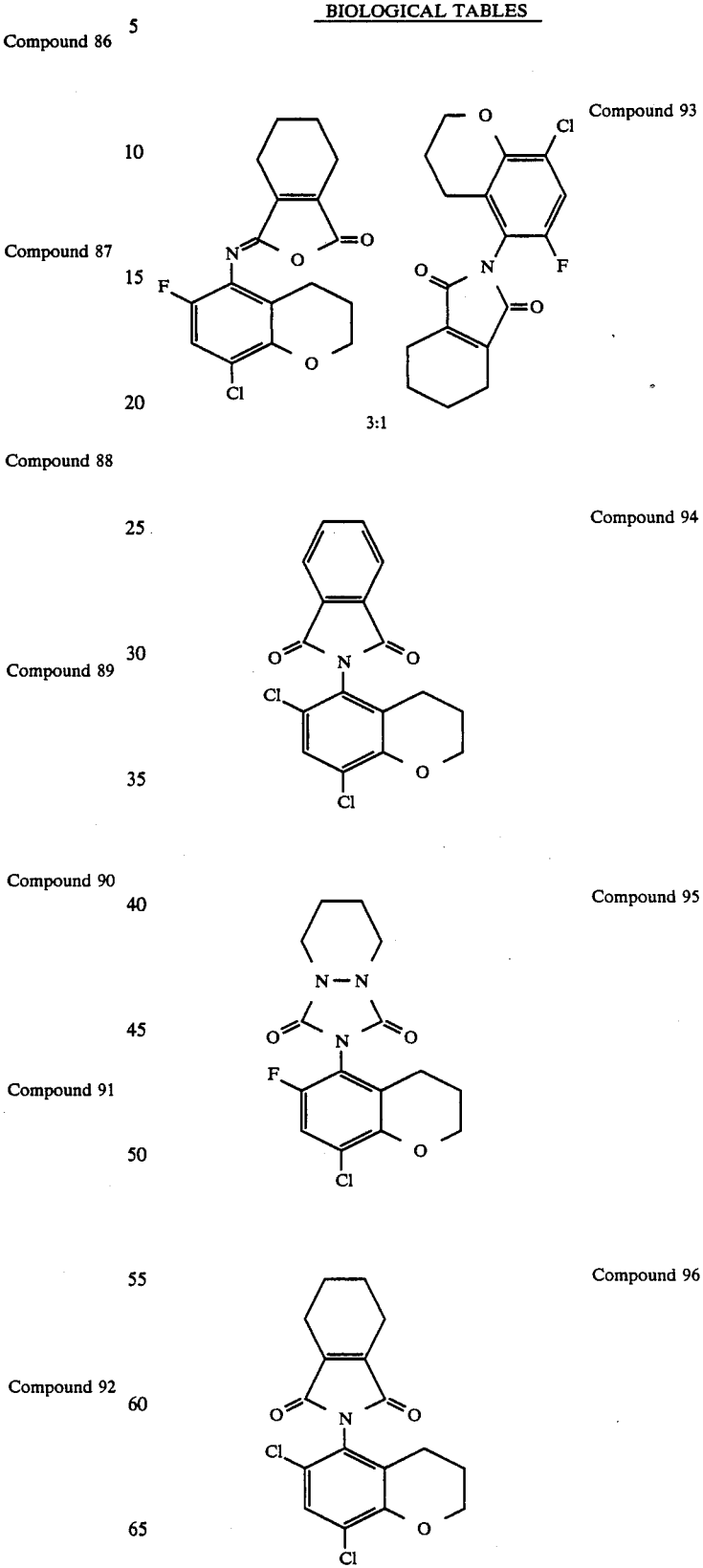

-continued
BIOLOGICAL TABLES
Compound 97
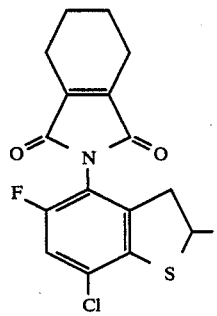
Compound 98
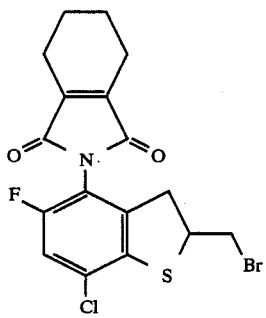
Compound 99
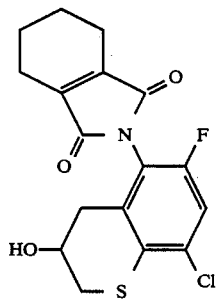
1:5
Compound 100
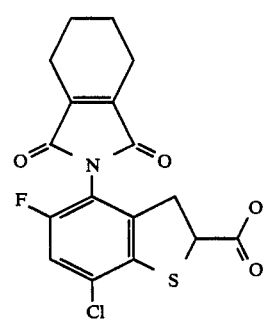
-continued
BIOLOGICAL TABLES
Compound 101
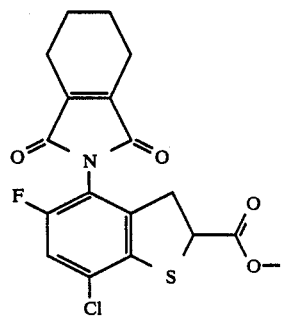
Compound 102
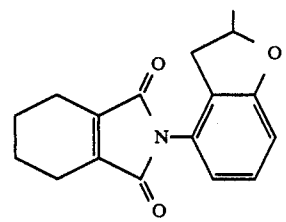
Compound 103
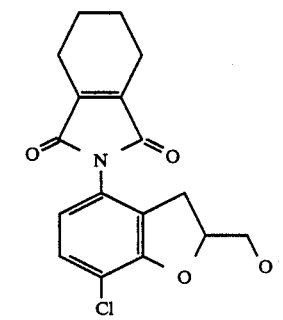
Compound 104
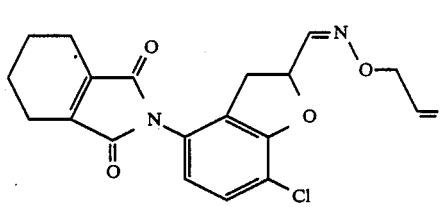
Compound 105
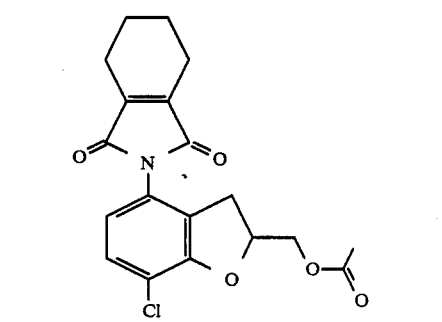
Compound 106
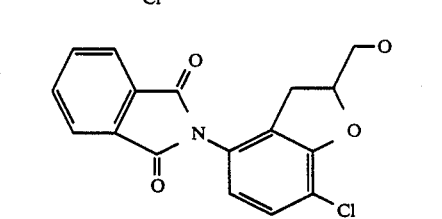

BIOLOGICAL TABLES
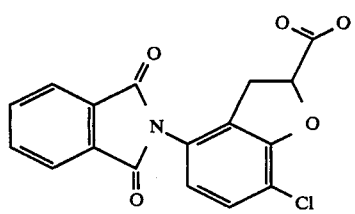
Compound 107
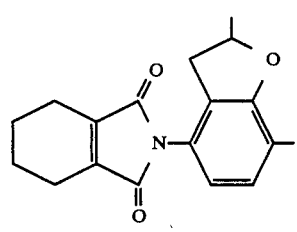
Compound 108
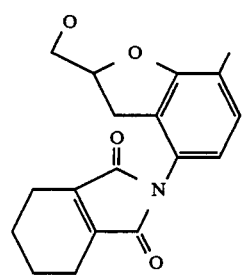
Compound 109
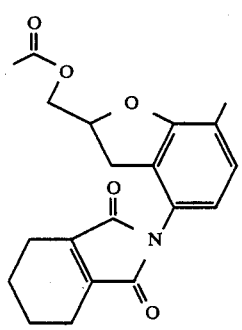
Compound 110
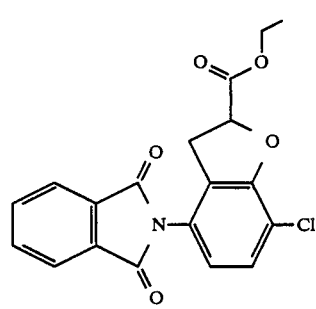
Compound 111
BIOLOGICAL TABLES
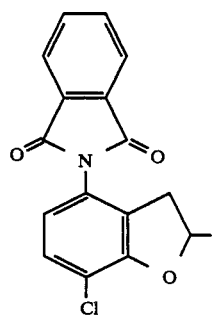
Compound 112
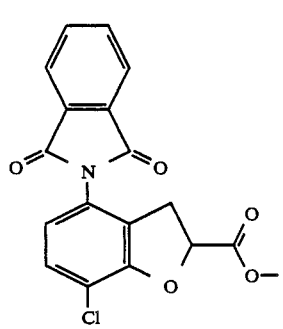
Compound 113
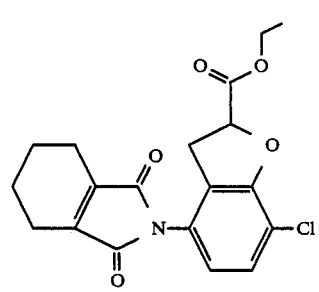
Compound 114
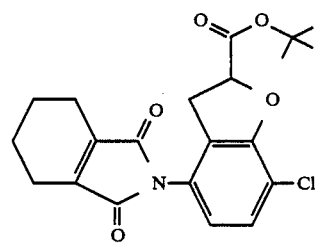
Compound 115
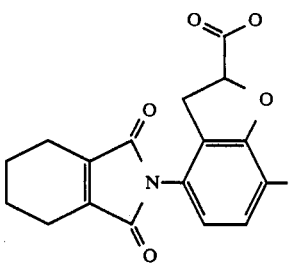
Compound 116

-continued
BIOLOGICAL TABLES

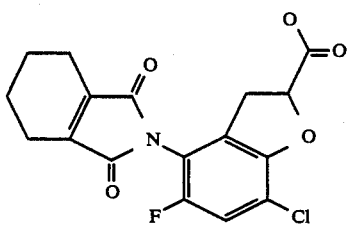

Compound 117

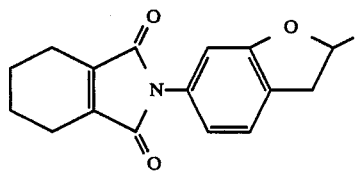

Compound 118

Test A

Seeds of crabgrass (*digitaria spp.*), barnyardgrass (*Echinochloa crus-galli*), giant foxtail (*Setaria feberii*), wild oats (*Avena fatua*), cheatgrass (*Bromus secalinus*), velvetleaf (*Abutilon theophrasti-*), morningglory (*Ipomoea spp.*), cocklebur (*Xanthium pensylvanicum*), sorghum, corn, soybean, sugarbeet, cotton, rice, wheat, barley and purple nutsedge (*Cyperus rotundus*) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
Y=abscised buds or flowers.

TABLE A

| RATE = KG/HA | CMPD 1 0.05 | CMPD 1 0.4 | CMPD 2 0.05 | CMPD 3 0.05 | CMPD 4 0.05 | CMPD 4 0.4 | CMPD 5 0.05 | CMPD 6 0.05 | CMPD 6 0.4 | CMPD 7 0.05 | CMPD 7 0.01 | CMPD 8 0.05 | CMPD 8 0.01 | CMPD 9 0.05 | CMPD 9 0.4 | CMPD 10 0.05 | CMPD 10 0.4 | CMPD 11 0.05 | CMPD 11 0.4 | CMPD 12 0.05 | CMPD 12 0.4 |
|---|---|---|---|---|---|---|---|---|---|---|---|---|---|---|---|---|---|---|---|---|---|
| POSTEMERGENCE | | | | | | | | | | | | | | | | | | | | | |
| COTTON | 0 | 7B | 8B | 2B | 10B | 9B | 9B | 9B | 10B | 10B | 10B | 10B | 10B | 9B | 10B | 10B | 10B | 10B | 10B | 10B | 10B |
| MORNINGGLORY | 2B | 6B | 5B | 1B | 10B | 10B | 7B | 3B | 10B | 10B | 9B | 10B | 9B | 7B | 10B | 9B | 8B | 8B | 9B | 9B | 10B |
| COCKLEBUR | 0 | 4B | 2B | 0 | 9B | 8B | 3B | 4B | 8B | 10B | 7B | 9B | 7B | 5B | 7B | 5B | 7B | 7B | 4B | 6B | 9B |
| NUTSEDGE | 0 | 1B | 1B | 0 | 10B | 9B | 0 | 2B | 3B | 7B | 5B | 4B | — | 2B | 5B | 3B | 8B | 4B | 3G | 6B |
| CRABGRASS | 1B | 5B | 2B | 1B | 8B | 9H | 1B | 3B | 7B | 3B | 5B | 9B | 5B | 4B | 7B | 7B | 3B | 8B | 4B | 5B | 3B,7G |
| BARNYARDGRASS | 1B | 4B | 4B | 2B | 5B | 8B | 1B | 6B | 5B | 4B | 7B | 9B | 7B | 6B | 9B | 6B | 8B | 3B | 7B | 5B | 5B |
| WILD OATS | 1B | 2B | 2B | 1B | 4B | 8B | 1B | 3B | 5B | 4B | 5B | 5B | 3B | 3B | 6B | 6B | 4B | 7B | 6B | 4B | 3B |
| WHEAT | 0 | 1B | 1B | 0 | 2B | 7B | 0 | 2B | 4B | 4B | 4B | 6B | 4B | 4B | 4B | 3B | 2B | 6B | 4B | 2B | 2B |
| CORN | 1B | 3B | 2B | 1B | 5B | 4B | 1B | 3B | 4B | 3B | 5B | 5B | 5B | 3B | 4B | 4B | 2B | 9B | 8B | 3B | 0 |
| SOYBEANS | 1B | 4B | 2C,3G | 2B | 3B,8G | 8B | 3B,6G | 4B | 8B | 5B | 5B | 7B | 8B | 4B | 7B | 5B | 7B | 9B | 5B | 7B | 1B |
| RICE | 1B | 4B | 1B | 1B | 5B | 6B | 2B | 5B | 6B | 4B | 4B | 4B | 6B | 5B | 4B | 4B | 4B | 4B | 4B | 4B | 5B |
| SORGHUM | 1B | 3B | 1B | 1B | 7B | 5B | 3B | 4B | 5B | 3B | 3B | 5B | 5B | 2B | 5B | 2B | 4B | 5B | 4B | 4B | 2B |
| CHEATGRASS | 0 | 0 | 1B | 0 | 1B | 1B | 3B,4H | 2B | 3B | 3B | 4B | 4B | 7B | 5B | 7B | 4B | 8B | 1B | 2B | 1B | 3B |
| SUGARBEETS | 1B | 6B | 1B | 2B | 9B | 5B,8H | 5B,4H | 7B | 8B | 10B | 10B | 7B | 10B | 9B | 10B | 8B | 10B | 10B | 9B | 10B | 6B |
| VELVETLEAF | 2B | 7B | 6B | 3B | 10B | 10B | 9B | — | — | 9B | 8B | 10B | 7B | 8B | 8B | 8B | 7B | 9B | 9B | — | 0 |
| GIANT FOXTAIL | 1B | 6B | 2B | 1B | 7B | 5B | 1B | 4B | 5B | 6B | 4B | 8B | 6B | 4B | 4B | 4B | 4B | 9B | 5B | 6B | 4B |
| BARLEY | 0 | 2B | 2B | 0 | 2B | 2B | 0 | 4B | 2B | 3B | 3B | 4B | 4B | 4B | 4B | 2B | 2B | 5B | 3B | 3B | 1B |

| RATE = KG/HA | CMPD 1 0.4 | CMPD 2 0.05 | CMPD 4 0.05 | CMPD 5 0.05 | CMPD 6 0.4 | CMPD 6 0.05 | CMPD 7 0.4 | CMPD 8 0.01 | CMPD 9 0.05 | CMPD 10 0.4 | CMPD 11 0.05 | CMPD 12 0.05 |
|---|---|---|---|---|---|---|---|---|---|---|---|---|
| PREEMERGENCE | | | | | | | | | | | | |
| COTTON | 0 | 0 | 0 | 2G | 4C,9G | 3C | 0 | 0 | 0 | 3G | 1H | 0 |
| MORNINGGLORY | 0 | 0 | 3C | 4C | 4C,9G | 3C,8G | 7G | 0 | 2H | 10H | 10C | 0 |
| COCKLEBUR | 0 | 0 | 10E | 2C | 4C,9G | 1C | 1H | 0 | 0 | 3H | 1H | 0 |
| NUTSEDGE | 0 | 0 | 7C | 7G | 9C | 0 | 0 | 0 | 8G | 2C | 9H | 0 |
| CRABGRASS | 0 | 0 | 7C | 3C,8H | 9H | 0 | 6G | 0 | 7C | 9H | 7C | 3G |
| BARNYARDGRASS | 0 | 0 | 0 | 2G | 9C | 3C | 3C,6G | 0 | 0 | 4C | 4C | 0 |
| WILD OATS | 0 | 0 | 0 | 2C | 8C | 3C | 0 | 0 | 2G | 1C | 1C | 0 |
| WHEAT | 0 | 0 | 0 | 2C | 10C | 6C | 2C | 0 | 0 | 4G | 4G | 0 |
| CORN | 0 | 0 | 4G | 2C | 5C,9H | 4C | 0 | 0 | 0 | 4G | 4G | 0 |
| SOYBEANS | 0 | 0 | 0 | 2C | 3C,9G | 3C,7G | 1C | 0 | 0 | 5G | 2C | 0 |
| RICE | 0 | 0 | 6G | 4C | 10C | 5C | 1C,4G | 0 | 0 | 1C | 2C | 0 |
| SORGHUM | 0 | 0 | 2G | 2C,5H | 10C | 6C | 0 | 0 | 0 | 2G | 0 | 0 |
| CHEATGRASS | 0 | 0 | 2G | 2G | 7C | 0 | 7H | 0 | 0 | 7G | 0 | 0 |
| SUGARBEETS | 0 | 0 | 2G | 5G | 10E | 10C | 8G | 0 | 7H | 10E | 10E | 3G |
| VELVETLEAF | 0 | 0 | 9C | 5C | 10E | 9C | 9H | 0 | 3G | 10H | 8G | 4G |
| GIANT FOXTAIL | — | 0 | 10C | 2C,8G | 9H | 0 | 9H | 2G | 10E | 10H | 2C,8H | 0 |
| BARLEY | 0 | 0 | 0 | 0 | 7C | 0 | 1C | 0 | 0 | 2C | 0 | 0 |

| RATE = KG/HA | CMPD 13 0.05 | CMPD 14 0.05 | CMPD 15 0.05 | CMPD 16 0.05 | CMPD 17 0.05 | CMPD 18 0.05 | CMPD 19 0.05 | CMPD 20 0.05 | CMPD 21 0.05 | CMPD 22 0.05 | CMPD 23 0.05 | CMPD 24 0.05 | CMPD 25 0.05 | CMPD 26 0.05 |
|---|---|---|---|---|---|---|---|---|---|---|---|---|---|---|
| POSTEMERGENCE | | | | | | | | | | | | | | |
| COTTON | 10B | 10B | 10B | 10B | 10B | 10B | 8B | 2B | 10B | 10B | 10B | 10B | 10B | 10B |

TABLE A-continued

| | CMPD 13 | | CMPD 4 | | CMPD 5 | | CMPD 16 | | CMPD 17 | | CMPD 18 | | CMPD 19 | | CMPD 20 | | CMPD 21 | | CMPD 22 | | CMPD 23 | | CMPD 24 | | CMPD 25 | | CMPD 26 |
|---|---|---|---|---|---|---|---|---|---|---|---|---|---|---|---|---|---|---|---|---|---|---|---|---|---|---|
| RATE = KG/HA | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.05 |
| MORNINGLORY | 9B | 5B | 10B | 6B | 3B | 3B | 10B | 6B | 10B | 9B | 5B | 3B | 6B | 1B | 10B | 2B | 10B | 7B | 10B | 5B | 10B | 5B | 10B | 4B | 10B | — | 10B | 8B |
| COCKLEBUR | 5B | 5B | 7B | 5B | 4B | 3B | 8B | 6B | 9B | 7B | 3B | 3B | 1B | 1B | 6B | 2B | 10B | 4B | 10B | 9B | 10B | — | 10B | 4B | 10B | 10B | 7B |
| NUTSEDGE | 5B | 1B | 4B | 2B | 1B | 1B | 9B | 2B | 7B | 3B | 1B | 1B | 2B | 0 | 2B | 0 | 8B | 1B | 5B | 5B | 5B | 4B | 4B | 4B | 4B | 2B |
| CRABGRASS | 4B | 1B | 7B | 3B | 1B | 1B | 5B | 4B | 10B | 5B | 1B | 1B | 2B | 1B | 6B | 1B | 9B | 3B | 8B | 9B | 9B | 5B | 7B | 7B | 8B | 4B | 5B |
| BARNYARDGRASS | 3B | 1B | 10B | 6B | 3B | 1B | 10B | 4B | 7B | 5B | 2B | 1B | 2B | 1B | 7B | 2B | 10B | 3B | 9B | 5B | 5B | 5B | 5B | 8B | 5B |
| WILD OATS | 5B | 3B | 7B | 3B | 1B | 1B | 7B | 5B | 6B | 3B | 3B | 1B | 3B | 2B | 5B | 4B | 6B | 5B | 5B | 6B | 5B | 5B | 7B | 5B | 4B |
| WHEAT | 5B | 3B | 7B | 3B | 1B | 1B | 7B | 5B | 9B | 5B | 4B | 3B | 3B | 2B | 5B | 4B | 6B | 3B | 5B | 6B | 5B | 7B | 5B | 7B | 4B |
| CORN | 4B | 3B | 8B | 7B | 2B | 1B | 6B | 2B | 6B | 6B | 2B | 2B | 3B | 2B | 8B | 4B | 8B | 3B | 5B | 5B | 5B | 7B | 5B | 8B | 8B |
| SOYBEANS | 7B | 7B | 6B | 4B | 2B | 2B | 8B | 5B | 9B | 6B | 3B | 2B | 3B | 2B | 6B | 5B | 7B | 3B | 9B | 7B | 5B | 7B | 7B | 5B | 5B |
| RICE | 6B | 4B | 6B | 3B | 1B | 1B | 5B | 2B | 6B | 6B | 4B | 3B | 3B | 2B | 5B | 5B | 7B | 3B | 6B | 6B | 5B | 5B | 9B | 5B | 6B |
| SORGHUM | 3B | 1B | 4B | 2B | 2B | 2B | 5B | 3B | 6B | 3B | 3B | 2B | 2B | 1B | 5B | 2B | 7B | 3B | 8B | 7B | 5B | 5B | 7B | 8B | 5B |
| SUGARBEETS | 8B | 5B | 10B | 6B | 3B | 3B | 8B | 7B | 9B | 5B | 5B | 3B | 5B | 2B | 7B | 3B | 8B | 6B | 9B | 1B | 9B | 9B | 10B | 9B |
| VELVETLEAF | 10B | 7B | 10B | 6B | 2B | 2B | 10B | 7B | 10B | 10B | 7B | 5B | 5B | 2B | 10B | 3B | 10B | 8B | 10B | 10B | 10B | 9B | 10B | 10B |
| GIANT FOXTAIL | 6B | 1B | 9B | 2B | 3B | 1B | 7B | 2B | 7B | 5B | 3B | 2B | 5B | 2B | 7B | 2B | 5B | 5B | 7B | 9B | 9B | 7B | 5B | 7B | 3B |
| BARLEY | 4B | 3B | 5B | 3B | 1B | 1B | 6B | 2B | 5B | 3B | 2B | 2B | 3B | 2B | 5B | 3B | 6B | 2B | 5B | 4B | 6B | 5B | 4B | 6B |
| DOWNY BROME | 7B | 2B | 7B | 2B | 2B | 2B | 4B | 3B | 3B | 3B | 4B | 1B | 3B | 1B | 3B | 2B | 10B | 5B | 4B | 5B | 5B | 7B | 4B | 3B | 2B |

| | CMPD 13 | CMPD 4 | CMPD 5 | CMPD 16 | CMPD 17 | CMPD 18 | CMPD 19 | CMPD 20 | CMPD 21 | CMPD 22 | CMPD 23 | CMPD 24 | CMPD 25 | CMPD 26 |
|---|---|---|---|---|---|---|---|---|---|---|---|---|---|---|
| RATE = KG/HA | 0.05 | 0.4 | 0.4 | 0.4 | 0.4 | 0.4 | 0.4 | 0.4 | 0.4 | 0.4 | 0.4 | 0.4 | 0.4 | 0.05 |
| PREEMERGENCE | | | | | | | | | | | | | | |
| COTTON | 0 | 0 | 0 | 1C | 2C,7G | 0 | 0 | 2G | 3C,7G | 0 | 5G | 0 | 0 | 0 |
| MORNINGGLORY | 0 | 0 | 0 | 3G | 2C,8G | 0 | 0 | 0 | 9C | 6G | 0 | 0 | 0 | 0 |
| COCKLEBUR | 0 | 8G | 0 | 10G | 3C,8G | 0 | 0 | 0 | 2C | 0 | 0 | 0 | 0 | 0 |
| NUTSEDGE | 0 | 0 | 0 | 2C | 7C | 0 | 0 | 0 | 8C | 2G | 0 | 0 | 0 | 0 |
| CRABGRASS | 6C | 10H | 0 | 6G | 10E | 1H | 0 | 2C | 10H | 8G | 0 | 0 | 0 | 0 |
| BARNYARDGRASS | 5G | 10H | 0 | 8H | 10H | 4H | 0 | 0 | 9H | 6G | 0 | 0 | 0 | 0 |
| WILD OATS | 8C | 7C | 0 | 4C | 7C | 0 | 0 | 0 | 7C | 0 | 0 | 0 | 0 | 0 |
| CORN | 2G | 3H | 0 | 2G | 8C | 3G | 0 | 0 | 3C,7H | 2G | 0 | 0 | 0 | 0 |
| SOYBEANS | 5C | 2G | 0 | 1C | 3C,8H | 0 | 0 | 0 | 7C | 0 | 0 | 0 | 0 | 0 |
| RICE | 2C | 0 | 0 | 1C | 9H | 0 | 0 | 0 | 2C,8G | 0 | 0 | 0 | 0 | 0 |
| SORGHUM | 6C | 7G | 0 | 2G | 2H | 0 | 0 | 0 | 8C | 2G | 0 | 0 | 0 | 0 |
| SUGARBEETS | 5C,9G | 6C | 0 | 5G | 3C,6G | 1H | 0 | 1C | 3C | 2C,5G | 5G | 0 | 6C | 0 |
| VELVETLEAF | 10C | 10C | 0 | 9C | 10C | 2G | 0 | 1H | 9C | 3G | 3G | 0 | 0 | 0 |
| GIANT FOXTAIL | 0 | 10C | 0 | 10C | 10C | 8G | 4G | 2C | 10C | 2C,5G | 8G | 4G | 0 | 8G |
| BARLEY | 7H | 10H | 8H | 9H | 10H | 7H | 0 | 2G | 10H | 2G | 0 | 0 | 0 | 0 |
| DOWNY BROME | 0 | 0 | 0 | 0 | 0 | 0 | 0 | 0 | 1C | 0 | 0 | 0 | 0 | 0 |
| | 6G | 9C | 2G | 7G | 5G | 3G | 2G | 2G | 2C,5G | 2G | 0 | 0 | 0 | 0 |

| | CMPD 27 | CMPD 28 | CMPD 29 | CMPD 30 | CMPD 31 | CMPD 32 | CMPD 33 | CMPD 34 | CMPD 35 | CMPD 36 | CMPD 37 |
|---|---|---|---|---|---|---|---|---|---|---|---|
| RATE = KG/HA | 0.1 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.01 |
| POSTEMERGENCE | | | | | | | | | | | | |
| COTTON | 10B | 10B | 10B | 10B | 10B | 10B | 10B | 10B | 10B | 10B | 10B | 10B | 10B | 10B | 10B | 10B | 10B | 10B |
| MORNINGGLORY | 10B | 10B | 10B | 10B | 10B | 10B | 10B | 10B | 10B | 10B | 10B | 10B | 10b | 10B | 9B |
| COCKLEBUR | 10B | 10B | 8B | 7B | 10B | 10B | 10B | 9B | 9B | 9B | 10B | 10B | 9B | 9B | 9B |
| NUTSEDGE | — | 7B | 6G | 10B | 9G | 5B | — | 0 | 3B | 2B | 3B | 5B | 3B | 4B | 4B |
| CRABGRASS | 2B | 10B | 7B | 10B | 8B | 5B | 5B | 4B | 7B | 3B | 7B | 3B | 7B | 3B | 7B |
| BARNYARDGRASS | 8B | 10B | 10B | 9B | 9B | 9B | 7B | 7B | 9B | 7B | 9B | 4B | 9B | 9B |
| WILD OATS | 10B | 10B | 9B | 10B | 8B | 7B | 7B | 7B | 7B | 4B | 7B | 3B | 10B | 3B |
| WHEAT | 9B | 10B | 5B | 4B | 4B | 5B | 5B | 6B | 4B | 6B | 4B | 4B | 4B | 4B | 5B |
| CORN | 6B | 10B | 10B | 8B | 4B | 3B | 4B | 3B | 3B | 4B | 3B | 3B | 4B | 5B | 3B |
| SOYBEANS | 7B | 10B | 4B,7H | 10B | 10B | 10B | 9B | 9B | 10B | 6B | 8B | 6B | 10B | 6B |
|  | 5B | 9B | | | | | | | | | | | | | |
|  | 9B | 10B | | | | | | | | | | | | | |

TABLE A-continued

| | CMPD 27 | | CMPD 28 | | CMPD 29 | | CMPD 30 | | CMPD 31 | | CMPD 32 | | CMPD 33 | | CMPD 34 | | CMPD 35 | | CMPD 36 | | CMPD 37 | |
|---|---|---|---|---|---|---|---|---|---|---|---|---|---|---|---|---|---|---|---|---|---|---|
| RATE = KG/HA | 0.1 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.01 |
| RICE | 7B | 5B | 9B | 8B | 10B | 9B | 9B | 5B | 7B | 5B | 7B | 4B | 7B | 4B | 7B | 4B | 7B | 5B | 5B | 4B | 4B | 4B |
| SORGHUM | 6B | 5B | 8B | 8B | 10B | 9B | 9B | 7B | 9B | 7B | 9B | 7B | 8B | 4B | 7B | 3B | 6B | 5B | 5B | 3B | 5B | 3B |
| CHEATGRASS | 6B | 6B | 7B | 7B | 4B,8H | 2B | 8B | 4B | 6B | 4B | 6B | 5B | 5B | 3B | 5B | 3B | 6B | 4B | 8B | 3B | 5B | 9B |
| SUGARBEETS | 10B | 10B | 10B | 10B | 10B | 9B | 10B | 8B | 10B | 10B | 10B | 10B | 9B | 9B | 10B | 10B | 10B | 10B | 10B | 10B | 10B | 10B |
| VELVETLEAF | 10B | 10B | 10B | 10B | 10B | 10B | 10B | 10B | 10B | 10B | 10B | 10B | 10B | 10B | 10B | 5B | 10B | 7B | 10B | 6B | 10B | 3B |
| GIANT FOXTAIL | 9B | 9B | 9B | 8B | 9B | 9B | 9B | 6B | 10B | 6B | 9B | 6B | 9B | 4B | 6B | 2B | 9B | 4B | 9B | 3B | 9B | 3B |
| BARLEY | 6B | 5B | 5B | 5B | 9B | 2B | 6B | 1B | 6B | 5B | 7B | 3B | 6B | 4B | 7B | 2B | 7B | 4B | 5B | 3B | 3B | 2B |
| PREEMERGENCE | | | | | | | | | | | | | | | | | | | | | | |
| COTTON | 4G | 0 | 9H | 0 | 8H | 8H | 0 | 7G | 2G | 0 | 6H | 0 | 2G | 0 | 5G | 2G | 0 | 0 | 5G | 3H | 0 | 0 |
| MORNINGGLORY | 9H | 2H | 10H | 6H | 9H | 10H | 9H | — | 7H | 9H | 9H | 3H | 10H | 2G | 10E | 7H | 7H | 10H | 2H | 0 | 0 |
| COCKLEBUR | 6H | 1H | 9H | 2H | 7H | 4H | 2H | 10H | 0 | 0 | 8H | 0 | 9H | 0 | 9H | 1C | 9H | 1H | 5H | 1H | 0 | 0 |
| NUTSEDGE | 0 | 0 | 4C | 0 | 3H | 3H | 4H | 2C,5G | 0 | 8G | 0 | 7G | 0 | 2G | — | 9H | 0 | 0 | 7G |
| CRABGRASS | 9H | 7G | 10H | 8H | 9H | 10H | 10H | 9H | 10H | 8G | 9H | 10H | 7G | 10H | 8H | 10H | 9H | 10H | 7H | 0 |
| BARNYARDGRASS | 9H | 2H | 10H | 3H | 9H | 9H | 9H | 9H | 7H | 4H | 9H | 3C,3H | 9H | 3C,5H | 9H | 8H | 9H | 2H | 1H | 0 |
| WILD OATS | 5G | 0 | 8H | 0 | 4H | 8H | 0 | 7H | 0 | 2H | 7H | 0 | 3C,6H | 3C,6H | 7H | 3C,6H | 3G | 0 | 0 |
| WHEAT | 2G | 0 | 9H | 0 | 7H | 9H | 0 | 7H | 0 | 2C,3G | 3C,7H | 3C,7H | 3C,7H | 4C,9H | 1H | 3G | 0 | 0 |
| CORN | 0 | 1H | 10H | 4H | 8H | 8H | 5H | 3C,6H | 2C,3H | 4C,8H | 2C,3G | 3C,7H | 1C,3G | 1C,3G | 2G | 0 | 0 |
| SOYBEANS | 2G | 0 | 10H | 6G | 9H | 9H | 3H | 3C,8H | 3C,8H | 3C,8H | 2C,3H | 4C,9H | 1H | 3C,7G | 0 | 7H | 0 |
| RICE | 0 | 0 | 10H | 4H | 9H | 8H | 2H | 3G | 8H | 8H | 8H | 3G | 5G | 3C,7G | 2G | 0 | 3H |
| SORGHUM | 6G | 0 | 7H | 5H | 10H | 6H | 3H | 3C,6G | 3C,8H | 3C,6H | 4G | 3G | 9H | 0 | 4G | 0 |
| CHEATGRASS | 2G | 0 | 10H | 9H | 10H | 10H | 7H | 0 | 3C,7G | 2C,7G | 4H | 0 | 0 | 9H | 5G | 0 |
| SUGARBEETS | 3C,8H | 2H | 10H | 10H | 10H | 10H | 9G | 8H | 3G | 2H | 1H | 10H | 7G | 8H | 8H |
| VELVETLEAF | 10H | 7H | 10H | 10H | 10H | 10H | 1H | 0 | 10H | 6H | 3H | 10H | 2G | 9H | — |
| GIANT FOXTAIL | 10H | 8H | 10H | 10H | 9H | 10H | 6H | 5H | 9H | 4G | 5H | 10H | 4H | 10H | 0 |
| BARLEY | 0 | 0 | 8H | 0 | 9H | 10H | 2H | 3C,7H | 7C | 1C | 1C | 0 | 3H |

| | CMPD 38 | | CMPD 39 | | CMPD 40 | | CMPD 41 | | CMPD 42 | | CMPD 43 | | CMPD 44 | | CMPD 45 | | CMPD 46 | | CMPD 47 | | CMPD 48 | | CMPD 49 |
|---|---|---|---|---|---|---|---|---|---|---|---|---|---|---|---|---|---|---|---|---|---|---|---|---|
| RATE = KG/HA | 0.4 | 0.01 | 0.4 | 0.05 | 0.4 | 0.05 | 0.4 | 0.05 | 0.4 | 0.05 | 0.4 | 0.05 | 0.1 | 0.05 | 0.05 | 0.01 | 0.05 | 0.01 | 0.05 | 0.01 | 0.05 | 0.01 | 0.1 |
| POSTEMERGENCE | | | | | | | | | | | | | | | | | | | | | | | | |
| COTTON | 10B | 10B | 10B | 10B | 10B | 10B | 10B | 10B | 10B | — | 10B | 10B | 9B | 9B | 10B | 10B | 10B | 10B | 10B | 10B | 10B | 10B | 10B |
| MORNINGGLORY | 10B | 9B | 10B | 10B | 10B | 10B | 10B | 10B | 10B | 10B | 9B | 9B | 5B | 5B | 10B | 9B | 10B | 10B | 10B | 10B | 9B | 10B | 9B |
| COCKLEBUR | 8B | 7B | 8B | 8B | 10B | 10B | 9B | 9B | 9B | — | 9B | 9B | 3B | 1B | 8B | 7B | 8B | 8B | 10B | 7B | 7B | 8B | 7B |
| NUTSEDGE | 10B | 4B | — | 0 | 3B | 6B | 5B | 3B | — | 9B | 3B | 3B | 1B | 1B | 3B | — | 3B | — | 3B | 1B | 1B | 8B | 1B |
| CRABGRASS | 9B | 7B | 10B | 8B | 7B | 10B | 6B | 10B | 8B | 9B | 7B | 5B | 4B | 1B | 4B | 2B | 6B | 2B | 6B | 3B | 6B | 3B | 3B |
| BARNYARDGRASS | 10B | 8B | 10B | 8B | 3B | 9B | 9B | 8B | 8B | 7B | 5B | 4B | 2B | 2B | 9B | 4B | 10B | 4B | 10B | 4B | 10B | 3B | 3B |
| WILD OATS | 9B | 7B | 8B | 8B | 7B | 3B | 7B | 5B | 4B | 4B | 4B | 3B | 2B | 1B | 5B | 2B | 4B | 3B | 4B | 1B | 3B | 2B | 2B |
| WHEAT | 10B | 6B | 8B | 4B | 3B | 5B | 6B | 5B | 5B | 5B | 4B | 4B | 3B | 2B | 4B | 3B | 3B | 4B | 4B | 2B | 3B | 3B | 3B |
| CORN | 8B | 7B | 8B | 6B | 2B | 3B | 4B | 4B | 6B | 5B | 3B | 3B | 4B | 2B | 3B | 2B | 3B | 3B | 3B | 3B | 3B | 3B | 2B |
| SOYBEANS | 9B | 8B | 9B | 6B | 3B | 5B | 10B | 5B | 7B | 5B | 3B | 3B | 2B | 2B | 5B | 3B | 5B | 4B | 5B | 4B | 5B | 4B | 4B |
| RICE | 10B | 7B | 10B | 4B | 3B | 10B | 6B | 4B | 6B | 4B | 3B | 3B | 1B | 1B | 3B | 1B | 2B | 3B | 3B | 4B | 4B | 4B | 2B |
| SORGHUM | 10B | 8B | 8B | 6B | 8B | 5B | 5B | 10B | 7B | 10B | 3B | 3B | 2B | 1B | 6B | 5B | 6B | 3B | 6B | 3B | 6B | 3B | 5B |
| CHEATGRASS | 10B | 7B | 8B | 6B | 5B | 3B | 10B | 8B | 5B | 6B | 3B | 3B | 1B | 1B | 5B | 1B | 3B | 6B | 3B | 4B | 10B | 4B | 2B |
| SUGARBEETS | 10B | 4B | 4B | 2B | 3B | 8B | 5B | 5B | 9B | 5B | 10B | 6B | 4B | 2B | 10B | 6B | 10B | 6B | 10B | 5B | 8B | 3B | 4B |
| VELVETLEAF | 10B | 10B | 10B | 10B | 9B | 7B | 10B | 9B | 9B | 7B | 7B | 5B | 5B | 3B | 9B | 8B | 9B | 7B | 9B | 7B | 8B | 0 | 7B |
| GIANT FOXTAIL | 10B | 9B | 7B | 7B | 7B | 9B | 7B | 6B | 9B | 6B | 5B | 5B | 3B | 2B | 5B | 5B | 6B | 4B | 6B | 3B | 4B | 8B | 8B |
| BARLEY | 10B | 6B | 6B | 6B | 6B | 3B | 4B | 5B | 6B | 5B | 5B | 2B | 2B | 1B | 2B | 1B | 1B | 3B | 1B | 1B | 1B | 8B | 2B |

| | CMPD 38 | CMPD 39 | CMPD 40 | CMPD 41 | CMPD 42 | CMPD 43 | CMPD 44 | CMPD 45 | CMPD 46 | CMPD 47 | CMPD 48 | CMPD 49 |

TABLE A-continued

| RATE = KG/HA | CMPD 50 | | | CMPD 51 | | | CMPD 52 | | | CMPD 53 | | | CMPD 54 | | | CMPD 55 | | | CMPD 56 | | | CMPD 57 | | | CMPD 58 | | | CMPD 59 | | | CMPD 60 | | | CMPD 61 | |
|---|---|---|---|---|---|---|---|---|---|---|---|---|---|---|---|---|---|---|---|---|---|---|---|---|---|---|---|---|---|---|---|---|---|---|---|
| PREEMERGENCE | 0.4 | 0.05 | 0.01 | 0.4 | 0.05 | 0.01 | 0.4 | 0.05 | 0.01 | 0.4 | 0.05 | 0.01 | 0.4 | 0.05 | 0.01 | 0.4 | 0.05 | 0.01 | 0.4 | 0.05 | 0.01 | 0.05 | 0.01 | 0.1 | 0.05 | 0.01 | 0.05 | 0.01 | 0.05 | 0.01 | 0.05 | 0.01 | 0.05 | 0.01 | 0.1 |
| COTTON | 10H | 6H | 2G | 8H | 0 | 0 | 0 | 0 | 3H | 0 | 0 | 6H | 0 | 0 | 9H | 1H | 0 | 0 | 0 | 0 | 0 | 0 | 0 | 0 | 3G | 0 | 0 | 0 | 0 | 0 | 0 |
| MORNINGGLORY | 10H | 9H | 2C,8H | 9H | 7H | 2G | 3H | 0 | 10C | 5H | 3H | 10H | 9H | 10H | 4H | 0 | 2H | 9C | 0 | 0 | 8G | 2G | 0 | 9H | 4H | 0 | 2H | 3H |
| COCKLEBUR | 10H | 3C,6G | 2C | 10H | 0 | 6B | 10H | 9H | 9H | 5H | 7G | 7H | 2H | 0 | 6H | 0 | 0 | 0 | 3G | 0 | 0 | 0 | 0 | 4H | 3H | 3H |
| NUTSEDGE | 10C | — | — | 0 | 10E | 0 | 2C,5G | 5G | 10H | 3G | 10H | 0 | 10E | 0 | 0 | 0 | 0 | 10E | 0 | 0 | 0 | 0 | 0 | 0 | 10E | 0 |
| CRABGRASS | 10E | 10H | 9H | 10E | 0 | 0 | 8H | 10H | 8G | 5G | 8H | 3G | 0 | 0 | 6G | 0 | 0 | 0 | 0 | 0 | 0 | 2G | 0 | 0 | 0 | 0 |
| BARNYARDGRASS | 10H | 10H | 5C,8H | 10H | 9H | 3B | 9H | 8H | 3H | 10H | 10H | 10H | 7H | 8G | 10E | 0 | 0 | 0 | 0 | 0 | 0 | 3G | 0 | 0 | 0 | 0 |
| WILD OATS | 10H | 3C,6H | 2C | 10H | 5C,8H | 3B | 2H | 0 | 10H | 8H | 3H | 10H | 6H | 7H | 6G | 0 | 0 | 0 | 0 | 0 | 0 | 0 | 0 | 0 | 0 | 0 |
| WHEAT | 9H | 2C,7H | 3C,6G | 5C,9H | 3C | 3H | 2C,5G | 2G | 3C,6H | 2C,4G | 9H | 3C,6G | 0 | 0 | 0 | 0 | 0 | 0 | 0 | 0 | 0 | 0 |
| CORN | 10H | 4C,9H | 3C,8H | 4C,9H | 3C,6G | 4H | 3C,6H | 3G | 3C,5H | 3C,6G | 0 | 0 | 0 | 0 | 0 | 0 | 0 | 0 | 0 | 0 | 0 |
| SOYBEANS | 10E | 2C,9G | 8G | 8G | 2G | 5G | 2H | 0 | 2C,5H | 0 | 4C,9H | 3C,6H | 0 | 0 | 0 | 0 | 0 | 0 | 0 | 0 | 0 | 0 |
| RICE | 10H | 3C,7G | 2C,7G | 4C,8G | 5G | 7G | 2C,7G | 2G | 3G | 9G | 3C,5G | 0 | 0 | 0 | 0 | 0 | 0 | 0 | 0 | 0 | 0 |
| SORGHUM | 10H | 9H | 8H | 9H | 7G | 0 | 3C,7G | 0 | 3C,8H | 0 | 5C,8G | 9C | 0 | 0 | 0 | 0 | 0 | 0 | 0 | 0 | 0 | 0 |
| CHEATGRASS | 9H | 5G | 0 | 0 | 0 | 0 | 4G | 2G | 4G | 2G | 3C,6H | 9H | 0 | 0 | 0 | 0 | 0 | 0 | 0 | 0 | 0 | 0 |
| SUGARBEETS | 10H | 10H | 7H | 8H | 5H | 0 | 5H | 3H | 10H | 9H | 4G | 2G | 10C | 2G | 3H | 0 | 0 | 7G | 5G | 4H | 0 | 5H | 2H |
| VELVETLEAF | 10H | 10H | 10H | 9H | 9H | 7H | 9H | 9H | 10H | 9H | 9H | 3H | 3C,7H | 0 | 0 | 7G | 0 | 0 | 8G | 4G | 5H | 0 |
| GIANT FOXTAIL | 10H | 10H | 9H | 10H | 9H | 3B | 8H | 8H | 7H | 10H | 10H | 10H | 7H | 9H | 10C | 3G | 3G | 5G | 0 | 0 | 0 | 2H | 2G | 2C,6G |
| BARLEY | 10H | 5C,9H | 6C | 9C | 2C | 2C | 2C | 3C,7H0 | 6C | 8C | 0 | 0 | 0 | 0 | 0 | 0 | 0 | 0 | 0 | 2C,6G |

| RATE = KG/HA | CMPD 50 | | CMPD 51 | | CMPD 52 | | CMPD 53 | | CMPD 54 | | CMPD 55 | | CMPD 56 | | CMPD 57 | | CMPD 58 | | CMPD 59 | | CMPD 60 | | CMPD 61 | |
|---|---|---|---|---|---|---|---|---|---|---|---|---|---|---|---|---|---|---|---|---|---|---|---|---|
| POSTEMERGENCE | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.1 | 0.05 | 0.01 | 0.05 | 0.01 | 0.05 | 0.01 | 0.01 |
| COTTON | 10B | 10B | 10B | 10B | 10B | 10B | 10B | 10B | 10B | 10B | 10B | 10B | 10B | 10B | 10B | 10B | 10B | 10B | 10B | 10B | 10B | 10B | 10B | 10B |
| MORNINGGLORY | 10B | 10B | 10B | 10B | 10B | 10B | 10B | 10B | 10B | 10B | 9B | 7B | 10B | 7B | 10B | 10B | 10B | 10B | 10B | 10B | 10B | 10B | 9B | 9B |
| COCKLEBUR | 10B | 8B | 10B | 6B | 8B | 8B | 8B | 7B | 7B | 7B | 7B | 7B | 10B | 7B | 7B | 7B | 10B | 10B | 8B | 10B | 8B | 8B | 6B | 6B |
| NUTSEDGE | — | — | — | — | — | — | — | — | 1B | — | 1B | — | 2B | 1B | 2B | 3B | 2B | 0 | 0 | 3B | 3B | 3B | 1B | 4B |
| CRABGRASS | 4B | 2B | 5B | 2B | 6B | 2B | 4B | 3B | 4B | 4B | 5B | 4B | 1B | 1B | 2B | 3B | 6B | 4B | 2B | 5B | 3B | 5B | 4B | 1B |
| BARNYARDGRASS | 9B | 8B | 9B | 3B | 9B | 4B | 10B | 3B | 6B | 6B | 10B | 5B | 5B | 5B | 8B | 8B | 9B | 8B | 4B | 8B | 8B | 4B | 2B | 2B |
| WILD OATS | 2B | 1B | 3B | 1B | 3B | 2B | 4B | 1B | 2B | 2B | 4B | 3B | 3B | 3B | 2B | 2B | 5B | 4B | 2B | 4B | 3B | 3B | 3B | 2B |
| WHEAT | 2B | 1B | 2B | 1B | 2B | 1B | 1B | 1B | 2B | 1B | 2B | 1B | 2B | 1B | 1B | 1B | 5B | 3B | 1B | 3B | 2B | 2B | 2B | 2B |
| CORN | 4B | 1B | 2B | 1B | 3B | 3B | 3B | 2B | 4B | 4B | 5B | 5B | 3B | 3B | 2B | 3B | 7B | 5B | 2B | 5B | 2B | 2B | 1B | 1B |
| SOYBEANS | 6B | 3B | 3B | 1B | 2B | 2B | 3B | 2B | 2B | 2B | 2B | 2B | 3B | 2B | 2B | 2B | 4B | 2B | 2B | 2B | 2B,3H | 2B | 2B | 2B,2H |
| RICE | 3B | 2B | 4B | 2B | 2B | 2B | 4B | 2B | 4B | 4B | 8B | 6B | 3B | 3B | 1B | 1B | 2B | 1B | 1B | 5B | 5B | 4B | 4B | 2B |
| SORGHUM | 2B | 2B | 3B | 1B | 3B | 1B | 2B | 1B | 2B | 2B | 6B | 4B | 1B | 1B | 1B | 1B | 4B | 2B | 1B | 2B | 2B | 2B | 2B | 2B |
| CHEATGRASS | 2B | 2B | 5B | 1B | 5B | 1B | 4B | 2B | 4B | 1B | 4B | 1B | 3B | 2B | 2B | 2B | 2B | 1B | 2B | 3B | 3B | 3B | 2B | 0 |
| SUGARBEETS | 6B | 2B | 6B | 6B | 9B | 5B | 9B | 5B | 4B | 2B | 9B | 2B | 7B | 7B | 8B | 8B | 8B | 7B | 2B | 10B | 10B | 10B | 3B | 4B |
| VELVETLEAF | 10B | 6B | 10B | 6B | 10B | 7B | 10B | 6B | 10B | 7B | 10B | 9B | 7B | 4B | 5B | 10B | 10B | 10B | 6B | 10B | 8B | 6B | 10B | 3B |
| GIANT FOXTAIL | 9B | 5B | 6B | 4B | 5B | 2B | 7B | 4B | 9B | 8B | 10B | 4B | 4B | 4B | 5B | 5B | 8B | 7B | 4B | 7B | 4B | 5B | 9B | 3B |
| BARLEY | 2B | 1B | 1B | 1B | 1B | 1B | 1B | 1B | 2B | 1B | 1B | 1B | 2B | 1B | 1B | 1B | 2B | 2B | 1B | 1B | 1B | 1B | 1B | 1B |

| RATE = KG/HA | CMPD 50 | | CMPD 51 | | CMPD 52 | | CMPD 53 | | CMPD 54 | | CMPD 55 | | CMPD 56 | | CMPD 57 | | CMPD 58 | | CMPD 59 | | CMPD 60 | | CMPD 61 | |
|---|---|---|---|---|---|---|---|---|---|---|---|---|---|---|---|---|---|---|---|---|---|---|---|---|
| PREEMERGENCE | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COTTON | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| MORNINGGLORY | 10H | 8H | 7H | 2H | 7H | 2G | 7H | 3H | 3H | — | 2G | 0 | 4H | 2H | 3H | 2H | 7H | 2H | 8H | 0 | 8H | 0 | 0 | 5H |
| COCKLEBUR | 3H | 0 | 0 | 0 | 0 | 0 | 0 | 0 | — | 0 | 2G | 3H | 2H | 0 | 2H | 0 | 0 | 0 | 10E | 0 | 7H | 3G | 0 | 0 |
| NUTSEDGE | 0 | 0 | 0 | 0 | 0 | 0 | 0 | 0 | 0 | 0 | 3C,8H | 0 | 10E | 0 | 0 | — | 0 | 0 | 3H | 0 | 2G | 0 | 0 | 0 |
| CRABGRASS | 0 | 0 | 0 | 0 | 0 | 0 | 0 | 0 | 0 | 0 | 3C,7H | 3H | 0 | 0 | 0 | 0 | 0 | 0 | 0 | 0 | 0 | 0 | 0 | 0 |
| BARNYARDGRASS | 2G | 0 | 0 | 0 | 0 | 0 | 0 | 0 | 0 | 0 | 0 | 2H | 0 | 0 | 0 | 0 | 0 | 0 | 0 | 0 | 0 | 0 | 0 | 0 |
| WILD OATS | 2G | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| WHEAT | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE A-continued

| | CMPD 62 | | CMPD 63 | | CMPD 64 | | CMPD 65 | | CMPD 66 | | CMPD 67 | | CMPD 68 | | CMPD 69 | | CMPD 70 | | CMPD 71 | | CMPD 72 | | CMPD 73 | |
|---|---|---|---|---|---|---|---|---|---|---|---|---|---|---|---|---|---|---|---|---|---|---|---|---|
| RATE = KG/HA | 0.05 | 0.01 | 0.05 | 0.01 | 0.4 | 0.05 | 0.05 | 0.01 | 0.05 | 0.01 | 0.05 | 0.01 | 0.05 | 0.01 | 0.05 | 0.01 | 0.4 | 0.05 | 0.4 | 0.05 | 0.4 | 0.05 | 0.4 | 0.05 |
| CORN | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| SOYBEANS | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| RICE | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| SORGHUM | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| CHEATGRASS | 0 | 0 | 3H | 0 | 3H | 0 | 0 | 0 | 0 | 0 | 0 | 0 | 0 | 0 | 7H | 3H | 8H | 0 | 2H | 0 | 0 | 0 | 0 | 0 |
| SUGARBEETS | 8H | 3H | 0 | 0 | 0 | 0 | 8H | 0 | 3C,8H | 0 | 8H | 0 | 3H | 0 | 3H | 0 | 4C,9H | 0 | 2H | 0 | 3C,7H | 0 | 3C,7H | 0 |
| VELVETLEAF | 0 | 0 | 3H | 0 | 0 | 8H | 10H | 0 | 4C,9H | 0 | 4H | 0 | 7H | 0 | 0 | 6H | 3H | 2H | 2H | 0 | 3C,8H | 0 | 3C,8G | 2G |
| GIANT FOXTAIL | 4G | 0 | 7H | 0 | 2H | 0 | 2H | 0 | 4C,9H | 0 | 4H | 0 | 0 | 0 | 0 | 0 | 2H | 0 | 2H | 0 | 8G | 2G | 4C,8G | 7H |
| BARLEY | 0 | 0 | 4H | 0 | 0 | 0 | 0 | 0 | 1H | 0 | 0 | 0 | 2H | 0 | 0 | 0 | 0 | 0 | 0 | 0 | 0 | 2H | 7H | 2H |

POSTEMERGENCE

| | CMPD 62 | | CMPD 63 | | CMPD 64 | | CMPD 65 | | CMPD 66 | | CMPD 67 | | CMPD 68 | | CMPD 69 | | CMPD 70 | | CMPD 71 | | CMPD 72 | | CMPD 73 | |
|---|---|---|---|---|---|---|---|---|---|---|---|---|---|---|---|---|---|---|---|---|---|---|---|---|
| RATE = KG/HA | 0.05 | 0.01 | 0.05 | 0.01 | 0.4 | 0.05 | 0.05 | 0.01 | 0.05 | 0.01 | 0.05 | 0.01 | 0.05 | 0.01 | 0.05 | 0.01 | 0.4 | 0.05 | 0.4 | 0.05 | 0.4 | 0.05 | 0.4 | 0.05 |
| COTTON | 10B | 10B | 10B | 10B | 10B | 10B | 10B | 10B | 10B | 10B | 10B | 9B | 10B | 9B | 10B | 9B | 10B | 10B | 10B | 10B | 10B | 3B | 10B | 10B |
| MORNINGGLORY | 10B | 8B | 10B | 10B | 10B | 10B | 10B | 10B | 8B | 6B | 7B | 8B | 9B | 10B | 7B | 10B | 10B | 10B | 10B | 10B | 10B | 10B | 10B | 10B |
| COCKLEBUR | 10B | 7B | 9B | 7B | 10B | 10B | 7B | 1B | 6B | 0 | 7B | 8B | 3B,7H | 7B | 10B | 7B | 9B | 7B | 7B | 5B | 5B | 5B | 7B | 7B |
| NUTSEDGE | 1B | 0 | 2B | 1B | — | 4B | 1B | 1B | 0 | 0 | 5B | 0 | 1B | 1B | 2B | 1B | 1B | 1B | 5B | 2B | 4B | — | 4B | — |
| CRABGRASS | 2B | 2B | 5B | 3B | 5B | 4B | 2B | 2B | 2B | 0 | 4B | 4B | 2B | 2B | 7B | 2B | 3B | 3B | 4B | 1B | 5B | 3B | 6B | 1B |
| BARNYARDGRASS | 5B | 1B | 7B | 2B | 6B | 8B | 3B | 3B | 2B | 2B | 7B | 6B | 7B | 3B | 5B | 1B | 3B | 1B | 7B | 3B | 10B | 3B | 9B | 2B |
| WILD OATS | 2B | 1B | 6B | 2B | 10B | 8B | 2B | 1B | 1B | 1B | 5B | 2B | 5B | 2B | 2B | 2B | 3B | 3B | 4B | 4B | 5B | 2B | 6B | 3B |
| WHEAT | 3B | 1B | 4B | 6B | 9B | 5B | 3B | 1B | 5B | 2B | 5B | 2B | 3B | 1B | 1B | 1B | 6B | 1B | 3B | 1B | 3B | 1B | 5B | 1B |
| CORN | 2B | 1B | 4B | 2B | 5B,8H | 4B | 2B | 0 | 2B | 1B | 4B | 4B | 1B | 1B | 1B | 3B | 3B | 1B | 3B | 1B | 7B | 2B | 2B | 1B |
| SOYBEANS | 1B,1H | 1H | 7B | 3B,6H | 10B | 5B | 1B | 2B | 2B | 1B | 4B | 2B | 7B | 2B | 3B | 1B | 8B | 2B | 7B | 3B | 55B | 1B | 4B | 1B |
| RICE | 2B | 1B | 2B | 1B | 5B | 5B | 1B | 1B | 5B | 2B | 2B | 1B | 2B | 1B | 2B | 3B | 2B | 1B | 7B | 3B | 5B | 4B | 4B | 4B |
| SORGHUM | 4B | 2B | 3B | 3B | 7B | 4B | 2B | 1B | 3B | 2B | 4B | 3B | 1B | 1B | 5B | 4B | 3B | 1B | 4B | 2B | 5B | 3B | 5B | 5B |
| CHEATGRASS | 1B | 0 | 0 | 0 | 6B | 4B | 1B | 0 | 2B | 0 | 4B | 3B | 0 | 0 | 1B | 1B | 3B | 0 | — | 3B | 5B | 3B | 9B | 7B |
| SUGARBEETS | 9B | 4B | 7B | 5B | 10B | 10B | 9B | 4B | 8B | 5B | 9B | 5B | 3B,4H | 0 | 9B | 6B | 10B | 10B | 10B | 9B | 10B | 6B | 10B | 8B |
| VELVETLEAF | 9B | 3B | 6B | — | 10B | 10B | 2B | 1B | 10B | 7B | 10B | 7B | 5B | 3B | 7B | 3B | 9B | 3B | 10B | — | — | 10B | 10B | 10B |
| GIANT FOXTAIL | 7B | 3B | 6B | 5B | 9B | 9B | 6B | 3B | 6B | 2B | 8B | 2B | 3B | 1B | 9B | 3B | 7B | 2B | 5B | 3B | 5B | 1B | 6B | 2B |
| BARLEY | 1B | 1B | 3B | 1B | 10B | 4B | 1B | 0 | 1B | 1B | 3B | 2B | 0 | 0 | 3B | 1B | 5B | 5B | 6B | 3B | 2B | 2B | 2B | 3B |
| DOWNY BROME | | | | | | | | | | | | | | | | | 7B | | | 4B | | | | |

PREEMERGENCE

| | CMPD 62 | | CMPD 63 | | CMPD 64 | | CMPD 65 | | CMPD 66 | | CMPD 67 | | CMPD 68 | | CMPD 69 | | CMPD 70 | | CMPD 71 | | CMPD 72 | | CMPD 73 | |
|---|---|---|---|---|---|---|---|---|---|---|---|---|---|---|---|---|---|---|---|---|---|---|---|---|
| RATE = KG/HA | 0.05 | 0.01 | 0.05 | 0.01 | 0.4 | 0.05 | 0.05 | 0.01 | 0.05 | 0.01 | 0.05 | 0.01 | 0.05 | 0.01 | 0.05 | 0.01 | 0.4 | 0.05 | 0.4 | 0.05 | 0.4 | 0.05 | 0.4 | 0.05 |
| COTTON | 0 | 4H | 0 | 0 | 7G | 0 | 0 | 0 | 0 | 0 | 2H | 0 | 0 | 0 | 0 | 0 | 2H | 0 | 2C,9G | 0,1C | 10C | 0 | 0 | 0 |
| MORNINGGLORY | 3C,9H | 0 | 3C,9H | 0 | 10C | 3C,8H | 0 | 0 | 4G | 0 | 4G | 0 | 3C,6H | 0 | 7H | 0 | 9H | 2H | 2G | 0,2G | 10C | 9C | 10C | 2G |
| COCKLEBUR | 0 | 0 | 2G | 0 | 3C,7H | 0 | 3G | 0 | 2G | 0 | 0 | 0 | 2G | 0 | 2H | 0 | 6H | 2H | 7G | 0,0 | 5G | 0 | 0 | 0 |
| NUTSEDGE | 0 | 0 | 0 | 0 | 0 | 0 | 0 | 0 | 0 | 0 | 4G | 0 | 0 | 0 | 0 | 0 | 0 | 0 | 7G | 0,0 | 0 | 0 | 0 | 0 |
| CRABGRASS | 0 | 0 | 0 | 0 | 2H | 3C,9H | 0 | 0 | 4G | 0 | 0 | 0 | 0 | 0 | 2G | 0 | 7H | 2H | 6G | 0,2G | 3G | 0 | 0 | 0 |
| BARNYARDGRASS | 0 | 0 | 0 | 0 | 2G | 5C,9G | 0 | 0 | 4G | 2G | 0 | 0 | 0 | 0 | 2G | 0 | 0 | 2H | 10H | 5H,4H | 0 | 0 | 0 | 0 |
| WILD OATS | 0 | 0 | 0 | 0 | 3G | 2G | 0 | 0 | 0 | 0 | 0 | 0 | 0 | 0 | 0 | 0 | 0 | 0 | 6C | 0,2G | 0 | 0 | 0 | 0 |
| WHEAT | 0 | 0 | 0 | 0 | 0 | 0 | 0 | 0 | 0 | 0 | 0 | 0 | 0 | 0 | 0 | 0 | 0 | 0 | 3C | 0,0 | 0 | 0 | 0 | 0 |
| CORN | 0 | 0 | 0 | 0 | 2G | 0 | 0 | 0 | 0 | 0 | 0 | 0 | 0 | 0 | 0 | 0 | 0 | 0 | 3G | 0,0 | 0 | 0 | 0 | 0 |
| SOYBEANS | 0 | 0 | 0 | 0 | 2G | 0 | 0 | 0 | 0 | 0 | 0 | 0 | 0 | 0 | 0 | 0 | 0 | 0 | 3G | 0,0 | 0 | 0 | 0 | 0 |
| RICE | 0 | 0 | 0 | 0 | 2G | 0 | 0 | 0 | 0 | 0 | 0 | 0 | 0 | 0 | 0 | 0 | 0 | 0 | 4C | 0,0 | 0 | 0 | 0 | 0 |
| SORGHUM | 0 | 0 | 0 | 0 | 2G | 0 | 0 | 0 | 0 | 0 | 0 | 0 | 0 | 0 | 0 | 0 | 0 | 0 | 3C,7G | 0,0 | — | 0 | 0 | 0 |
| CHEATGRASS | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 |
| SUGARBEETS | 0 | 0 | 5G | 0 | 10H | 3C,9H | 0 | 0 | 6H | 0 | 5H | 0 | 2C,6H | 0 | 3G | 0 | 10H | 4H | 10C | 5G,5G | 8G | 0 | 10C | 0 |
| VELVETLEAF | 6G | 0 | 3G | 0 | 10E | 5C,9G | 0 | 0 | 10C | 0 | 4G | 0 | 5G | 0 | 1H | 0 | 10H | 8H | 10C | 5G,0 | 10C | 0 | 2G | 0 |
| GIANT FOXTAIL | 0 | 0 | 0 | 0 | 10H | 2G | 0 | 0 | 3C,9H | 0 | 2G | 0 | 0 | 0 | 6H | 0 | 6H | 2H | 7G | 3G,2G | 0 | 0 | 0 | 0 |
| BARLEY | 0 | 0 | 0 | 0 | 2G | 0 | 0 | 0 | 0 | 0 | 0 | 0 | 0 | 0 | 0 | 0 | 0 | 0 | 2G | 0,0 | 0 | 0 | 0 | 0 |

TABLE A-continued

| DOWNY BROME | CMPD 74 | | CMPD 75 | | | CMPD 76 | | CMPD 77 | | CMPD 78 | | CMPD 79 | | CMPD 80 | | CMPD 81 | | CMPD 82 | | CMPD 83 | | CMPD 84 | |
|---|---|---|---|---|---|---|---|---|---|---|---|---|---|---|---|---|---|---|---|---|---|---|---|
| RATE = KG/HA | 0.4 | 0.05 | 0.4 | 0.05 | 0.01 | 0.05 | 0.01 | 0.05 | 0.01 | 0.05 | 0.01 | 0.4 | 0.1 | 0.4 | 0.05 | 0.4 | 0.05 | 0.4 | 0.05 | 0.4 | 0.05 | 0.4 | 0.05 |
| POSTEMERGENCE | | | | | | | | | | | | | | | | | | | | | | | |
| COTTON | 10B | 10B | 10B | 10B | 10B | 10B | 9B | 8B | 10B | 10B | 10B | 10B | 10B | 9B | 7B | 0 | 0 | 9B | 2B,8G | 9B | 9B | 10B | 9B |
| MORNINGGLORY | 10B | 8B | 10B | 10B | 8B | 10B | 8B | 10B | 5B | 10B | 9B | 10B | 10B | 8B | 7B | 0 | 0 | 8B | 6B | 8B | 8B | 3B | 1B |
| COCKLEBUR | 9B | 7B | 10B | 10B | 6B | 10B | 5B | 10B | 4B | 10B | 7B | 10B | 8B | 5B | 5B | 0 | 0 | 4B | 1B | 6B | 6B | 2B | 0 |
| NUTSEDGE | 5B | 1B | 3B,9G | 9G | 3B | 7B | 1B | 4B | 1B | 1B | 1B | 0 | 0 | 3B | 1B | 0 | 0 | 0 | 0 | — | 0 | 0 | 0 |
| CRABGRASS | 4B | 2B | 10B | 9B | 2B | 4B | 1B | 6B | 1B | 2B | 1B | 5B | 2B | 4B | 1B | 0 | 0 | 4B | 1B | 3B | 4B | 1B | 1B |
| BARNYARDGRASS | 9B | 4B | 10B | 10B | 6B | 9B | 2B | 9B | 2B | 6B | 5B | 9B | 8B | 8B | 2B | 0 | 0 | 5B | 2B | 8B | 2B | 8B | 1B |
| WILD OATS | 9B | 3B | 10B | 5B | 3B | 7B | 3B | 6B | 3B | 5B | 1B | 3B | 2B | 7B | 1B | 0 | 0 | 6B | 1B | 6B | 2B | 1B | 1B |
| WHEAT | 4B | 3B | 6B | 3B | 2B | 5B | 2B | 6B | 2B | 2B | 1B | 2B | 2B | 5B | 1B | 0 | 0 | 5B | 1B | 3B | 2B | 1B | 0 |
| CORN | 3B | 4B | 3B | 2B | 2B | 3B | 2B | 5B | 4B | 1B | 1B | 4B | 2B | 8B | 2B | 0 | 0 | 5B | 1B | 4B | 2B | 0 | 0 |
| SOYBEANS | 4B | 3B | 10B | 9B | 7B | 4B | 4B | 7B | 2B | 2B | 3B | 2B | 2B | 5B | 5B | 0 | 0 | 3B | 2B | 6B | 3B | 1B | 1B |
| RICE | 8B | 7B | 9B | 6B | 4B | 8B | 3B | 8B | 2B | 3B | 1B | 7B | 4B | 8B | 3B | 0 | 0 | 5B | 2B,2H | 8B | 4B | 1B | 2B |
| SORGHUM | 5B | 4B | 9B | 6B | 3B | 8B | 3B | 8B | 4B | 1B | 2B | 4B | 1B | 4B | 2B | 0 | 0 | 3B | 4B | 5B | 3B | 3B | 0 |
| CHEATGRASS | 5B | 1B | 10B | 5B | 2B | 6B | 1B | 6B | 2B | 5B | 5B | 4B | 0 | 4B | 1B | 0 | 0 | 3B | 1B | 5B | 1B | 1B | 0 |
| SUGARBEETS | 9B | 8B | 10B | 10B | 6B | 9B | 3B | 10B | 8B | 8B | 4B | 10B | 10B | 7B | 2B | 0 | 0 | 6B | 1B | 6B | 7B | 3B,5H | 0 |
| VELVETLEAF | 8B | 8B | 10B | 10B | 7B | 9B | 3B | 10B | 8B | 8B | 6B | 10B | 9B | 9B | 3B | 0 | 0 | 9B | 5B | 10B | 7B | 6B | 1B |
| GIANT FOXTAIL | 10B | 2B | 10B | 8B | 2B | 6B | 1B | 9B | 3B | 5B | 4B | 6B | 5B | 6B | 2B | 0 | 0 | 7B | 2B | 5B | 6B | 3B | 1B |
| BARLEY | 5B | 3B | 9B | 7B | 2B | 5B | 3B | 5B | 3B | 1B | 1B | 2B | 1B | 3B | 1B | 0 | 0 | 3B | 1B | 6B | 3B | 1B | 1B |

| | CMPD 74 | CMPD 75 | | CMPD 76 | | CMPD 77 | CMPD 78 | CMPD 79 | CMPD 80 | CMPD 81 | CMPD 82 | CMPD 83 | CMPD 84 |
|---|---|---|---|---|---|---|---|---|---|---|---|---|---|
| RATE = KG/HA | 0.4 | 0.4 | 0.05 | 0.4 | 0.05 | 0.01 | 0.01 | 0.4 | 0.4 | 0.05 | 0.4 | 0.4 | 0.4 | 0.05 |
| PREEMERGENCE | | | | | | | | | | | | | | |
| COTTON | 4G | 3H | 0 | 0 | 2G | 0 | 0 | 10E | 2C | 3G | 0 | 1C,3H | 0 | 0 |
| MORNINGGLORY | 3G | 9H | 1H | 7G | 7G | 2G | — | 10E | 10C | 3G | 0 | 3C | 0 | 0 |
| COCKLEBUR | 5G | 2H | 0 | 5G | 2C,7G | 5G | 0 | 8H | 2G | 0 | — | 99G | — | 0 |
| NUTSEDGE | 0 | 10E | 0 | 3C,5G | 4G | 0 | 0 | 10E | 3C,9G | 0 | 0 | 9H | 0 | 0 |
| CRABGRASS | 5G | 10H | 9H | 7G | 5G | 4G | 2C,5H | 8H | 0 | 0 | 0 | 1C | 0 | 2H |
| BARNYARDGRASS | 6H | 10H | 3H | 0 | 3C,7H | 4C,9H | 2C | 8H | 0 | 7G | 0 | 2C | 0 | 0 |
| WILD OATS | 3G | 8H | 0 | 0 | 3C,5G | 7C | 0 | 3H | 0 | 0 | 5G | 3C,5G | 0 | 0 |
| WHEAT | 0 | 5H | 0 | 0 | 3C,6G | 6C | 0 | 3C,4G | 0 | 5G | 0 | 3C,6G | 0 | 0 |
| CORN | 0 | 3C,7H | 1C | 0 | 3C,7G | 3C,7H | 0 | 3G | 1C | 0 | 0 | 2C,5H | 0 | 0 |
| SOYBEANS | 0 | 10H | 5G | 0 | 2H | 7H | 0 | 0 | 2G | 0 | 0 | 2C,7H | 0 | 0 |
| RICE | 0 | 8H | 0 | 3H | 5G | 6G | 3C,5H | 6G | 2G,5G | 0 | 2G | 3C | 0 | 0 |
| SORGHUM | 2G | 6H | 3H | 2H | 3C,5H | 5G | 4G | 7G | 2C,5G | 0 | 0 | 1C | 0 | 0 |
| CHEATGRASS | 0 | 4H | 2H | 0 | 0 | 4G | 4G | 10C | 0 | 4G | 0 | 2C,8H | 0 | 0 |
| SUGARBEETS | 9C | 10H | 7H | 2C,4G | 2C,4G | 4G | 3G | 10C | 9C | 5G | 0 | 9C | 2H | 0 |
| VELVETLEAF | 8G | 10H | 10H | 10C | 10C | 4G | 0 | 9C | 10C | 0 | 4G | 4C,9H | 0 | 0 |
| GIANT FOXTAIL | 6G | 10H | 10H | 10E | 10E | 5G | 0 | 7H | 8G | 5G | 0 | 7H | 0 | 0 |
| BARLEY | 0 | 2H | 0 | 8C | 1C | 7C | 0 | 4G | 5C | 0 | 0 | 0 | 0 | 0 |

| | CMPD 85 | CMPD 86 | CMPD 87 | CMPD 88 | CMPD 89 | | CMPD 90 | CMPD 91 | CMPD 92 | CMPD 93 | CMPD 94 | CMPD 95 | CMPD 96 |
|---|---|---|---|---|---|---|---|---|---|---|---|---|---|
| RATE = KG/HA | 0.4 | 0.05 | 0.4 | 0.05 | 0.4 | 0.05 | 0.05 | 0.4 | 0.05 | 0.4 | 0.05 | 0.4 | 0.05 | 0.4 | 0.05 | 0.05 | 0.4 | 0.05 | 0.4 | 0.05 | 0.4 | 0.05 |
| POSTEMERGENCE | | | | | | | | | | | | | | |
| COTTON | 10B | 8B | 10B | 10B | 7B | 3B | 1B | 0 | 3C | 0 | 1B | 0 | 9B | 8B | 10B | 10B | 2B | 1B | 2G | 9B | 9B |
| MORNINGGLORY | 7B | 3B | 7B | 1B | 3B | 3B | 1B | 0 | 2C,2H | 1C,1H | 1B | 0 | 8B | 5B | 10B | 10B | 1B | 0 | 8H | 9B | 7B |
| COCKLEBUR | 5B | 3B | 1B | 1B | 2B | — | 0 | 0 | 0 | 0 | 0 | 0 | 5B | 4B | 10B | 8B | 0 | 0 | 7G | 5B | 5B |
| NUTSEDGE | 2B | — | 1B | 1B | 0 | — | 0 | 0 | 2G | 0 | 0 | 0 | 1B | 1B | 3B,8G | 9B | 0 | 0 | 3C | 2B | 0 |
| CRABGRASS | 5B | 2B | 1B | 1B | 1B | 0 | 0 | 0 | 0 | 0 | 0 | 0 | 1B | 1B | 10B | | 0 | 0 | 4B | 2B | 2B |

TABLE A-continued

| | CMPD 85 | | CMPD 86 | | CMPD 87 | | CMPD 88 | | CMPD 89 | | CMPD 90 | | CMPD 91 | | CMPD 92 | | CMPD 93 | | CMPD 94 | | CMPD 95 | | CMPD 96 | |
|---|---|---|---|---|---|---|---|---|---|---|---|---|---|---|---|---|---|---|---|---|---|---|---|---|
| | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 |
| BARNYARDGRASS | 6B | 2B | 4B | 2B | 4B | 0 | 0 | 0 | 0 | 0 | 0 | 0 | 2B | 2B | 10B | 5B | 7B | 0 | 9B | 5B,9H | 6B | 3B | 3B | 1B |
| WILD OATS | 2B | 1B | 3B | 2B | 0 | 0 | 0 | 0 | 0 | 0 | 0 | 0 | 2B | 2B | 5B | 3B | 2B | 0 | 5B,9H | 3B | 3B | 2B |
| WHEAT | 2B | 1B | 3B | 2B | 0 | 0 | 0 | 0 | 0 | 0 | 0 | 0 | 2B | 2B | 4B | 3B | 1B | 0 | 6B,9H | 4B | 2B | 1B |
| CORN | 4B | 3B | 7B | 3B | 2B | 1B | 0 | 0 | 1C | 0 | 0 | 0 | 3B | 2B | 3B | 1B | 1B | 0 | 9B | 5B | 5B | 2B |
| SOYBEANS | 6B | 2B | 5B | 3B | 1B | 1B | 0 | 0 | 0 | 0 | 0 | 0 | 5B | 2B | 9B | 5B | 5B | 1B | 9B | 8B | 6B | 3B |
| RICE | 5B | 4B | 5B | 4B | 4G | 0 | 0 | 0 | 0 | 0 | 2B | 0 | 3B | 4B | 6B | 3B | 1B | 0 | 8B | 5B | 5B | 2B |
| SORGHUM | 3B | 3B | 4B | 3B | 0 | 0 | 0 | 0 | 1C | 0 | 0 | 0 | 3B | 2B | 3B | 2B | 3B | 0 | 9B | 5B | 6B | 4B |
| CHEATGRASS | 1B | 0 | 3B | 1B | 3B | 0 | 0 | 0 | 0 | 0 | 1B | 0 | — | — | 6B | 3B | 3B | 0 | 2B | 1B | 1B | 0 |
| SUGARBEETS | 8B | 3B | 5B | 2B | 1B | 1B | 0 | 0 | 1C | 0 | 0 | 0 | 5B | 3B | 10B | 9B | 9B | 0 | 9B | 7B | 5B | 2B |
| VELVETLEAF | 10B | 7B | 9B | 7B | 3B | 0 | 0 | 0 | 6G | 0 | 0 | 0 | 7B | 5B | 10B | 10B | 10B | 4B | 10B | 10B | 10B | — |
| GIANT FOXTAIL | 3B | 1B | 4B | 1B | 2B | 0 | 0 | 0 | 0 | 0 | 0 | 0 | 3B | 3B | 9B | 4B | 4B | 0 | 9B | 4B | 4B | 1B |
| BARLEY | 2B | 1B | 3B | 2B | 0 | 0 | 0 | 0 | 0 | 0 | 0 | 0 | 2B | 2B | 2B | 0 | 5B | 3B | 1B |
| DOWNY BROME | | | | | | | | | | | | | — | — | 4B | | | | | | | |

| | CMPD 85 | | CMPD 86 | | CMPD 87 | | CMPD 88 | | CMPD 89 | | CMPD 90 | | CMPD 91 | | CMPD 92 | | CMPD 93 | | CMPD 94 | | CMPD 95 | | CMPD 96 | |
|---|---|---|---|---|---|---|---|---|---|---|---|---|---|---|---|---|---|---|---|---|---|---|---|---|
| RATE = KG/HA | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 | 0.4 | 0.05 |
| PREEMERGENCE | | | | | | | | | | | | | | | | | | | | | | | | |
| COTTON | 0 | 0 | 0 | 0 | 0 | 0 | 0 | 0 | 0 | 0 | 0 | 0 | 3C,5G | 2G | 1H | 0 | 0 | 0 | 9C | 2C,5G | 0 | 0 |
| MORNINGGLORY | 0 | 0 | 0 | 0 | 0 | 0 | 0 | 0 | 0 | 0 | 0 | 0 | 2C,7G | 0 | 6H | 0 | 0 | 0 | 10C | 9C | 4G | 0 |
| COCKLEBUR | 0 | 0 | 0 | 0 | 0 | 0 | 0 | 0 | 0 | 0 | 0 | 0 | — | 0 | 9H | 0 | 0 | 0 | 9C | 2C,5G | — | 0 |
| NUTSEDGE | 0 | 0 | 0 | 0 | 0 | 0 | 0 | 0 | 0 | 0 | 0 | 0 | 0 | 0 | 0 | 0 | 0 | 0 | 9C | 0 | 0 | 0 |
| CRABGRASS | 7H | 0 | 6G | 0 | 0 | 0 | 0 | 0 | 0 | 0 | 4G | 0 | 3C,9H | 0 | 10H | 7H | 0 | 0 | 10H | 10H | 3H | 0 |
| BARNYARDGRASS | 1H | 0 | 1H | 0 | 0 | 0 | 0 | 0 | 0 | 0 | 0 | 0 | 8C | 0 | 8H | 0 | 0 | 0 | 9H | 1C | 0 | 0 |
| WILD OATS | 0 | 0 | 0 | 0 | 0 | 0 | 0 | 0 | 0 | 0 | 0 | 0 | 3C,6G | 0 | 2H | 0 | 0 | 0 | 3C,8H | 2C,5H | 0 | 0 |
| WHEAT | 0 | 0 | 0 | 0 | 0 | 0 | 0 | 0 | 0 | 0 | 0 | 0 | 4C,8H | 0 | 0 | 0 | 0 | 0 | 5C,9H | 1C | 0 | 0 |
| CORN | 0 | 0 | 0 | 0 | 0 | 0 | 0 | 0 | 0 | 0 | 0 | 0 | 5C,9H | 0 | 1H | 0 | 0 | 0 | 9C | 3C,6G | 0 | 0 |
| SOYBEANS | 0 | 0 | 0 | 0 | 0 | 0 | 0 | 0 | 0 | 0 | 0 | 0 | 3C,7G | 0 | 3H | 0 | 0 | 0 | 5C,9H | 3C,9G | 0 | 0 |
| RICE | 0 | 0 | 0 | 0 | 0 | 0 | 0 | 0 | 0 | 0 | 0 | 0 | 7C | 2C | 6H | 0 | 0 | 0 | 9H | 4C,6G | 0 | 0 |
| SORGHUM | 0 | 0 | 0 | 0 | 0 | 0 | 0 | 0 | 0 | 0 | 0 | 0 | 9C | 2C | 0 | 0 | 0 | 0 | 9H | 3C,5G | 0 | 0 |
| CHEATGRASS | 0 | 0 | 0 | 0 | 0 | 0 | 0 | 0 | 0 | 0 | 0 | 0 | 3G | 2G | 6H | 0 | 0 | 0 | 3C | 0 | 0 | 0 |
| SUGARBEETS | 0 | 2G | 0 | 0 | 0 | 0 | 0 | 0 | 0 | 0 | 0 | 0 | 3C,8G | 8B | 10H | 10H | 2H | 0 | 10C | 9C | 0 | 0 |
| VELVETLEAF | 0 | 2H | 0 | 0 | 0 | 0 | 0 | 0 | 0 | 0 | 2G | 0 | 10C | 2G | 10H | 10H | 3H | 0 | 10C | 10C | 0 | 0 |
| GIANT FOXTAIL | 2G | 0 | 2H | 0 | 0 | 0 | 0 | 0 | 0 | 0 | 0 | 0 | 10H | 6G | 10H | 10H | 4H | 0 | 10H | 9H | 2H | 0 |
| BARLEY | 0 | 0 | 0 | 0 | 0 | 0 | 0 | 0 | 0 | 0 | 0 | 0 | 8C | 0 | 0 | 0 | 0 | 0 | 4C | 0 | 0 | 0 |
| DOWNY BROME | | | | | | | | | | | | | — | — | | | | | | | | |

| | CMPD 97 | CMPD 98 | CMPD 99 | CMPD 100 | CMPD 101 |
|---|---|---|---|---|---|
| RATE = KG/HA | 0.05 | 0.05 | 0.05 | 0.05 | 0.05 |
| POSTEMERGENCE | | | | | |
| COTTON | 10B | 10B | 10B | 9B | 10B |
| MORNINGGLORY | 10B | 10B | 10B | 10B | 10B |
| COCKLEBUR | 9B | 7B | 8B | 9B | 9B |
| NUTSEDGE | 5B | 5B | — | 3B | 5B |
| CRABGRASS | 5B | 3B | 4B | 5B | 4B |
| BARNYARDGRASS | 9B | 7B | 7B | 9B | 5B |
| WILD OATS | 5B | 5B | 5B | 5B | 5B |
| WHEAT | 5B | 4B | 4B | 2B | 2B |
| CORN | 3B | 5B | 5B | 2B | 1B |
| SOYBEANS | 7B | 6B | 9B | 4B | 4B |
| RICE | 6B | 5B | 5B | 5B | 6B |
| SORGHUM | 4B | 4B | 5B | 4B | 2B |
| CHEATGRASS | — | 3B | 4B | 2B | 8B |
| SUGARBEETS | 5B | 9B | 10B | 10B | 10B |

TABLE A-continued

|  | CMPD 97 | CMPD 98 | CMPD 99 | CMPD 100 | CMPD 101 |
|---|---|---|---|---|---|
| VELVETLEAF | 10B | 10B | 10B | 9B | 10B |
| GIANT FOXTAIL | 7B | 5B | 7B | 9B | 4B |
| BARLEY | 3B | 3B | 6B | 3B | 1B |
| DOWNY BROME | 6B | — | | | |
| RATE = KG/HA | 0.05 | 0.05 | 0.05 | 0.05 | 0.05 |
| PREEMERGENCE | | | | | |
| COTTON | 0 | 0 | 0 | 0 | 0 |
| MORNINGGLORY | 0 | 0 | 0 | 0 | 2G |
| COCKLEBUR | 3G | 0 | 0 | 0 | 0 |
| NUTSEDGE | 2C | 2G | 0 | 0 | 0 |
| CRABGRASS | 3C,8G | 0 | 3G | 0 | 0 |
| BARNYARDGRASS | 0 | 0 | 0 | 0 | 0 |
| WILD OATS | 0 | 0 | 0 | 0 | 0 |
| WHEAT | 0 | 0 | 0 | 0 | 0 |
| CORN | 0 | 0 | 0 | 0 | 0 |
| SOYBEANS | 0 | 0 | 0 | 0 | 0 |
| RICE | 3C | 0 | 2G | 0 | 0 |
| SORGHUM | 2C | 0 | 0 | 0 | 0 |
| CHEATGRASS | — | 0 | 0 | 0 | 0 |
| SUGARBEETS | 0 | 5G | 0 | 5G | 4G |
| VELVETLEAF | 2G | 2G | 0 | 5G | 0 |
| GIANT FOXTAIL | 3C,6G | 0 | 0 | 0 | 0 |
| BARLEY | 0 | — | | | |
| DOWNY BROME | 0 | | | | |

It is noted that several compounds of this test show little or no activity; it is thought that greater activity would be shown at higher rates of use.

In the following examples, the species of plants that were tested were:

|  | Abbreviation |
|---|---|
| Barnyardgrass (watergrass) - *Echinochloa crus-galli* | BYGR |
| Downy brome - *Bromus tectorum* | DOBR |
| Yellow foxtail - *Setaria glauca* | YEFT |
| Sicklepod - *Cassia obtusifolia* | SIPO |
| Velvetleaf - *Abutilon theophrasti* | VELE |
| Garden cress - *Lepidium sativum* | GACR |
| Johnsongrass - *Sorghum halepense* | JOGR |
| Morningglory - Ipomoea sp. | MOGL |
| Field bindweed - *Convolvulus arvensis* | FIBW |
| Nightshade - Solanum sp. | NISH |
| Blackgrass - *Alopercurus myosurides* | BLGR |
| Yellow millet - *Panicum miliceum* | YEMI |
| Large crabgrass - *Digitaria sanguinalis* | LACG |
| Redroot pigweed - *Amaranthus retroflexus* | RRPW |
| Hemp sesbania - *Sesbania exaltata* | HESE |
| Prickly sida - *Sida spinosa* | PRSI |

Test Procedures

The preemergence (soil) herbicidal activity of compounds of formula I were evaluated by planting seeds of downy brome, johnsongrass, yellow foxtail, barnyardgrass, yellow millet, blackgrass, hemp sesbania, velvetleaf, morningglory, prickly sida, sicklepod and garden cress in test tubes, nominally measuring 25×200 millimeters, filled about three-quarters full of untreated soil, in each case covered on top with about 2.5 cubic centimeters of soil, treated with 0.1 milligram of the test compound, to give a dosage of 1.0 Pound of test compound per acre. The seeds were planted on top of the treated soil and covered with about 1.5 cubic centimeters of untreated soil. The planted soil was held under a controlled regiment of temperature, moisture, and light. At 10 days, the amounts of germination and growth in each tube were evaluated on a 0 to 9 scale.

The postemergence (foliar) herbicidal activity of compounds of formula I were evaluated by spraying 9-day-old large crabgrass plants, 9-day-old pigweed plants, 6-day-old johnsongrass plants, 9-day-old velvetleaf plants, 8-day-old yellow foxtail plants, 9-day-old sicklepod plants, 5-day-old morningglory plants, 5-day-old barnyardgrass plants, 6-day-old yellow millet plants, 9-day-old nightshade plants, 9-day-old prickly sida plants and 7-day-old field bindweed plants to runoff with 2.4 milliliters of a liquid formulation containing 0.5 milligram of the test compound (one pound of the test compound per acre). The sprayed plants were held under a controlled regiment of temperature, moisture and light for 7 to 8 days, when the effect of the test compound was evaluated visually.

Results of the preemergence and postemergence herbicidal activity tests are set forth in Tables 1 and 22.

TABLE A-1

Preemergence

| CMPD NO. | DOBR | JOGR | YEFT | BYGR | YEMI | BLGR |
|---|---|---|---|---|---|---|
| 102 | 0 | 6 | 3 | 7 | 5 | 0 |
| 103 | 6 | 7 | 4 | 7 | 7 | 7 |
| 104 | 0 | 3 | 0 | 4 | 0 | 4 |
| 105 | 7 | 7 | 6 | 8 | 7 | 6 |
| 106 | 0 | 5 | 3 | 3 | 0 | 3 |
| 107 | 3 | 3 | 4 | 4 | 3 | 3 |
| 108 | 0 | 0 | 0 | 0 | 0 | 0 |
| 109 | 5 | 6 | 6 | 6 | 6 | 5 |
| 110 | 5 | 4 | 5 | 6 | 6 | 3 |
| 111 | 0 | 0 | 0 | 0 | 0 | 0 |
| 112 | 0 | 0 | 0 | 0 | 0 | 0 |
| 113 | 0 | 0 | 0 | 0 | 0 | 0 |
| 114 | 3 | 0 | 4 | 4 | 3 | 0 |
| 115 | 3 | 0 | 0 | 5 | 0 | 3 |
| 116 | 0 | 0 | 0 | 0 | 0 | 0 |
| 117 | 7 | 5 | 5 | 7 | 8 | 3 |
| 118 | 0 | 0 | 0 | 0 | 0 | 0 |

| CMPD NO. | HESE | VELE | MOGL | PRSI | SIPO | GACR |
|---|---|---|---|---|---|---|
| 102 | 0 | 0 | 0 | 6 | 0 | 5 |
| 103 | 8 | 8 | 8 | 9 | 3 | 9 |
| 104 | 5 | 7 | 0 | 8 | 0 | 6 |
| 105 | 8 | 9 | 9 | 9 | 7 | 9 |
| 106 | 3 | 9 | 8 | 9 | 0 | 9 |
| 107 | 3 | 9 | 7 | 9 | 0 | 9 |
| 108 | — | 3 | 0 | 3 | 0 | 9 |
| 109 | 8 | 6 | 6 | 8 | 3 | 9 |
| 110 | 7 | 7 | 3 | 8 | 0 | 9 |
| 111 | 0 | 3 | 5 | 8 | 0 | 8 |
| 112 | 0 | 0 | 0 | 0 | 0 | 0 |
| 113 | 2 | 5 | 4 | 8 | 2 | 9 |
| 114 | 3 | 9 | 9 | 9 | 3 | 9 |
| 115 | 3 | 7 | 5 | 9 | 0 | 9 |
| 116 | 0 | 4 | 7 | 3 | 0 | 6 |
| 117 | 9 | 9 | 9 | 9 | 0 | 9 |
| 118 | 0 | 0 | 0 | 0 | 0 | 0 |

TABLE A-2

Postemergence

| CMPD NO. | DOBR | JOGR | YEFT | BYGR | YEMI | BLGR |
|---|---|---|---|---|---|---|
| 102 | 3 | 3 | 3 | 3 | 5 | 7 |
| 103 | 5 | 9 | 9 | 8 | 8 | 9 |
| 104 | 7 | 9 | 9 | 9 | 9 | 9 |
| 105 | 7 | 6 | 9 | 6 | 7 | 9 |
| 106 | 3 | 2 | 2 | 3 | 3 | 6 |
| 107 | 8 | 9 | 9 | 9 | 8 | 9 |
| 108 | 2 | 7 | 7 | 7 | 7 | 6 |
| 109 | 3 | 5 | 5 | 3 | 3 | 7 |
| 110 | 3 | 4 | 5 | 3 | 3 | 5 |
| 111 | 6 | 5 | 8 | 7 | 6 | 9 |
| 112 | 5 | 3 | 4 | 3 | 4 | 5 |
| 113 | 8 | 9 | 9 | 8 | 8 | 9 |
| 114 | 6 | 9 | 9 | 6 | 7 | 9 |
| 115 | 8 | 9 | 9 | 9 | 9 | 9 |
| 116 | 4 | 7 | 6 | 3 | 5 | 9 |
| 117 | 9 | 5 | 9 | 9 | 8 | 9 |
| 118 | 3 | 4 | 3 | 3 | 5 | 3 |

| CMPD NO. | HESE | VELE | MOGL | PRSI | SIPO | GACR |
|---|---|---|---|---|---|---|
| 102 | 9 | 7 | 8 | 6 | 3 | 9 |
| 103 | 9 | 9 | 9 | 9 | 8 | 9 |
| 104 | 9 | 9 | 9 | 9 | 8 | 9 |
| 105 | 9 | 9 | 9 | 9 | 9 | 9 |
| 106 | 7 | 3 | 9 | 6 | 4 | 9 |
| 107 | 9 | 9 | 9 | 9 | 3 | 9 |
| 108 | 8 | 7 | 9 | 8 | 7 | 7 |
| 109 | 9 | 5 | 9 | 6 | 0 | 9 |
| 110 | 9 | 3 | 8 | 7 | 3 | 9 |
| 111 | 9 | 8 | 9 | 9 | 5 | 0 |
| 112 | 9 | 5 | 6 | 6 | 4 | 5 |
| 113 | 9 | 9 | 9 | 9 | 4 | 9 |
| 114 | 9 | 9 | 9 | 9 | 8 | 9 |
| 115 | 9 | 9 | 9 | 9 | 9 | 9 |
| 116 | 9 | 6 | 9 | 8 | 4 | 9 |
| 117 | 9 | 9 | 9 | 9 | 7 | 9 |
| 118 | 9 | 4 | 8 | 5 | 3 | 5 |

Test B

Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanguinalis*), sicklepod (*Cassia obtusifolia*), jimsonweed (*Datura stramonium*), velvetleaf (*Abutilon theophrasti*), lambsquarters (*Chenopodium album*), rice (*Oryza sativa*), and teaweed (*Sida spinosa*). The second pot was planted with green foxtail (*Setaria viridis*), cocklebur (*Xanthium pensylvanicum*), morningglory (*Ipomoea hederacea*), cotton (*Gossypium hirsutum*), johnsongrass (*Sorghum halepense*), barnyardgrass (*Echinochloa crus-galli*), corn (*Zea mays*), soybean (*Glycine max*), and giant foxtail (*Setaria faberi*). The third pot was planted with wheat (*Triticum aestivum*), barley (*Hordeum vulgare*), wild buckwheat (*Polygonum convolvulus* L.), downy brome (*Bromus tectorum* L.), sugarbeet (*Beta vulgaris*), wild oat (*Avena fatua* L.), common chickweed (*Stellaria media*), blackgrass (*Alopecurus myosuroides*), and rape (*Brassica napus*). The plants were grown for approximately fourteen days, then sprayed postemergence with the chemicals dissolved in a non-phytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvetleaf, lambsquarters, rice, and teaweed. The second pot was planted with green foxtail, cocklebur, morningglory, cotton, johnsongrass, barnyardgrass, corn, soybean, and giant foxtail. The third port was planted with wheat, barley, wild buckwheat, downy brome, sugarbeet, wild oat, chickweed, blackgrass, and rape. The three pans were sprayed preemergence with the chemicals dissolved in a non-phytotoxic solvent.

Treated plants and controls were maintained in the greenhouse for approximately 24 days, then all rated plants were compared to controls and visually reated for plant response.

Response ratings are based on a scale of 0 to 100 where 0=no effect, and 100=complete control. A dash (-) response means no test.

Response ratings are contained in Table B

TABLE B

| RATE = G/HA POSTEMERGENCE | CMPD 17 | | | | CMPD 42 | | | | CMPD 78 | | | | |
|---|---|---|---|---|---|---|---|---|---|---|---|---|---|
| | 0500 | 0250 | 0062 | 0016 | 0250 | 0062 | 0016 | 0004 | 0250 | 0062 | 0016 | 0004 | 0001 |
| GIANT FOXTAIL | 100 | 100 | 100 | 40 | 100 | 70 | 30 | 0 | 0 | 0 | 0 | 0 | 0 |
| VELVETLEAF | 100 | 100 | 100 | 100 | 100 | 100 | 100 | 30 | 100 | 90 | 70 | 50 | 0 |
| SUGARBEETS | 100 | 100 | 100 | 100 | 100 | 70 | 90 | 50 | 100 | 100 | 100 | 50 | 90 |
| CRABGRASS | 100 | 100 | 100 | 40 | 100 | 50 | 0 | 0 | 0 | 0 | 0 | 0 | 0 |
| TEAWEED | 100 | 100 | 100 | 100 | 100 | 100 | 70 | 20 | 100 | 80 | 60 | 50 | 0 |
| JIMSONWEED | 100 | 100 | 100 | 80 | 100 | 100 | 100 | 30 | 100 | 100 | 70 | 30 | 40 |
| RICE | 100 | 100 | 30 | 20 | 100 | 70 | 40 | 20 | 0 | 0 | 0 | 0 | 0 |
| COCKLEBUR | 100 | 70 | 60 | 40 | 80 | 70 | 80 | 20 | 40 | 30 | 0 | 0 | 0 |
| COTTON | 100 | 100 | 100 | 100 | 100 | 100 | 100 | 20 | 90 | 80 | 40 | 30 | 30 |
| SOYBEANS | 100 | 90 | 80 | 70 | 70 | 50 | 70 | 20 | 0 | 0 | 0 | 0 | 0 |
| BARNYARDGRASS | 100 | 100 | 100 | 20 | 100 | 90 | 40 | 0 | 30 | 0 | 0 | 0 | 0 |
| WILD OATS | 100 | 90 | 30 | 20 | 100 | 40 | 20 | 0 | 0 | 0 | 0 | 0 | 0 |
| MORNINGGLORY | 100 | 100 | 100 | 40 | 100 | 100 | 100 | 0 | 80 | 50 | 40 | 30 | 50 |
| WHEAT | 40 | — | 10 | 0 | 50 | 20 | 20 | 0 | 0 | 0 | 0 | 0 | 0 |
| SICKLEPOD | 100 | 90 | 80 | 50 | 100 | 80 | 40 | 0 | 0 | 0 | 0 | 0 | 0 |
| JOHNSONGRASS | 100 | 100 | 100 | 30 | 100 | 70 | 30 | 30 | 0 | 0 | 0 | 0 | 0 |
| NUTSEDGE | 100 | 80 | 50 | 30 | 50 | 40 | 20 | 0 | 0 | 0 | 0 | 0 | 0 |
| CORN | 90 | 80 | 10 | 0 | 30 | 40 | 20 | 0 | 0 | 0 | 0 | 0 | 0 |
| WILD BUCKWHEAT | 100 | 100 | 100 | 100 | 100 | 100 | 100 | 30 | 100 | 100 | 60 | 0 | 30 |
| BLACKGRASS | 100 | 100 | 90 | 40 | 50 | 30 | 0 | 0 | 30 | 0 | 0 | 0 | 0 |
| RAPE | 100 | 100 | 100 | 60 | 100 | 100 | 100 | 0 | 100 | 60 | 30 | 0 | 0 |
| BARLEY | 100 | 20 | 10 | 0 | 80 | 20 | 20 | 0 | 0 | 0 | 0 | 0 | 0 |
| GREEN FOXTAIL | 100 | 100 | 100 | 100 | 100 | 90 | 50 | 0 | 0 | 0 | 0 | 0 | 0 |
| CHEATGRASS | | | | | | | | | — | 50 | 30 | 0 | 0 |
| LAMBSQUARTER | 100 | 100 | 100 | 100 | 100 | 100 | 100 | 90 | 100 | 100 | 70 | 50 | 0 |
| CHICKWEED | 100 | 100 | — | 100 | 90 | 40 | 70 | 40 | 50 | 30 | 0 | 0 | 0 |
| DOWNY BROME | 100 | 100 | 30 | 0 | 30 | 10 | 30 | 0 | 0 | 0 | 0 | 0 | — |

| RATE = G/HA PREEMERGENCE | 0500 | 0250 | 0062 | 0016 | 0500 | 0250 | 0062 | 0016 | 0500 | 0250 | 0062 | 0016 |
|---|---|---|---|---|---|---|---|---|---|---|---|---|
| GIANT FOXTAIL | 100 | 100 | 100 | 100 | 100 | 100 | 90 | 70 | 100 | 70 | 30 | 0 |
| VELVETLEAF | 100 | 100 | 100 | 90 | 100 | 100 | 100 | 100 | 100 | 100 | 70 | 30 |
| SUGARBEETS | 100 | 100 | 100 | 70 | 100 | 100 | 30 | 50 | 100 | 100 | 80 | 40 |
| CRABGRASS | 100 | 100 | 100 | 100 | 100 | 100 | 100 | 90 | 100 | 90 | 80 | 70 |
| TEAWEED | 100 | 100 | 100 | 80 | 100 | 100 | 70 | 80 | 100 | 100 | 70 | 50 |
| JIMSONWEED | 100 | 100 | 100 | 40 | 100 | 100 | 100 | 80 | 90 | 70 | 0 | 0 |
| RICE | 100 | 100 | 100 | 90 | 90 | 90 | 40 | 20 | 0 | 0 | 0 | 0 |
| COCKLEBUR | 90 | 85 | 70 | 50 | 100 | 100 | 20 | 60 | 70 | 50 | 30 | 0 |
| COTTON | 100 | 100 | 60 | 20 | 100 | 80 | 40 | 0 | 60 | 30 | 0 | 0 |
| SOYBEANS | 100 | 100 | 70 | 30 | 60 | 80 | 10 | 0 | 20 | 0 | 0 | 0 |
| BARNYARDGRASS | 100 | 100 | 100 | 90 | 100 | 100 | 100 | 70 | 50 | 30 | 0 | 0 |
| WILD OATS | 100 | 80 | 50 | 20 | 100 | 100 | 70 | 30 | 30 | 0 | 0 | 0 |
| MORNINGLORY | 100 | 100 | 80 | 40 | 100 | 100 | 70 | 0 | 100 | 100 | 90 | 70 |
| WHEAT | 100 | 60 | 20 | 10 | 90 | 40 | 0 | 0 | 0 | 0 | 0 | 0 |
| SICKLEPOD | 100 | 100 | 90 | 50 | 100 | 100 | 90 | 0 | 60 | 30 | 0 | 0 |
| JOHNSONGRASS | 100 | 100 | 100 | 90 | 100 | 100 | 90 | 20 | 70 | 60 | 50 | 30 |
| NUTSEDGE | 100 | 100 | 60 | 20 | 60 | 30 | 0 | 20 | 0 | 0 | 0 | 0 |
| CORN | 100 | 100 | 100 | 50 | 90 | 80 | 70 | 20 | 0 | 0 | 0 | 0 |
| WILD BUCKWHEAT | 100 | 100 | 100 | 100 | 100 | 100 | 100 | 70 | 100 | 90 | 60 | 30 |
| BLACKGRASS | 100 | 100 | 100 | 40 | 80 | 70 | 50 | 20 | 50 | 30 | 0 | 0 |

TABLE B-continued

| | | | | | | | | | | | | |
|---|---|---|---|---|---|---|---|---|---|---|---|---|
| RAPE | 100 | 100 | 90 | 40 | 100 | 100 | — | 80 | 90 | 50 | 0 | 0 |
| BARLEY | 100 | 70 | 50 | 20 | 70 | 30 | 0 | 0 | 0 | 0 | 0 | 0 |
| GREEN FOXTAIL | 100 | 100 | 100 | 100 | 100 | 100 | 100 | 100 | 100 | 70 | 30 | 0 |
| CHEATGRASS | | | | | | | | | — | 0 | 0 | 0 |
| LAMBSQUARTER | 100 | 100 | 100 | 100 | 100 | 100 | 100 | 100 | 100 | 100 | 90 | 70 |
| CHICKWEED | 60 | 50 | 30 | 20 | 60 | 60 | 0 | 0 | 30 | 0 | 0 | 0 |
| DOWNY BROME | 100 | 100 | 90 | 40 | 80 | 90 | 60 | 0 | 30 | 0 | 0 | 0 |

Test C

Seeds of the treated crop and weed species were planted in a blend of peat and sandy loam and grown in the greenhouse for 10 to 21 days before postemergence treatment of the subject herbicide. Preemergence treatments were prepared immediately before herbicide application using sandy loam soil as the planting media. The compound of interest was diluted in a nonphytotoxic solvent composed of; acetone, water, a humectant and Poe sorbitan monolaurate, with aliquots taken for the various rates tested. Herbicide applications were made using a belt spray applying the material over the plant leaves for postemergence treatments and over the moistened soil surface in the preemergence treatments. After herbicide treatment, the pots were removed to the greenhouse where they were maintained under standard conditions for 21 days at which time visual evaluations of each species were made using a scale of 0 equal to no injury or control and 100 equal to complete kill of the plant. The data for this evaluation is shown in Table C.

TABLE C

| | CMPD 17 | | | | |
|---|---|---|---|---|---|
| RATE G/HA | 0250 | 0125 | 0064 | 0032 | 0016 |
| POSTEMERGENCE | | | | | |
| ERA WHEAT | 0 | 0 | 0 | 0 | 0 |
| KLAGES BARLEY | 30 | 10 | 10 | 10 | 10 |
| WILD OATS | 90 | 60 | 20 | 10 | 0 |
| DOWNY BROME | 10 | 10 | 0 | 0 | 0 |
| CHEAT GRASS | 10 | 10 | 0 | 0 | 0 |
| BLACKGRASS | 50 | 20 | 10 | 10 | 10 |
| ANN. BLUEGRASS | 00 | 10 | 10 | 10 | 0 |
| GREEN FOXTAIL | 100 | 100 | 100 | 100 | 100 |
| ITALN. RYEGRASS | 90 | 70 | 30 | 10 | 10 |
| ALTEX RAPE | 100 | 70 | 50 | 20 | 20 |
| CENTURK WHEAT | 20 | 0 | 0 | 0 | 0 |
| IGRI BARLEY | 30 | 10 | 10 | 10 | 10 |
| JOINT GOATGRASS | 10 | 10 | 10 | 0 | 0 |
| WILD OATS STG 2 | 0 | 0 | 0 | 0 | 0 |
| BLACKGRASS STG 2 | 40 | 10 | 10 | 0 | 0 |
| CTCHWD BEDSTRAW | 90 | 50 | 40 | 20 | 10 |
| WILD BUCKWHEAT | 100 | 100 | 100 | 100 | 60 |
| KOCHIA | 100 | 100 | 100 | 70 | 60 |
| SNTLS CHAMOMILE | 100 | 70 | 10 | 0 | 0 |
| BLACK NIGHTSHAD | 100 | 100 | 100 | 100 | 80 |
| PERSN SPEEDWELL | 100 | 100 | 70 | 70 | 60 |
| USH11 SUGARBEET | 100 | 90 | 90 | 70 | 70 |
| IVYLF SPEEDWELL | 100 | 100 | 100 | 30 | 0 |
| LAMBSQUARTER | 100 | 100 | 90 | 80 | 60 |
| FIELD PENNYCRES | 100 | 70 | 70 | 30 | 30 |
| FIELD VIOLET | 100 | 100 | 90 | 70 | 70 |
| PREEMERGENCE | | | | | |
| ERA WHEAT | 100 | 100 | 90 | 70 | 70 |
| KLAGES BARLEY | 90 | 70 | 70 | 50 | 40 |
| WILD OATS | 100 | 90 | 90 | 70 | 60 |
| DOWNY BROME | 60 | 60 | 20 | 0 | 0 |
| CHEAT GRASS | 100 | 90 | 70 | 70 | 60 |
| BLACKGRASS | 100 | 80 | 60 | 60 | 40 |
| ANN. BLUEGRASS | 100 | 100 | 100 | 80 | 70 |
| GREEN FOXTAIL | 100 | 100 | 100 | 100 | 100 |
| ITALN. RYEGRASS | 100 | 100 | 100 | 80 | 70 |
| ALTEX RAPE | 100 | 90 | 90 | 70 | 70 |
| CENTURK WHEAT | 100 | 100 | 80 | 70 | 70 |
| IGRI BARLEY | 90 | 90 | 70 | 50 | 40 |
| JOINT GOATGRASS | 70 | 40 | 40 | 40 | 30 |
| CTCHWD BEDSTRAW | 80 | 60 | 60 | 20 | 20 |
| WILD BUCKWHEAT | 100 | 100 | 100 | 100 | 70 |
| KOCHIA | 100 | 100 | 100 | 100 | 70 |
| SNTLS CHAMOMILE | 100 | 100 | 100 | 100 | 100 |
| BLACK NIGHTSHAD | 100 | 100 | 100 | 100 | 100 |
| PERSN SPEEDWELL | 100 | 70 | 70 | 60 | 40 |
| USH11 SUGARBEET | 100 | 100 | 100 | 100 | 100 |
| IVYLF SPEEDWELL | 100 | 100 | 100 | 100 | 80 |
| LAMBSQUARTER | 100 | 100 | 100 | 100 | 100 |
| FIELD PENNYCRES | 100 | 100 | 100 | 100 | 100 |
| FIELD VIOLET | 100 | 90 | 90 | 90 | 70 |

What is claimed is:

1. A compound of the formula

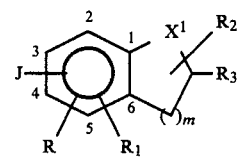

wherein,

R is H, Cl, F, $C_1$-$C_2$ alkyl or $C_1$-$C_3$ alkoxy;

$R_1$ is H, F, Cl, Br, $CH_3$, $OCH_3$, CN, $CF_3$, $OCF_3$ or $OCF_2H$;

$X^1$ is S;

$R_2$ is H, $CH_3$ or $CH_2CH_3$;

$R_3$ is H, $C_1$-$C_4$ haloalkyl, $CR_2R_7CN$, CN, $CR_2R_4R_7$, COCl, $COR_4$, $C(NOR_6)R_2$, $CO_2R_4$, $CONR_4R_2$, $CHR_2OH$, $CO_2(CH_2)_2Si(CH_3)_3$, $CONR_2SO_2CH_3$, $CHR_2CO_2R_4$, $CONHCH(CH_3)CONHCH(CH_3)CO_2CH_3$, $CHR_2COR_4$, $CHR_2OSO_2(C_1$-$C_4$ alkyl), $CHR_2OC(O)R_4$, $CHR_2OC(O)N(R_2)_2$, $CHR_2OC(O)N(R_2)OCH_3$, $CHR_2OC(O)N(R_2)Ph$, $HC=CH_2$ or C|CH;

$R_4$ is H, $C_1$-$C_4$ alkyl, $C_1$-$C_4$ haloalkyl, $C_2$-$C_6$ alkenyl, $C_3$-$C_6$ alkynyl, $C_2$-$C_4$ haloalkenyl, phenyl, $C_1$-$C_4$ alkylphenyl, $C_3$-$C_6$ alkoxycarbonylalkyl or $(CH_2CH_2O)_bR_2$;

b=1 to 6;

m is 1; n is 1 or 2;

J is

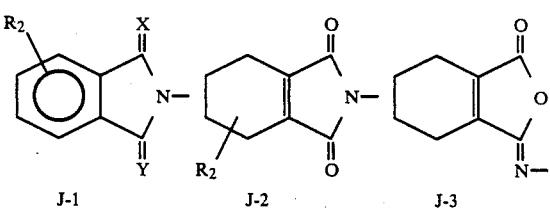

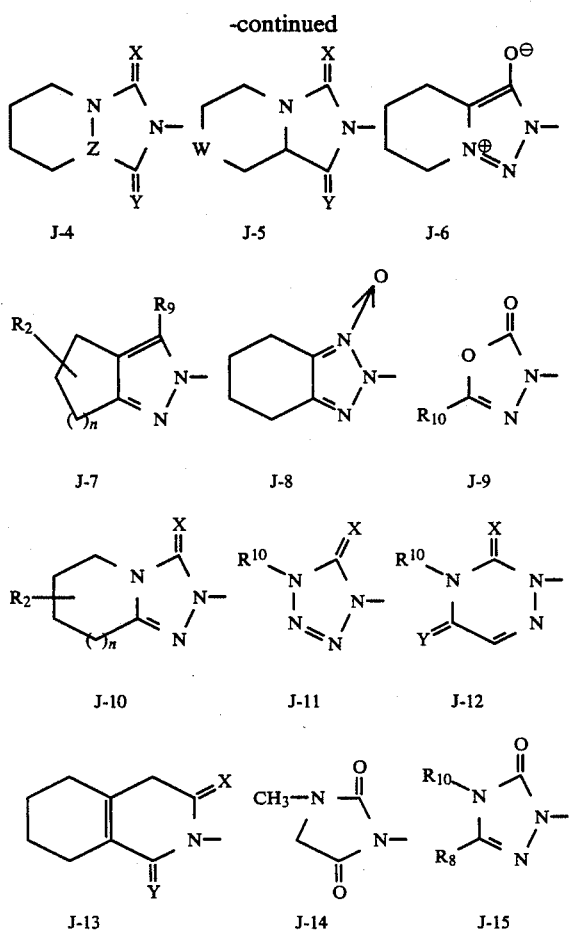

wherein
X and Y each is O or S;
Z is C or N;
W is S or $SO_2$;
$R_6$ is H, $C_1-C_5$ alkyl, allyl, propargyl, benzyl, $CH_2CO_2CH_3$ or $CH_2CO_2CH_2CH_3$;
$R_7$ is H or $CH_3$;
$R_8$ is Cl, $C_1-C_4$ alkyl or $C_1-C_4$ haloalkyl;
$R_9$ is Cl, F, Br, $CH_3$, CN, $OCH_3$, $SCH_3$ or $SO_2CH_3$; and
$R_{10}$ is $C_1-C_4$ alkyl or $C_1-C_4$ haloalkyl.

2. A compound of claim 1 wherein
R and $R_1$ are H or halogen; and
$R_2$ is H.

3. The compounds of claim 1 wherein
$R_4$ is H, $C_1-C_3$ alkyl, $C_1-C_2$ haloalkyl,
allyl, propargyl, $C_3$ haloalkenyl, $C_3-C_4$
alkoxycarbonylalkyl or $(CH_2CH_2O)_b R_2$; and
b is 1 or 2.

4. The Compounds of claim 1 wherein
$R_3$ is H, CN, $C_1-C_2$ haloalkyl, $CR_2R_7R_4$, $CR_2R_7CN$, $CH=CH_2$, C|CH, COCl, $COR_4$, $C(NOR_6)R_2$, $CO_2R_4$, $CH_2COR_4$, $CH_2CO_2R_4$, $CH_2OC(O)R_4$ or $CH_2OC(O)N(CH_3)_2$; and
$R_6$ is H, allyl, $C_1-C_3$ alkyl or $CH_2CO_2CH_2CH_3$.

5. The compounds of claim 1 wherein
J is J-2, J-3, J-4, J-7, J-9, J-10, J-11, J-12 or J-15; and
X and Y are O.

6. The compound of claim 1 wherein
$R_9$ is Cl or Br; and $R_8$ is $CH_3$.

7. The compounds of claim 1 wherein
J is in the 5 position;
R is F or Cl and in the 4 position; and
$R_1$ is Cl or Br and in the 2 position.

8. The compounds of claim 1 wherein
J is in the 4 position;
R is F or Cl and is in the 3 position; and
$R_1$ is H.

9. The compounds of claim 1 wherein
J is in the 3 position;
R is F or Cl and is in the 4 position; and
$R_1$ is H.

10. The compounds of claim 1 wherein
J is in the 2 position;
R is F or Cl and is in the 3 position; and
$R_1$ is Cl or Br and is in the 5 position.

11. The compounds of claim 1 wherein
J is J-2.

12. The compounds of claim 1 wherein
J is J-10 and
n is 1.

13. A compound of claim 1 wherein J is J-2; $R_2$ on J-2 is H; R is fluoro in the 5-position; $R_1$ is chloro in the 7-position; $R_2$ is H; $R_3$ is $CO_2R_4$; $R_4$ is $CH_3$; and $X_1$ is S.

14. A compound of claim 1 which is methyl 7-chloro-5-fluoro-4-(2,3,4,5,6,7-hexahydro-1,3-dioxo-1H-isoindol-2-yl)-2,3-dihydrobenzo[b]thiophene-2-carboxylate.

15. A composition suitable for controlling the growth of undesired vegetation which comprises an effective amount of a compound of claim 1 and at least one of the following: surfactant, solid or liquid diluent.

16. A composition suitable for controlling the growth of undesired vegetation which comprises an effective amount of a compound of claim 2 and at least one of the following: surfactant, solid or liquid diluent.

17. A composition suitable for controlling the growth of undesired vegetation which comprises an effective amount of a compound of claim 3 and at least one of the following: surfactant, solid or liquid diluent.

18. A composition suitable for controlling the growth of undesired vegetation which comprises an effective amount of a compound of claim 4 and at least one of the following: surfactant, solid or liquid diluent.

19. A composition suitable for controlling the growth of undesired vegetation which comprises an effective amount of a compound of claim 5 and at least one of the following: surfactant, solid or liquid diluent.

20. A composition suitable for controlling the growth of undesired vegetation which comprises an effective amount of a compound of claim 6 and at least one of the following: surfactant, solid or liquid diluent.

21. A composition suitable for controlling the growth of undesired vegetation which comprises an effective amount of a compound of claim 7 and at least one of the following: surfactant, solid or liquid diluent.

22. A method for controlling the growth of undesired vegetation which comprises applying to the locus to be protected an effective amount of a compound of claim 1.

23. A method for controlling the growth of undesired vegetation which comprises applying to the locus to be protected an effective amount of a compound of claim 2.

24. A method for controlling the growth of undesired vegetation which comprises applying to the locus to be protected an effective amount of a compound of claim 3.

25. A method for controlling the growth of undesired vegetation which comprises applying to the locus to be protected an effective amount of a compound of claim 4.

26. A method for controlling the growth of undesired vegetation which comprises applying to the locus to be protected an effective amount of a compound of claim 5.

27. A method for controlling the growth of undesired vegetation which comprises applying to the locus to be protected an effective amount of a compound of claim 6.

28. A method for controlling the growth of undesired vegetation which comprises applying to the locus to be protected an effective amount of a compound of claim 7.

29. The method of claim 22 wherein the locus to be protected is a cereal crop and the undesired vegetation is nightshade.

* * * * *